(12) United States Patent
Nakagawara et al.

(10) Patent No.: US 7,618,787 B2
(45) Date of Patent: Nov. 17, 2009

(54) METHOD OF SCREENING COMPOUND CAPABLE OF ACCELERATING OR INHIBITING APOPTOSIS, APOPTOSIS ACCELARATOR AND APOPTOSIS INHIBITOR

(75) Inventors: Akira Nakagawara, Chiba (JP); Toshinori Ozaki, Chiba (JP)

(73) Assignees: Hisamitsu Pharmaceutical Co., Inc., Saga (JP); Chiba-Prefecture, Chiba (JP)

( * ) Notice: Subject to any disclaimer, the term of this patent is extended or adjusted under 35 U.S.C. 154(b) by 153 days.

(21) Appl. No.: 10/594,448

(22) PCT Filed: Mar. 23, 2005

(86) PCT No.: PCT/JP2005/005247

§ 371 (c)(1),
(2), (4) Date: May 15, 2007

(87) PCT Pub. No.: WO2005/093082

PCT Pub. Date: Oct. 6, 2005

(65) Prior Publication Data

US 2008/0032320 A1 Feb. 7, 2008

(30) Foreign Application Priority Data

Mar. 26, 2004 (JP) .............................. 2004-093266
Jun. 14, 2004 (JP) .............................. 2004-176107

(51) Int. Cl.
*G01N 33/53* (2006.01)
(52) U.S. Cl. ...................................... 435/7.1
(58) Field of Classification Search ................... 435/7.1
See application file for complete search history.

(56) References Cited

OTHER PUBLICATIONS

YinLing Hu, et al., "Abnormal Morphogenesis But Intact IKK Activation in Mice Lacking the IKKα Subunit of IκB Kinase", *Science*, vol. 284, Apr. 9, 1999, pp. 316-320.
Catherine H. Regnier, et al., "Identification and Characterization of an IκB Kinase", *Cell*, vol. 90, Jul. 25, 2997, pp. 373-383.
Rakesh K. Srivastava, et al., "Deletion of the loop region of Bcl-2 completely blocks paclitaxel-induced apoptosis", *Proc. Natl. Acad. Sci.*, vol. 96, Mar. 1999, pp. 3775-3780.
JianGen Gong, et al., "The tyrosine kinase c-Abl regulates p73 in apoptotic response to cisplatin-induced DNA damage", *Nature*, vol. 399, Jun. 24, 2999, pp. 806-809.
Reuven Agami, et al., "Interaction of c-Abl and p73α and their collaboration to induce apoptosis", *Nature*, vol. 399, Jun. 24, 1999, pp. 809-813.
Zhi-min Yuan, et al., "p73 is regulated by tyrosine kinase c-Abl in the apoptotic response to DNA damage", *Nature*, vol. 399, Jun. 24, 1999, pp. 814-817.
Yoshiaki Shikama, et al., "Caspase-8 and caspase-10 activate NF-κB through RIP, NIK and IKKα kinases", *Eur. J. Immunol.*, vol. 33, No. 7, Jul. 2003, pp. 1998-2006.

Y. Wan et al., "The Survival of Antigen-Stimulated T Cells Requires NFkB-Mediated Inhibition of p73 Expression", Immunity, vol. 18, Mar. 2003, pp. 331-342.
V. Tergaonkar et al., "p53 stabilization is decreased upon NFkB activation: A role for NFkB in acquisition of resistance to chemotherapy", Cancer Cell, vol. 1, Jun. 2002, pp. 493-503.
G. Webster et al., "Transcriptional Cross Talk between NF-kB and p53", Molecular and Cellular Biology, May 1999, pp. 3485-3495.
K. Ryan et al., "Role of NF-kB in p53-mediated programmed cell death", Nature, vol. 404, Apr. 20, 2000, pp. 892-897.
H. Wu et al., "NF-kB Activation of p53: A Potential Mechanism for Suppressing Cell Growth in Response to Stress",.The Journal of Biological Chemistry, vol. 269, No. 31, Aug. 5, 1994, pp. 20067-20074.
X. Sun et al., "Identification of a Novel p53 Promoter Element Involved in Genotoxic Stress-Inducible p53 Gene Expression", Molecular and Cellular Biology, vol. 15, No. 8, Aug. 1995, pp. 4489-4496.
A. Hellin et al., "Nuclear factor—κB-dependent regulation of p53 gene expression induced by daunomycin genotoxic drug", Oncogene 16, 1998, pp. 1187-1195.
M. Koegl et al., "A Novel Ubiquitination Factor, E4, Is Involved in Multiubiquitin Chain Assembly", Cell, vol. 96, Mar. 5, 1999, pp. 635-644.
S. Hatakeyama et al., "U Box Proteins as a New Family of Ubiquitin-Protein Ligases", The Journal of Biological Chemistry, vol. 276, No. 35, Aug. 31, 2001, pp. 33111-33120.
M. Ohira et al., "Identification and characterization of a 500-kb homozygously deleted region at 1p36.2-p36.3 in a neuroblastoma cell line", Oncogene 19, (2000), pp. 4302-4307.
J. Mahoney et al., "The human homologue of the yeast polyubiquitination factor Ufd2p is cleaved by caspase 6 and granzyme B during apoptosis", Biochem. J.361, (2002), pp. 587-595.
Y. Bayon et al., "Inhibition of IkB Kinase by a New Class of Retinoide-Related Anticancer Agents That Induce Apoptosis", Molecular and Cellular Biology, Feb. 2003, pp. 1061-1074.
G. Melino et al., "p73: Friend of Foe in Tumorigenesis", Nature Reviews Cancer, vol. 2, Aug. 2002, pp. 605-615.
K. Vousden et al., "Live or Let Die: The Cell's Response to p53", Nature Reviews Cancer, vol. 2, Aug. 2002, pp. 594-604.
A. Birbach et al., "Signaling Molecules of the NF-κB Pathway Shuttle Constitutively between Cytoplasm and Nucleus", The Journal of Biological Chemistry, vol. 277, No. 13, Mar. 29, 2002, pp. 10842-10851.
Y. Yamamoto et al., "Histone H3 phosphorylation by IKK-α is critical for cytokine-induced gene expression", Nature, vol. 423, Jun. 2003, pp. 655-659.
V. Anest et al., "A nucleosomal function for IkB kinase-α in NF-kB-dependent gene expression", Nature, vol. 423, Jun. 2003, pp. 659-663.
C. Lee et al., "Promoter specificity and stability control of the p53-related protein p73", Oncogene 18, (1999), pp. 4171-4181.

(Continued)

*Primary Examiner*—Karen Cochrane Carlson
(74) *Attorney, Agent, or Firm*—Sughrue Mion, PLLC

(57) ABSTRACT

A method for screening a pro-apoptotic compound comprising a determination step of determining a compound enhancing interaction between p73 and IKK-α as a pro-apoptotic compound.

1 Claim, 36 Drawing Sheets

OTHER PUBLICATIONS

L. Ling et al., "NF-κB-inducing kinase activates IKK-α by phosphorylation of Ser-176", Proc. Natl. Acad. Sci. USA, vol. 95, Mar. 1998, pp. 3792-3797.

"Inhibitor of nuclear factor kappa-B kinase subunit alpha", Database UniProt [Online], retrieved from EBI accession No. UNIPROT:015111, Database accession No. 015111, Jan. 1, 1998 (XP002466446).

F. Kazushige et al., "Stabilization of p73 by nuclear I kappa B kinase-alpha mediates cisplatin-induced apoptosis", Journal of Biological Chemistry, vol. 282, No. 25, ISSN:0021-9258, Jun. 2007, pp. 18365-18378, (XP00246445).

Fig.20
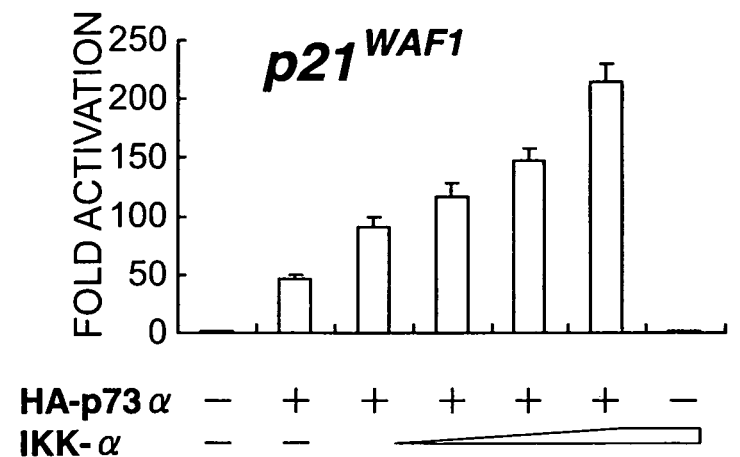
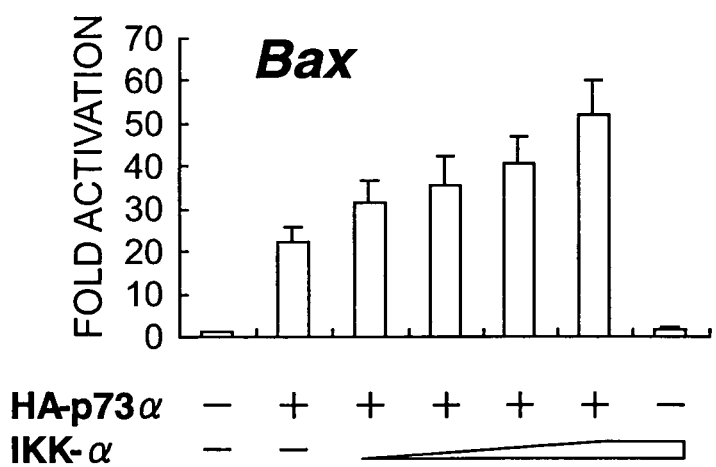
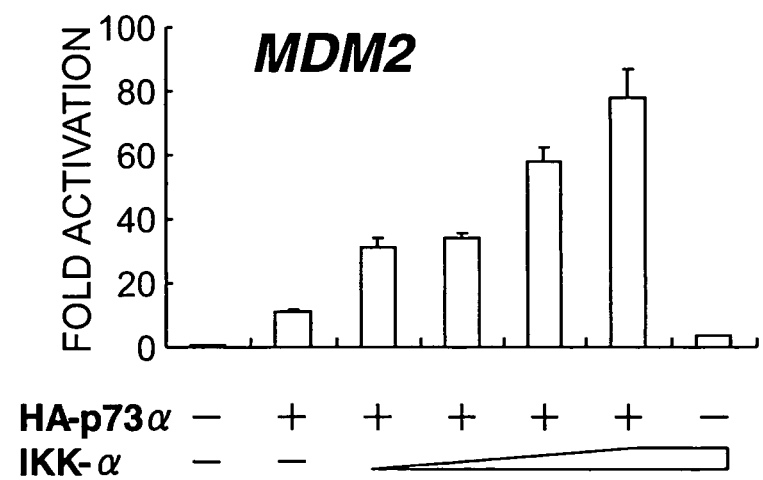

*Fig.22*
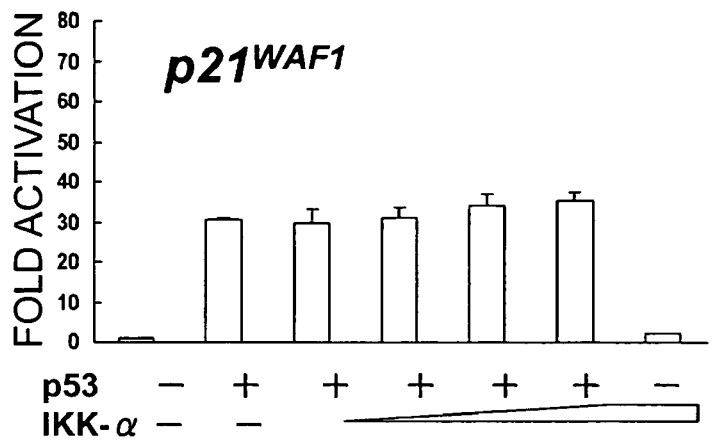
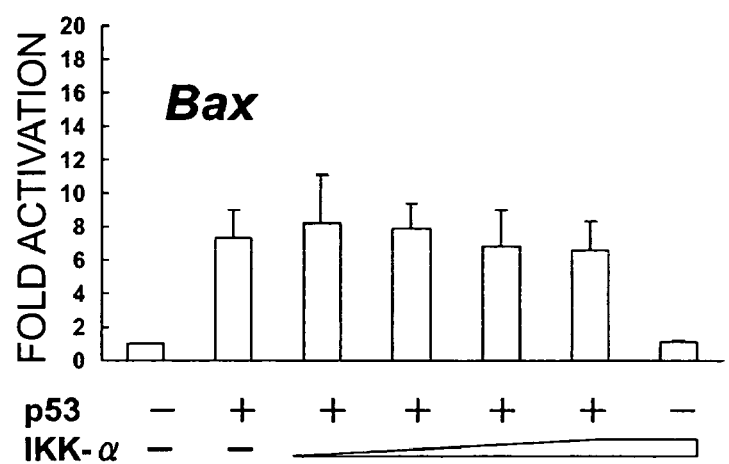

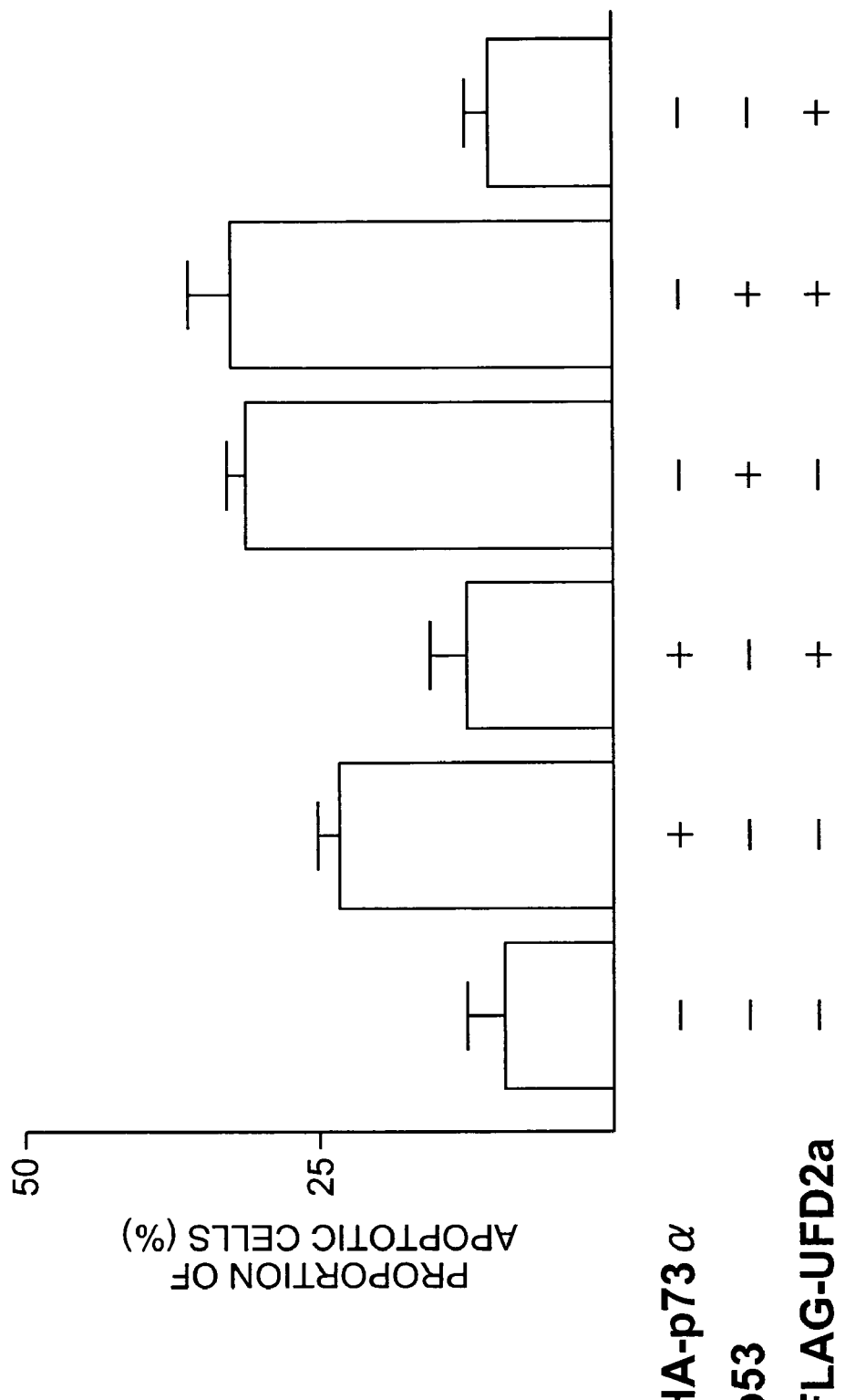

SEQUENCE LISTING

```
<160> NUMBER OF SEQ ID NOS: 26

<210> SEQ ID NO 1
<211> LENGTH: 20
<212> TYPE: DNA
<213> ORGANISM: Artificial
<220> FEATURE:
<223> OTHER INFORMATION: primer for IKK-alpha

<400> SEQUENCE: 1
ccgacttcag cagaacatga                                                  20

<210> SEQ ID NO 2
<211> LENGTH: 20
<212> TYPE: DNA
<213> ORGANISM: Artificial
<220> FEATURE:
<223> OTHER INFORMATION: primer for IKK-alpha

<400> SEQUENCE: 2
tggggacagt gaacaagtga                                                  20

<210> SEQ ID NO 3
<211> LENGTH: 20
<212> TYPE: DNA
<213> ORGANISM: Artificial
<220> FEATURE:
<223> OTHER INFORMATION: primer for IKK-beta

<400> SEQUENCE: 3
aaccagcatc cagattgacc                                                  20

<210> SEQ ID NO 4
<211> LENGTH: 20
<212> TYPE: DNA
```

```
<213> ORGANISM: Artificial
<220> FEATURE:
<223> OTHER INFORMATION: primer for IKK-beta

<400> SEQUENCE: 4
ctctaggtcg tccagcgttc                                              20

<210> SEQ ID NO 5
<211> LENGTH: 20
<212> TYPE: DNA
<213> ORGANISM: Artificial
<220> FEATURE:
<223> OTHER INFORMATION: primer for IKK-gamma

<400> SEQUENCE: 5
cctcactccc tgtgaagctc                                              20

<210> SEQ ID NO 6
<211> LENGTH: 20
<212> TYPE: DNA
<213> ORGANISM: Artificial
<220> FEATURE:
<223> OTHER INFORMATION: primer for IKK-gamma

<400> SEQUENCE: 6
gagactcttc gcccagtacg                                              20

<210> SEQ ID NO 7
<211> LENGTH: 20
<212> TYPE: DNA
<213> ORGANISM: Artificial
<220> FEATURE:
<223> OTHER INFORMATION: primer for IkB-alpha

<400> SEQUENCE: 7
gcaaaatcct gacctggtgt                                              20

<210> SEQ ID NO 8
<211> LENGTH: 20
<212> TYPE: DNA
<213> ORGANISM: Artificial
<220> FEATURE:
<223> OTHER INFORMATION: primer for IkB-alpha

<400> SEQUENCE: 8
gctcgtcctc tgtgaactcc                                              20

<210> SEQ ID NO 9
<211> LENGTH: 30
<212> TYPE: DNA
<213> ORGANISM: Artificial
<220> FEATURE:
<223> OTHER INFORMATION: primer for p53

<400> SEQUENCE: 9
atttgatgct gtccccggac gatattgaac                                   30

<210> SEQ ID NO 10
<211> LENGTH: 30
<212> TYPE: DNA
<213> ORGANISM: Artificial
<220> FEATURE:
<223> OTHER INFORMATION: primer for p53

<400> SEQUENCE: 10 acccttttg gacttcaggt ggctggagtg                                    30
```

```
<210> SEQ ID NO 11
<211> LENGTH: 20
<212> TYPE: DNA
<213> ORGANISM: Artificial
<220> FEATURE:
<223> OTHER INFORMATION: primer for p73-alpha

<400> SEQUENCE: 11
ccgggagaac tttgagatcc                                               20

<210> SEQ ID NO 12
<211> LENGTH: 20
<212> TYPE: DNA
<213> ORGANISM: Artificial
<220> FEATURE:
<223> OTHER INFORMATION: primer for p73-alpha

<400> SEQUENCE: 12
atcttcaggg cccccaggtc                                               20

<210> SEQ ID NO 13
<211> LENGTH: 20
<212> TYPE: DNA
<213> ORGANISM: Artificial
<220> FEATURE:
<223> OTHER INFORMATION: primer for p21WAF1

<400> SEQUENCE: 13
ccgggagaac tttgagatcc                                               20

<210> SEQ ID NO 14
<211> LENGTH: 20
<212> TYPE: DNA
<213> ORGANISM: Artificial
<220> FEATURE:
<223> OTHER INFORMATION: primer for p21WAF1

<400> SEQUENCE: 14
atcttcaggg cccccaggtc                                               20

<210> SEQ ID NO 15
<211> LENGTH: 20
<212> TYPE: DNA
<213> ORGANISM: Artificial
<220> FEATURE:
<223> OTHER INFORMATION: primer for Bax

<400> SEQUENCE: 15
tttgcttcag ggtttcatcc                                               20

<210> SEQ ID NO 16
<211> LENGTH: 20
<212> TYPE: DNA
<213> ORGANISM: Artificial
<220> FEATURE:
<223> OTHER INFORMATION: primer for Bax

<400> SEQUENCE: 16
cagttgaagt tgccgtcaga                                               20

<210> SEQ ID NO 17
<211> LENGTH: 20
<212> TYPE: DNA
<213> ORGANISM: Artificial
<220> FEATURE:
```

<223> OTHER INFORMATION: primer for GAPDH

<400> SEQUENCE: 17
acctgacctg ccgtctagaa                                              20

<210> SEQ ID NO 18
<211> LENGTH: 20
<212> TYPE: DNA
<213> ORGANISM: Artificial
<220> FEATURE:
<223> OTHER INFORMATION: primer for GAPDH

<400> SEQUENCE: 18
tccaccaccc tgttgctgta                                              20

<210> SEQ ID NO 19
<211> LENGTH: 31
<212> TYPE: DNA
<213> ORGANISM: Artificial
<220> FEATURE:
<223> OTHER INFORMATION: primer for IKK-alpha

<400> SEQUENCE: 19
ccggaattcg agcggccccc ggggctgcgg c                                 31

<210> SEQ ID NO 20
<211> LENGTH: 45
<212> TYPE: DNA
<213> ORGANISM: Artificial
<220> FEATURE:
<223> OTHER INFORMATION: primer for IKK-alpha

<400> SEQUENCE: 20
ccgctcgagc ggtcattctg ctaaccaact ccaatcaaga ctcat                  45

<210> SEQ ID NO 21
<211> LENGTH: 51
<212> TYPE: DNA
<213> ORGANISM: Artificial
<220> FEATURE:
<223> OTHER INFORMATION: primer for IKK-alpha(K44A)

<400> SEQUENCE: 21
gcgtcttgtc gtttagagct aagttccaaa acagagagc gatggtgcca t            51

<210> SEQ ID NO 22
<211> LENGTH: 51
<212> TYPE: DNA
<213> ORGANISM: Artificial
<220> FEATURE:
<223> OTHER INFORMATION: primer for IKK-alpha(K44A)

<400> SEQUENCE: 22
aattgctatt ttgagatcaa gttcccggtg ctggtacaga ctgacgttcc c           51

<210> SEQ ID NO 23
<211> LENGTH: 3579
<212> TYPE: DNA
<213> ORGANISM: Homo sapiens

<400> SEQUENCE: 23
cacgcgtccg cgagaaggag gactcgcaag cctcggcggc ccggaaccgg cctcggactg    60
tcgacggaac ctgaggccgc ttgccctccc gccccatgga gcggccccg gggctgcggc    120 cgggcgcggg cggcccctgg gagatgcggg agcggctggg caccggcggc ttcgggaacg   180

```
tctgtctgta ccagcatcgg gaacttgatc tcaaaatagc aattaagtct tgtcgcctag      240
agctaagtac caaaaacaga gaacgatggt gccatgaaat ccagattatg aagaagttga      300
accatgccaa tgttgtaaag gcctgtgatg ttcctgaaga attgaatatt ttgattcatg      360
atgtgcctct tctagcaatg gaatactgtt ctggaggaga tctccgaaag ctgctcaaca      420
aaccagaaaa ttgttgtgga cttaaagaaa gccagatact ttctttacta agtgatatag      480
ggtctgggat tcgatatttg catgaaaaca aaattataca tcgagatcta aaacctgaaa      540
acatagttct tcaggatgtt ggtggaaaga taatacataa aataattgat ctgggatatg      600
ccaaagatgt tgatcaagga agtctgtgta catcttttgt gggaacactg cagtatctgg      660
ccccagagct cttttgagaat aagccttaca cagccactgt tgattattgg agctttggga      720
ccatggtatt tgaatgtatt gctggatata ggccttttttt gcatcatctg cagccattta      780
cctggcatga aagattaag aagaaggatc caaagtgtat atttgcatgt gaagagatgt      840
caggagaagt tcggtttagt agccatttac ctcaaccaaa tagcctttgt agtttaatag      900
tagaacccat ggaaaactgg ctacagttga tgttgaattg ggaccctcag cagagaggag      960
gacctgttga ccttactttg aagcagccaa gatgttttgt attaatggat cacattttga     1020
atttgaagat agtacacatc ctaaatatga cttctgcaaa gataattctc tttctgttac     1080
cacctgatga aagtcttcat tcactacagt ctcgtattga gcgtgaaact ggaataaata     1140
ctggttctca agaacttctt tcagagacag gaatttctct ggatcctcgg aaaccagcct     1200
ctcaatgtgt tctagatgga gttagaggct gtgatagcta tggtttat ttgtttgata      1260 aaagtaaaac tgtatatgaa gggccatttg cttccagaag tttatctgat tgtgtaaatt     1320
atattgtaca ggacagcaaa atacagcttc aattataca gctgcgtaaa gtgtgggctg     1380
aagcagtgca ctatgtgtct ggactaaaag aagactatag caggctctttt cagggacaaa     1440 gggcagcaat gttaagtctt cttagatata atgctaactt aacaaaaatg aagaacactt     1500
tgatctcagc atcacaacaa ctgaaagcta aattggagtt ttttcacaaa agcattcagc     1560
ttgacttgga gagatacagc gagcagatga cgtatgggga tcttcagaa aaaatgctaa     1620 aagcatggaa agaaatggaa gaaaaggcca tccactatgc tgaggttggt gtcattggat     1680
acctggagga tcagattatg tcttttgcatg ctgaaatcat ggagctacag aagagcccct     1740
atggaagacg tcagggagac ttgatggaat ctctggaaca gcgtgccatt gatctatata     1800
agcagttaaa acacagacct tcagatcact cctacagtga cagcacagag atggtgaaaa     1860
tcattgtgca cactgtgcag agtcaggacc gtgtgctcaa ggagctgttt ggtcatttga     1920
gcaagttgtt gggctgtaag cagaagatta ttgatctact ccctaaggtg gaagtggccc     1980
tcagtaatat caaagaagct gacaatactg tcatgttcat gcagggaaaa aggcagaaag     2040
aaatatggca tctccttaaa attgcctgta cacagagttc tgcccggtcc cttgtaggat     2100
ccagtctaga aggtgcagta accctcaga catcagcatg gctgcccccg acttcagcag     2160
aacatgatca ttctctgtca tgtgtggtaa ctcctcaaga tggggagact tcagcacaaa     2220
tgatagaaga aaatttgaac tgccttggcc atttaagcac tattattcat gaggcaaatg     2280
aggaacaggg caatagtatg atgaatcttg attggagttg gttaacagaa tgagttgtca     2340
cttgttcact gtccccaaac ctatggaagt tgttgctata catgttggaa atgtgttttt     2400
cccccatgaa accattcttc agacatcagt caatggaaga aatggctatg aacagaaact     2460
acatttctac tatgatcaga agaacatgat tttacaagta taacagtttt gagtaattca     2520
```

```
agcctctaaa cagacaggaa tttagaaaaa gtcaatgtac ttgtttgaat atttgtttta   2580
ataccacagc tatttagaag catcatcacg acacatttgc cttcagtctt ggtaaaacat   2640
tacttattta actgattaaa aataccttct atgtattagt gtcaacttttt aacttttggg   2700 cgtaagacaa agtgtagttt tgtatacaga gaagaaaacc tcaagtaata ggcatttaa    2760 gtaaaagtct acctgtgttt ttttctaaaa aggctgctca caagttctat ttcttgaaga   2820
ataaattcta cctccttgtg ttgcactgaa caggttctct tcctggcatc ataaggagtt   2880
ggtgtaatca ttttaaattc cactgaaaat ttaacagtat ccccttctca tcgaagggat   2940
tgtgtatctg tgcttctaat attagttggc tttcataaat catgttgttg tgtgtatatg   3000
tatttaagat gtacatttaa taatatcaaa gagaagatgc ctgttaattt ataatgtatt   3060
tgaaaattac atgttttttc atttgtaaaa atgagtcatt tgtttaaaca atctttcatg   3120
tcttgtcata caaatttata aaggtctgca ctcctttatc tgtaattgta attccaaaat   3180
ccaaaaagct ctgaaaacaa ggtttccata agcttggtga caaaattcat ttgcttgcaa   3240
tctaatctga actgaccttg aatcttttta tcccatttag tgtgaatatt cctttatttt   3300
gctgcttgat gatgagaggg agggctgctg ccacagactg tggtgagggc tggttaatgt   3360
agtatggtat atgcacaaaa ctactttct aaaatctaaa atttcataat tctgaaacaa    3420
cttgccccaa gggtttcaga gaaaggactg tggacctcta tcatctgcta agtaatttag   3480
aagatattat ttgtcttaaa aaatgtgaaa tgcttttata ttctaatagt ttttcacttt    3540
gtgtattaaa tggtttttaa attaaaaaaa aaaaaaaaa                          3579
```

<210> SEQ ID NO 24
<211> LENGTH: 745
<212> TYPE: PRT
<213> ORGANISM: Homo sapiens

<400> SEQUENCE: 24

```
Met Glu Arg Pro Pro Gly Leu Arg Pro Gly Ala Gly Gly Pro Trp Glu
 1               5                  10                  15

Met Arg Glu Arg Leu Gly Thr Gly Gly Phe Gly Asn Val Cys Leu Tyr
            20                  25                  30

Gln His Arg Glu Leu Asp Leu Lys Ile Ala Ile Lys Ser Cys Arg Leu
        35                  40                  45

Glu Leu Ser Thr Lys Asn Arg Glu Arg Trp Cys His Glu Ile Gln Ile
    50                  55                  60

Met Lys Lys Leu Asn His Ala Asn Val Val Lys Ala Cys Asp Val Pro
65                  70                  75                  80

Glu Glu Leu Asn Ile Leu Ile His Asp Val Pro Leu Leu Ala Met Glu
                85                  90                  95

Tyr Cys Ser Gly Gly Asp Leu Arg Lys Leu Leu Asn Lys Pro Glu Asn
            100                 105                 110

Cys Cys Gly Leu Lys Glu Ser Gln Ile Leu Ser Leu Leu Ser Asp Ile
        115                 120                 125

Gly Ser Gly Ile Arg Tyr Leu His Glu Asn Lys Ile Ile His Arg Asp
    130                 135                 140

Leu Lys Pro Glu Asn Ile Val Leu Gln Asp Val Gly Gly Lys Ile Ile
145                 150                 155                 160

His Lys Ile Ile Asp Leu Gly Tyr Ala Lys Asp Val Asp Gln Gly Ser
                165                 170                 175

Leu Cys Thr Ser Phe Val Gly Thr Leu Gln Tyr Leu Ala Pro Glu Leu
            180                 185                 190
```

```
Phe Glu Asn Lys Pro Tyr Thr Ala Thr Val Asp Tyr Trp Ser Phe Gly
            195                 200                 205
Thr Met Val Phe Glu Cys Ile Ala Gly Tyr Arg Pro Phe Leu His His
        210                 215                 220
Leu Gln Pro Phe Thr Trp His Glu Lys Ile Lys Lys Asp Pro Lys
225                 230                 235                 240
Cys Ile Phe Ala Cys Glu Glu Met Ser Gly Glu Val Arg Phe Ser Ser
                245                 250                 255
His Leu Pro Gln Pro Asn Ser Leu Cys Ser Leu Ile Val Glu Pro Met
            260                 265                 270
Glu Asn Trp Leu Gln Leu Met Leu Asn Trp Asp Pro Gln Gln Arg Gly
        275                 280                 285
Gly Pro Val Asp Leu Thr Leu Lys Gln Pro Arg Cys Phe Val Leu Met
    290                 295                 300
Asp His Ile Leu Asn Leu Lys Ile Val His Ile Leu Asn Met Thr Ser
305                 310                 315                 320
Ala Lys Ile Ile Ser Phe Leu Pro Pro Asp Glu Ser Leu His Ser
                325                 330                 335
Leu Gln Ser Arg Ile Glu Arg Glu Thr Gly Ile Asn Thr Gly Ser Gln
            340                 345                 350
Glu Leu Leu Ser Glu Thr Gly Ile Ser Leu Asp Pro Arg Lys Pro Ala
        355                 360                 365
Ser Gln Cys Val Leu Asp Gly Val Arg Gly Cys Asp Ser Tyr Met Val
    370                 375                 380
Tyr Leu Phe Asp Lys Ser Lys Thr Val Tyr Glu Gly Pro Phe Ala Ser
385                 390                 395                 400
Arg Ser Leu Ser Asp Cys Val Asn Tyr Ile Val Gln Asp Ser Lys Ile
                405                 410                 415
Gln Leu Pro Ile Ile Gln Leu Arg Lys Val Trp Ala Glu Ala Val His
            420                 425                 430
Tyr Val Ser Gly Leu Lys Glu Asp Tyr Ser Arg Leu Phe Gln Gly Gln
        435                 440                 445
Arg Ala Ala Met Leu Ser Leu Leu Arg Tyr Asn Ala Asn Leu Thr Lys
    450                 455                 460
Met Lys Asn Thr Leu Ile Ser Ala Ser Gln Gln Leu Lys Ala Lys Leu
465                 470                 475                 480
Glu Phe Phe His Lys Ser Ile Gln Leu Asp Leu Glu Arg Tyr Ser Glu
                485                 490                 495
Gln Met Thr Tyr Gly Ile Ser Ser Glu Lys Met Leu Lys Ala Trp Lys
            500                 505                 510
Glu Met Glu Glu Lys Ala Ile His Tyr Ala Glu Val Gly Val Ile Gly
        515                 520                 525
Tyr Leu Glu Asp Gln Ile Met Ser Leu His Ala Glu Ile Met Glu Leu
    530                 535                 540
Gln Lys Ser Pro Tyr Gly Arg Arg Gln Gly Asp Leu Met Glu Ser Leu
545                 550                 555                 560
Glu Gln Arg Ala Ile Asp Leu Tyr Lys Gln Leu Lys His Arg Pro Ser
                565                 570                 575
Asp His Ser Tyr Ser Asp Ser Thr Glu Met Val Lys Ile Ile Val His
            580                 585                 590
Thr Val Gln Ser Gln Asp Arg Val Leu Lys Glu Leu Phe Gly His Leu
        595                 600                 605
```

```
Ser Lys Leu Leu Gly Cys Lys Gln Lys Ile Ile Asp Leu Leu Pro Lys
    610                 615                 620

Val Glu Val Ala Leu Ser Asn Ile Lys Glu Ala Asp Asn Thr Val Met
625                 630                 635                 640

Phe Met Gln Gly Lys Arg Gln Lys Glu Ile Trp His Leu Leu Lys Ile
                645                 650                 655

Ala Cys Thr Gln Ser Ser Ala Arg Ser Leu Val Gly Ser Ser Leu Glu
                660                 665                 670

Gly Ala Val Thr Pro Gln Thr Ser Ala Trp Leu Pro Pro Thr Ser Ala
                675                 680                 685

Glu His Asp His Ser Leu Ser Cys Val Val Thr Pro Gln Asp Gly Glu
690                 695                 700

Thr Ser Ala Gln Met Ile Glu Glu Asn Leu Asn Cys Leu Gly His Leu
705                 710                 715                 720

Ser Thr Ile Ile His Glu Ala Asn Glu Glu Gln Gly Asn Ser Met Met
                725                 730                 735

Asn Leu Asp Trp Ser Trp Leu Thr Glu
                740                 745

<210> SEQ ID NO 25
<211> LENGTH: 745
<212> TYPE: PRT
<213> ORGANISM: Artificial
<220> FEATURE:
<223> OTHER INFORMATION: IKK-alpha(K44A)

<400> SEQUENCE: 25

Met Glu Arg Pro Pro Gly Leu Arg Pro Gly Ala Gly Gly Pro Trp Glu
1               5                   10                  15

Met Arg Glu Arg Leu Gly Thr Gly Gly Phe Gly Asn Val Cys Leu Tyr
                20                  25                  30

Gln His Arg Glu Leu Asp Leu Lys Ile Ala Ile Ala Ser Cys Arg Leu
            35                  40                  45

Glu Leu Ser Thr Lys Asn Arg Glu Arg Trp Cys His Glu Ile Gln Ile
    50                  55                  60

Met Lys Lys Leu Asn His Ala Asn Val Val Lys Ala Cys Asp Val Pro
65                  70                  75                  80

Glu Glu Leu Asn Ile Leu Ile His Asp Val Pro Leu Leu Ala Met Glu
                85                  90                  95

Tyr Cys Ser Gly Gly Asp Leu Arg Lys Leu Leu Asn Lys Pro Glu Asn
                100                 105                 110

Cys Cys Gly Leu Lys Glu Ser Gln Ile Leu Ser Leu Leu Ser Asp Ile
            115                 120                 125

Gly Ser Gly Ile Arg Tyr Leu His Glu Asn Lys Ile Ile His Arg Asp
    130                 135                 140

Leu Lys Pro Glu Asn Ile Val Leu Gln Asp Val Gly Gly Lys Ile Ile
145                 150                 155                 160

His Lys Ile Ile Asp Leu Gly Tyr Ala Lys Asp Val Asp Gln Gly Ser
                165                 170                 175

Leu Cys Thr Ser Phe Val Gly Thr Leu Gln Tyr Leu Ala Pro Glu Leu
                180                 185                 190

Phe Glu Asn Lys Pro Tyr Thr Ala Thr Val Asp Tyr Trp Ser Phe Gly
            195                 200                 205

Thr Met Val Phe Glu Cys Ile Ala Gly Tyr Arg Pro Phe Leu His His
    210                 215                 220
```

-continued

```
Leu Gln Pro Phe Thr Trp His Glu Lys Ile Lys Lys Asp Pro Lys
225                 230                 235                 240

Cys Ile Phe Ala Cys Glu Glu Met Ser Gly Glu Val Arg Phe Ser Ser
                245                 250                 255

His Leu Pro Gln Pro Asn Ser Leu Cys Ser Leu Ile Val Glu Pro Met
            260                 265                 270

Glu Asn Trp Leu Gln Leu Met Leu Asn Trp Asp Pro Gln Gln Arg Gly
        275                 280                 285

Gly Pro Val Asp Leu Thr Leu Lys Gln Pro Arg Cys Phe Val Leu Met
    290                 295                 300

Asp His Ile Leu Asn Leu Lys Ile Val His Ile Leu Asn Met Thr Ser
305                 310                 315                 320

Ala Lys Ile Ile Ser Phe Leu Leu Pro Pro Asp Glu Ser Leu His Ser
                325                 330                 335

Leu Gln Ser Arg Ile Glu Arg Glu Thr Gly Ile Asn Thr Gly Ser Gln
            340                 345                 350

Glu Leu Leu Ser Glu Thr Gly Ile Ser Leu Asp Pro Arg Lys Pro Ala
        355                 360                 365

Ser Gln Cys Val Leu Asp Gly Val Arg Gly Cys Asp Ser Tyr Met Val
    370                 375                 380

Tyr Leu Phe Asp Lys Ser Lys Thr Val Tyr Glu Gly Pro Phe Ala Ser
385                 390                 395                 400

Arg Ser Leu Ser Asp Cys Val Asn Tyr Ile Val Gln Asp Ser Lys Ile
                405                 410                 415

Gln Leu Pro Ile Ile Gln Leu Arg Lys Val Trp Ala Glu Ala Val His
            420                 425                 430

Tyr Val Ser Gly Leu Lys Glu Asp Tyr Ser Arg Leu Phe Gln Gly Gln
        435                 440                 445

Arg Ala Ala Met Leu Ser Leu Leu Arg Tyr Asn Ala Asn Leu Thr Lys
    450                 455                 460

Met Lys Asn Thr Leu Ile Ser Ala Ser Gln Gln Leu Lys Ala Lys Leu
465                 470                 475                 480

Glu Phe Phe His Lys Ser Ile Gln Leu Asp Leu Glu Arg Tyr Ser Glu
                485                 490                 495

Gln Met Thr Tyr Gly Ile Ser Ser Glu Lys Met Leu Lys Ala Trp Lys
            500                 505                 510

Glu Met Glu Glu Lys Ala Ile His Tyr Ala Glu Val Gly Val Ile Gly
        515                 520                 525

Tyr Leu Glu Asp Gln Ile Met Ser Leu His Ala Glu Ile Met Glu Leu
    530                 535                 540

Gln Lys Ser Pro Tyr Gly Arg Arg Gln Gly Asp Leu Met Glu Ser Leu
545                 550                 555                 560

Glu Gln Arg Ala Ile Asp Leu Tyr Lys Gln Leu Lys His Arg Pro Ser
                565                 570                 575

Asp His Ser Tyr Ser Asp Ser Thr Glu Met Val Lys Ile Ile Val His
            580                 585                 590

Thr Val Gln Ser Gln Asp Arg Val Leu Lys Glu Leu Phe Gly His Leu
        595                 600                 605

Ser Lys Leu Leu Gly Cys Lys Gln Lys Ile Ile Asp Leu Leu Pro Lys
    610                 615                 620

Val Glu Val Ala Leu Ser Asn Ile Lys Glu Ala Asp Asn Thr Val Met
625                 630                 635                 640

Phe Met Gln Gly Lys Arg Gln Lys Glu Ile Trp His Leu Leu Lys Ile
```

```
                       645                 650                 655
Ala Cys Thr Gln Ser Ser Ala Arg Ser Leu Val Gly Ser Ser Leu Glu
                660                 665                 670

Gly Ala Val Thr Pro Gln Thr Ser Ala Trp Leu Pro Pro Thr Ser Ala
            675                 680                 685

Glu His Asp His Ser Leu Ser Cys Val Val Thr Pro Gln Asp Gly Glu
        690                 695                 700

Thr Ser Ala Gln Met Ile Glu Glu Asn Leu Asn Cys Leu Gly His Leu
705                 710                 715                 720

Ser Thr Ile Ile His Glu Ala Asn Glu Glu Gln Gly Asn Ser Met Met
                725                 730                 735

Asn Leu Asp Trp Ser Trp Leu Thr Glu
                740                 745

<210> SEQ ID NO 26
<211> LENGTH: 1173
<212> TYPE: PRT
<213> ORGANISM: Homo sapiens

<400> SEQUENCE: 26

Met Glu Glu Leu Ser Ala Asp Glu Ile Arg Arg Arg Leu Ala Arg
1               5                   10                  15

Leu Ala Gly Gly Gln Thr Ser Gln Pro Thr Thr Pro Leu Thr Ser Pro
            20                  25                  30

Gln Arg Glu Asn Pro Pro Gly Pro Pro Ile Ala Ala Ser Ala Pro Gly
        35                  40                  45

Pro Ser Gln Ser Leu Gly Leu Asn Val His Asn Met Thr Pro Ala Thr
    50                  55                  60

Ser Pro Ile Gly Ala Ser Gly Val Ala His Arg Ser Gln Ser Ser Glu
65                  70                  75                  80

Gly Val Ser Ser Leu Ser Ser Pro Ser Asn Ser Leu Glu Thr Gln
                85                  90                  95

Ser Gln Ser Leu Ser Arg Ser Gln Ser Met Asp Ile Asp Gly Val Ser
            100                 105                 110

Cys Glu Lys Ser Met Ser Gln Val Asp Val Asp Ser Gly Ile Glu Asn
        115                 120                 125

Met Glu Val Asp Glu Asn Asp Arg Arg Glu Lys Arg Ser Leu Ser Asp
    130                 135                 140

Lys Glu Pro Ser Ser Gly Pro Glu Val Ser Glu Glu Gln Ala Leu Gln
145                 150                 155                 160

Leu Val Cys Lys Ile Phe Arg Val Ser Trp Lys Asp Arg Asp Arg Asp
                165                 170                 175

Val Ile Phe Leu Ser Ser Leu Ser Ala Gln Phe Lys Gln Asn Pro Lys
            180                 185                 190

Glu Val Phe Ser Asp Phe Lys Asp Leu Ile Gly Gln Ile Leu Met Glu
        195                 200                 205

Val Leu Met Met Ser Thr Gln Thr Arg Asp Glu Asn Pro Phe Ala Ser
    210                 215                 220

Leu Thr Ala Thr Ser Gln Pro Ile Ala Ala Ala Arg Ser Pro Asp
225                 230                 235                 240

Arg Asn Leu Leu Leu Asn Thr Gly Ser Asn Pro Gly Thr Ser Pro Met
                245                 250                 255

Phe Cys Ser Val Ala Ser Phe Gly Ala Ser Ser Leu Ser Leu Gly
            260                 265                 270
```

-continued

```
Ala Ser Gly Gly Ala Ser Asn Trp Asp Ser Tyr Ser Asp His Phe Thr
            275                 280                 285
Ile Glu Thr Cys Lys Glu Thr Asp Met Leu Asn Tyr Leu Ile Glu Cys
        290                 295                 300
Phe Asp Arg Val Gly Ile Glu Glu Lys Ala Pro Lys Met Cys Ser
305                 310                 315                 320
Gln Pro Ala Val Ser Gln Leu Leu Ser Asn Ile Arg Ser Gln Cys Ile
                325                 330                 335
Ser His Thr Ala Leu Val Leu Gln Gly Ser Leu Thr Gln Pro Arg Ser
            340                 345                 350
Leu Gln Gln Pro Ser Phe Leu Val Pro Tyr Met Leu Cys Arg Asn Leu
        355                 360                 365
Pro Tyr Gly Phe Ile Gln Glu Leu Val Arg Thr Thr His Gln Asp Glu
    370                 375                 380
Glu Val Phe Lys Gln Ile Phe Ile Pro Ile Leu Gln Gly Leu Ala Leu
385                 390                 395                 400
Ala Ala Lys Glu Cys Ser Leu Asp Ser Asp Tyr Phe Lys Tyr Pro Leu
                405                 410                 415
Met Ala Leu Gly Glu Leu Cys Glu Thr Lys Phe Gly Lys Thr His Pro
            420                 425                 430
Val Cys Asn Leu Val Ala Ser Leu Arg Leu Trp Leu Pro Lys Ser Leu
        435                 440                 445
Ser Pro Gly Cys Gly Arg Glu Leu Gln Arg Leu Ser Tyr Leu Gly Ala
    450                 455                 460
Phe Phe Ser Phe Ser Val Phe Ala Glu Asp Asp Val Lys Val Val Glu
465                 470                 475                 480
Lys Tyr Phe Ser Gly Pro Ala Ile Thr Leu Glu Asn Thr Arg Val Val
                485                 490                 495
Ser Gln Ser Leu Gln His Tyr Leu Glu Leu Gly Arg Gln Glu Leu Phe
            500                 505                 510
Lys Ile Leu His Ser Ile Leu Leu Asn Gly Glu Thr Arg Glu Ala Ala
        515                 520                 525
Leu Ser Tyr Met Ala Ala Val Val Asn Ala Asn Met Lys Lys Ala Gln
    530                 535                 540
Met Gln Thr Asp Asp Arg Leu Val Ser Thr Asp Gly Phe Met Leu Asn
545                 550                 555                 560
Phe Leu Trp Val Leu Gln Gln Leu Ser Thr Lys Ile Lys Leu Glu Thr
                565                 570                 575
Val Asp Pro Thr Tyr Ile Phe His Pro Arg Cys Arg Ile Thr Leu Pro
            580                 585                 590
Asn Asp Glu Thr Arg Val Asn Ala Thr Met Glu Asp Val Asn Asp Trp
        595                 600                 605
Leu Thr Glu Leu Tyr Gly Asp Gln Pro Pro Phe Ser Glu Pro Lys Phe
    610                 615                 620
Pro Thr Glu Cys Phe Phe Leu Thr Leu His Ala His Leu Ser Ile
625                 630                 635                 640
Leu Pro Ser Cys Arg Arg Tyr Ile Arg Arg Leu Arg Ala Ile Arg Glu
                645                 650                 655
Leu Asn Arg Thr Val Glu Asp Leu Lys Asn Asn Glu Ser Gln Trp Lys
            660                 665                 670
Asp Ser Pro Leu Ala Thr Arg His Arg Glu Met Leu Lys Arg Cys Lys
        675                 680                 685
Thr Gln Leu Lys Lys Leu Val Arg Cys Lys Ala Cys Ala Asp Ala Gly
```

-continued

```
            690              695              700
Leu Leu Asp Glu Ser Phe Leu Arg Arg Cys Leu Asn Phe Tyr Gly Leu
705                      710                             720

Leu Ile Gln Leu Leu Leu Arg Ile Leu Asp Pro Ala Tyr Pro Asp Ile
                    725                  730                 735

Thr Leu Pro Leu Asn Ser Asp Val Pro Lys Val Phe Ala Ala Leu Pro
                740                  745                  750

Glu Phe Tyr Val Glu Asp Val Ala Glu Phe Leu Phe Ile Val Gln
            755                  760                  765

Tyr Ser Pro Gln Ala Leu Tyr Glu Pro Cys Thr Gln Asp Ile Val Met
770                      775                  780

Phe Leu Val Val Met Leu Cys Asn Gln Asn Tyr Ile Arg Asn Pro Tyr
785                      790                  795              800

Leu Val Ala Lys Leu Val Glu Val Met Phe Met Thr Asn Pro Ala Val
                805                  810                  815

Gln Pro Arg Thr Gln Lys Phe Phe Glu Met Ile Glu Asn His Pro Leu
                820                  825                  830

Ser Thr Lys Leu Leu Val Pro Ser Leu Met Lys Phe Tyr Thr Asp Val
                835                  840                  845

Glu His Thr Gly Ala Thr Ser Glu Phe Tyr Asp Lys Phe Thr Ile Arg
850                      855                  860

Tyr His Ile Ser Thr Ile Phe Lys Ser Leu Trp Gln Asn Ile Ala His
865                      870                  875                  880

His Gly Thr Phe Met Glu Glu Phe Asn Ser Gly Lys Gln Phe Val Arg
                885                  890                  895

Tyr Ile Asn Met Leu Ile Asn Asp Thr Thr Phe Leu Leu Asp Glu Ser
                900                  905                  910

Leu Glu Ser Leu Lys Arg Ile His Glu Val Gln Glu Glu Met Lys Asn
                915                  920                  925

Lys Glu Gln Trp Asp Gln Leu Pro Arg Asp Gln Gln Ala Arg Gln
                930                  935                  940

Ser Gln Leu Ala Gln Asp Glu Arg Val Ser Arg Ser Tyr Leu Ala Leu
945                      950                  955                  960

Ala Thr Glu Thr Val Asp Met Phe His Ile Leu Thr Lys Gln Val Gln
                965                  970                  975

Lys Pro Phe Leu Arg Pro Glu Leu Gly Pro Arg Leu Ala Ala Met Leu
                980                  985                  990

Asn Phe Asn Leu Gln Gln Leu Cys Gly Pro Lys Cys Arg Asp Leu Lys
                995                  1000                 1005

Val Glu Asn Pro Glu Lys Tyr Gly Phe Glu Pro Lys Lys Leu Leu
        1010                 1015                 1020

Asp Gln Leu Thr Asp Ile Tyr Leu Gln Leu Asp Cys Ala Arg Phe
        1025                 1030                 1035

Ala Lys Ala Ile Ala Asp Asp Gln Arg Ser Tyr Ser Lys Glu Leu
        1040                 1045                 1050

Phe Glu Glu Val Ile Ser Lys Met Arg Lys Ala Gly Ile Lys Ser
        1055                 1060                 1065

Thr Ile Ala Ile Glu Lys Phe Lys Leu Leu Ala Glu Lys Val Glu
        1070                 1075                 1080

Glu Ile Val Ala Lys Asn Ala Arg Ala Glu Ile Asp Tyr Ser Asp
        1085                 1090                 1095

Ala Pro Asp Glu Phe Arg Asp Pro Leu Met Asp Thr Leu Met Thr
        1100                 1105                 1110
```

-continued

```
Asp Pro Val Arg Leu Pro Ser Gly Thr Ile Met Asp Arg Ser Ile
    1115            1120                1125

Ile Leu Arg His Leu Leu Asn Ser Pro Thr Asp Pro Phe Asn Arg
    1130            1135                1140

Gln Thr Leu Thr Glu Ser Met Leu Glu Pro Val Pro Glu Leu Lys
    1145            1150                1155

Glu Gln Ile Gln Ala Trp Met Arg Glu Lys Gln Asn Ser Asp His
    1160            1165                1170
```

METHOD OF SCREENING COMPOUND CAPABLE OF ACCELERATING OR INHIBITING APOPTOSIS, APOPTOSIS ACCELARATOR AND APOPTOSIS INHIBITOR

This application is a national stage application of PCT/JP05/05247, file Mar. 23, 2005, which claims priority benefit under Title 35, United States Code, § 119(a)-(d) of Japanese Patent Application Nos. 2004-093266 and 2004-176107 filed on Mar. 26, 2004 and Jun. 14, 2004, respectively, in the Japan Patent Office, and the disclosures of which are herein incorporated by reference in their entirety.

TECHNICAL FIELD

The present invention relates to methods for screening pro- or anti-apoptotic compounds, apoptosis enhancers and apoptosis inhibitors.

BACKGROUND ART

In contrast to pro-apoptotic p53 and its homologue p73, the NF-κB signaling pathway plays an important role in cytoprotection against various pro-apoptotic stimuli such as DNA damage. Under normal conditions, NF-κB exists as heterodimeric complexes composed of p50 and p65 (RelA) subunits and is in the transcriptionally inactive state through interaction with inhibitory proteins such as IκB-α and IκB-β. IκB masks the nuclear localization signal of NF-κB and thereby inhibits NF-κB nuclear translocation.

On certain stimuli, an IκB kinase (IKK) complex, an upstream regulator of the NF-κB signaling pathway, rapidly phosphorylates particular serine residues located in the N-terminal signal response domain of IκB, which is then polyubiquitinated and degraded in a proteasome-dependent manner. As a result, the nuclear localization signal of NF-κB masked by IκB is exposed, leading to the nuclear translocation and subsequent activation of NF-κB. The IKK complex is composed of two catalytic subunits IKK-α (also called IKK-1) and IKK-β (also called IKK-2) and one regulatory subunit IKK-γ (also called NEMO) with a scaffold function.

The relationship between NF-κB and p53 or p73 has been characterized as follows: in response to a primary antigenic stimulation, NF-κB limits the up-regulation of pro-apoptotic p73 in T cells and promotes T cell survival, and however, the precise molecular basis by which the activation of NF-κB inhibits p73 expression is still unknown (Non-Patent Document 1). In response to an anticancer agent doxorubicin, IKK-β, but not IKK-α, activates NF-κB and thereby inhibits the accumulation of p53 at protein levels (Non-Patent Document 2). These results suggest that the activation of NF-κB might suppress apoptosis mediated by p53, p73, or both. In agreement with this suggestion, the presence of bidirectional repression between p53 and NF-κB has been shown (Non-Patent Document 3).

By contrast, it has been reported that NF-κB works as a cofactor of p53 and is required for p53-dependent apoptosis (Non-Patent Document 4). Besides, it has been shown that p53 is a direct transcriptional target of NF-κB, and that the p53-activating signal is partially blocked by the inhibition of NF-κB activation (Non-Patent Documents 5 to 7).

UFD2a (ubiquitin fusion degradation protein-2a), a member of the U-box ubiquitin protein ligase family, was originally identified as an E4 ubiquitination factor. UFD2a catalyzes polyubiquitin chain elongation and allows proteasomal degradation to target the polyubiquitinated substrate protein (Non-Patent Documents 8 and 9). The predicted three-dimensional structure of the U box is similar to that of the RING finger, and UFD2a also acts as E3 ubiquitin protein ligase (Non-Patent Document 9). It has recently been demonstrated that human UFD2a genes are located at the locus 1p36.2-p36.3 of candidate tumor suppressor genes for neuroblastoma and other cancers (Non-Patent Document 10). However, mutation analysis conducted by the present inventors has suggested UFD2a genes are rarely mutated in neuroblastoma and neuroblastoma-derived cell lines. In yeast, Ufd2 is associated with cell survival under stress conditions (Non-Patent Document 8). Through apoptotic stimulation, UFD2a is cleaved by caspase 6 or granzyme B and thereby exhibits remarkably impaired enzyme activity (Non-Patent Document 11).

[Non-Patent Document 1]: Wan, Y. Y. et al., The survival of antigen-stimulated T cells requires NF-κB-mediated inhibition of p73 expression. Immunity 18: 331-342 (2003).

[Non-Patent Document 2]: Tergaonkar, V. et al., p53 stabilization is decreased upon NF-κB activation: a role for NF-κB in acquisition of resistance to chemotherapy. Cancer Cell 1: 493-503 (2002).

[Non-Patent Document 3]: Webster, G. A. et al, Transcriptional crosstalk between NF-κB and p53. Mol. Cell. Biol. 19: 3485-3495 (1999).

[Non-Patent Document 4]: Ryan, K. M. et al., Role of NF-κB in p53-mediated programmed cell death. Nature 404: 892-897 (2000).

[Non-Patent Document 5]: Wu, H. et al, NF-κB activation of p53. A potential mechanism for suppressing cell growth in response to stress. J. Biol. Chem. 269: 20067-20074 (1994).

[Non-Patent Document 6]: Sun, X. et al., Identification of a novel p53 promoter element involved in genotoxic stress-inducible p53 gene expression. Mol. Cell. Biol. 15: 4489-4496 (1995).

[Non-Patent Document 7]: Hellin, A. C. et al., Nuclear factor-κB-dependent regulation of p53 gene expression induced by daunomycin genotoxic drug. Oncogene 16: 1187-1195 (1998).

[Non-Patent Document 8]: Koegl, M. et al., Cell 96; 635-644 (1999).

[Non-Patent Document 9]: Hatakeyama, H. et al., J. Biol. Chem. 276: 33111-33120 (2001).

[Non-Patent Document 10]: Ohira, M. et al., Oncogene 19: 4302-4307 (2000).

[Non-Patent Document 11]: Mahoney, J. A. et al., Biochem. J. 351: 587-595 (2002).

DISCLOSURE OF THE INVENTION

Problems to be Solved by the Invention

However, the functional importance of possible relationship between the NF-κB signaling pathway and apoptosis mediated by p53, p73, or both has not been established yet. The elucidation of the apoptosis-inducing activity of p73 inclusive of its mechanism and the discovery of compounds enhancing or inhibiting it lead to the development of therapeutic or preventive drugs for cancer or neurodegenerative disease.

Thus, one object of the present invention is to elucidate the molecular mechanism of p73 activation. Another object of the present invention is to provide methods for screening pro- or anti-apoptotic compounds that are derived from the mechanism.

Means for Solving the Problems

The present inventors have found that cisplatin treatment remarkably accumulates IKK-α in the nucleus in relation to the induction of p73 and p53. The present inventors have also found that IKK-α expression increases the half-life of p73 by inhibiting its ubiquitination, and thereby enhances transactivation and pro-apoptotic activity. From immunoprecipitation and immunostaining experiments, the present inventors have further found that p73, which directly associates with IKK-α, coexists with IKK-α in the nuclear matrix. Based on these findings, the present inventors have completed the present invention by elucidating a molecular mechanism where IKK-α stabilizes p73 through its direct interaction with p73 and promotes apoptosis induced by p73.

Namely, the present invention provides a method for screening a pro-apoptotic compound comprising a determination step of determining a compound enhancing interaction between p73 and IKK-α as a pro-apoptotic compound. This screening method is based on the molecular mechanism of direct interaction between p73 and IKK-α. This molecular mechanism was newly found by the present inventors. Thus, a pro-apoptotic compound with a new and totally different mechanism of action can be obtained by this screening method. The compound may be applied to an apoptosis enhancer or anticancer agent.

The present invention also provides a method for screening a pro-apoptotic compound comprising: a culture step of culturing cells expressing p73 and IKK-α under respective conditions of being in the presence of and in the absence of a test compound; an assay step of assaying the interactions between p73 and IKK-α in the respective cultured cells; and a determination step of determining the test compound as a pro-apoptotic compound, where the interaction between p73 and IKK-α in the cell cultured in the presence of the test compound is stronger than the interaction between p73 and IKK-α in the cell cultured in the absence of the test compound. A pro-apoptotic compound with a new and totally different mechanism of action can be obtained by this screening method. The compound may be applied to an apoptosis enhancer or anticancer agent.

The present invention also provides a method for screening an anti-apoptotic compound comprising a determination step of determining a compound inhibiting interaction between p73 and IKK-α as an anti-apoptotic compound. This screening method is based on the molecular mechanism of direct interaction between p73 and IKK-α. This molecular mechanism was newly found by the present inventors. Thus, an anti-apoptotic compound with a new and totally different mechanism of action can be obtained by this screening method. The compound may be applied to an apoptosis inhibitor or therapeutic drug for neurodegenerative disease.

The present invention also provides a method for screening an anti-apoptotic compound comprising: a culture step of culturing cells expressing p73 and IKK-α under respective conditions of being in the presence of and in the absence of a test compound; an assay step of assaying the interactions between p73 and IKK-α in the respective cultured cells; and a determination step of determining the test compound as an anti-apoptotic compound, where the interaction between p73 and IKK-α in the cell cultured in the presence of the test compound is weaker than the interaction between p73 and IKK-α in the cell cultured in the absence of the test compound. An anti-apoptotic compound with a new and totally different mechanism of action can be obtained by this screening method. The compound may be applied to an apoptosis inhibitor or therapeutic drug for neurodegenerative disease.

The present invention also provides an apoptosis enhancer comprising a protein comprising the amino acid sequence set forth in SEQ ID NO: 24, and an apoptosis enhancer comprising a nucleic acid encoding a protein comprising the amino acid sequence set forth in SEQ ID NO: 24. The protein comprising the amino acid sequence set forth in SEQ ID NO: 24 is an IKK-α protein. As described above, the present inventors have elucidated the molecular mechanism by which IKK-α stabilizes p73 through its direct interaction with p73 and promotes apoptosis induced by p73. Such a molecular mechanism completely defies the expectations from the role of IKK-α in the NF-κB signaling pathway, which is an anti-apoptotic pathway. Namely, IKK-α plays a pro-apoptotic role, but not anti-apoptotic role, in apoptosis mediated by p73. Thus, the IKK-α protein or a nucleic acid encoding the protein may be used as an apoptosis enhancer.

The present invention also provides an apoptosis inhibitor comprising a protein comprising the amino acid sequence set forth in SEQ ID NO: 25, and an apoptosis inhibitor comprising a nucleic acid encoding a protein comprising the amino acid sequence set forth in SEQ ID NO: 25. The protein comprising the amino acid sequence set forth in SEQ ID NO: 25 is an IKK-α (K44A) protein derived from IKK-α with the 44th lysine residue substituted by an alanine residue. The present inventors have revealed that IKK-α (K44A) binds to, but does not stabilize p73 and inhibits apoptosis induced by p73. Namely, IKK-α (K44A) functions in an anti-apoptotic manner in apoptosis mediated by p73. Thus, the IKK-α (K44A) protein and a nucleic acid encoding the protein may be used as an apoptosis inhibitor.

The present invention further provides an apoptosis inhibitor comprising a protein comprising the amino acid sequence set forth in SEQ ID NO: 26, and an apoptosis inhibitor comprising a nucleic acid encoding a protein comprising the amino acid sequence set forth in SEQ ID NO: 26. The protein comprising the amino acid sequence set forth in SEQ ID NO: 26 is UFD2a protein. The present inventors have revealed that UFD2a degrades p73 and thereby reduces the apoptotic activity of p73. Namely, UFD2a functions in an anti-apoptotic manner in apoptosis mediated by p73. Thus, the UFD2a protein and a nucleic acid encoding the protein may be used as an apoptosis inhibitor.

Effect of the Invention

According to the screening method of the present invention, pro- and anti-apoptotic compounds with a new and totally different mechanism of action can be obtained. The discovery of such compounds allows for the development of drugs effective for the treatment and prevention of cancer or neurodegenerative disease.

BRIEF DESCRIPTION OF THE DRAWINGS

FIG. 20 is a graph showing the fold transcriptional activation of p53/p73-responsive promoters in p53-deficient H1299 cells transiently cotransfected with an expression plasmid encoding HA-p73α together with a luciferase reporter carrying a p53-responsive element derived from a p21$^{WAF1}$, Bax, or MDM2 promoter and with a Renilla luciferase plasmid (pRL-TK) in the presence or absence of varying amounts of pcDNA3-IKK-α.

FIG. 22 is a graph showing the fold transcriptional activation of p53/p73-responsive promoters in p53-deficient H1299 cells transiently cotransfected with an expression plasmid encoding p53 together with a luciferase reporter carrying a p53-responsive element derived from a p21$^{WAF1}$, Bax, or MDM2 promoter and with a Renilla luciferase plasmid (pRL-TK) in the presence or absence of varying amounts of pcDNA3-IKK-α.

FIG. 36 is a graph showing the proportion of apoptotic cells to H1299 cells transiently cotransfected with the given combinations of expression plasmids.

BEST MODE FOR CARRYING OUT THE INVENTION

Figure 1:
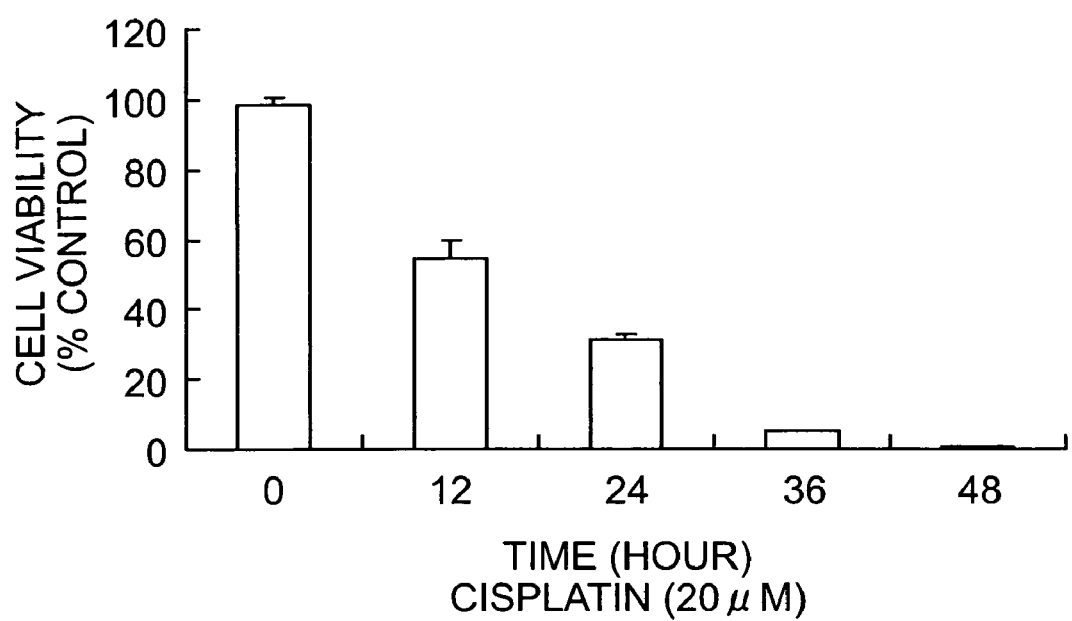
FIG. 1 is a graph showing the cell viability of osteosarcoma U2OS cells exposed to cisplatin.

Hereinafter, the preferable embodiments of the present invention will be described in detail.

(Methods for Screening Pro-Apoptotic Compound)

The method for screening a pro-apoptotic compound of the present invention comprises a determination step of determining a compound enhancing interaction between p73 and IKK-α as a pro-apoptotic compound. This screening method is based on the novel molecular mechanism of direct interaction between p73 and IKK-α and gives a pro-apoptotic compound with a new and totally different mechanism of action.

Assay systems for protein-protein interaction generally known by those skilled in the art are available as specific screening techniques, and examples thereof include yeast two-hybrid assay and PCA (protein-fragment complementation assay). The yeast two-hybrid assay and PCA are briefly described below.

First, the yeast two-hybrid assay is described. Yeast Gal4 is a transcriptional regulator composed of an N-terminal DNA-binding domain (DBD) and a C-terminal transcriptional activation domain (AD). Both domains autonomously function in principle. DBD can bind to DNA by itself but cannot activate transcription. AD is the converse. The yeast two-hybrid assay was developed by applying this property. Namely, a fusion protein (bait) of the protein P of interest with Gal4 DBD and a fusion protein (prey) of another protein Q with Gal4 AD are introduced into yeast cells. If the proteins P and Q interact with each other in the nucleus, a transcriptional regulation complex is reconstituted in the yeast cell, resulting in transcriptional activation dependent on a binding site for Gal4. The interaction between the proteins P and Q can be evaluated easily by detecting this activity with reporter genes. For example, HIS3, lacZ, and URA3 can be utilized as the reporter genes. In addition to yeast Gal4, a system using SRF or LexA is also available.

The screening method of the present invention may be performed by a system using p73 as the protein P and IKK-α as the protein Q (the converse is possible) in the yeast two-hybrid assay. Namely, yeasts are allowed to express either p73 or IKK-α as a bait and the other as a prey and cultured under respective conditions of being in the presence of and in the absence of a test compound. The respective transcriptional activities (which represent the intensity of interaction between p73 and IKK-α) of reporter genes in the cultured yeasts are assayed. The test compound can be determined as a pro-apoptotic compound, provided that the transcriptional activity in the presence of the test compound is larger than the transcriptional activity in the absence of the test compound.

Next, the PCA assay is described. In the PCA assay, one functional protein A (e.g., enzyme, transcriptional factor) is divided into two fragments A1 and A2, which are then fused with the proteins P and Q of interest, respectively to prepare fusion proteins A1-P and A2-Q. This assay is based on the principle where if the proteins P and Q of interest bind to each other, the functional protein A recovers its function, and the interaction between the proteins P and Q is determined by detecting the activity thereof. For example, β-lactamase can be utilized as the functional protein. The PCA assay using β-lactamase is described below.

β-lactamase is a β-lactam ring-cleaving enzyme derived from bacteria. This enzyme is divided into the N-terminal α197 fragment (25 to 197 residues) and the C-terminal ω198 fragment (198-288 residues), which are respectively expressed as fusion proteins with proteins of interest. Only in the presence of the binding of them, the β-lactamase protein recovers its three-dimensional structure and exhibits activity. The β-lactamase activity is detected with a cell-permeable fluorescent probe CCF2/AM (CCF2/acetoxymethyl ester). The CCF2/AM probe has a structure where two different fluorescent substances, coumarin and fluorescein, are bound with either end of a cephalosporin molecule, and exhibits intramolecular FRET (fluorescence resonance energy transfer) using the former as a donor and the latter as an acceptor. Namely, the excitation of coumarin with light of 409 nm results in the emission of fluorescence derived from fluorescein at 520 nm. However, if CCF2 is degraded by the β-lactamase activity, the donor and the acceptor dissociate from each other without FRET observed. Therefore, coumarin emits its original fluorescence at 447 nm by the excitation with light of 409 nm. The measurement of the fluorescence at 447 nm allows for the assay of the β-lactamase activity, that is, the intensity of interaction between the proteins of interest.

Thus, the screening method of the present invention utilizing the PCA assay may be performed by the following procedures: cells are allowed to express fusion proteins of two functional protein fragments A1 and A2 fused with either p73 or IKK-α and cultured under respective conditions of being in the presence of and in the absence of a test compound. The respective functional protein activities in the cultured cells are assayed. The test compound can be determined as a pro-apoptotic compound, provided that the functional protein activity in the cell cultured in the presence of the test compound is larger than the functional protein activity in the cell cultured in the absence of the test compound.

Moreover, the method for screening a pro-apoptotic compound of the present invention comprises: a culture step of culturing cells expressing p73 and IKK-α under respective conditions of being in the presence of and in the absence of a test compound; an assay step of assaying the interactions between p73 and IKK-α in the respective cultured cells; and a determination step of determining the test compound as a pro-apoptotic compound, where the interaction between p73 and IKK-α in the cell cultured in the presence of the test compound is stronger than the interaction between p73 and IKK-α in the cell cultured in the absence of the test compound. This screening method is based on the novel molecular mechanism of direct interaction between p73 and IKK-α and gives a pro-apoptotic compound with a new and totally different mechanism of action.

Assay systems for protein-protein interaction generally known by those skilled in the art are available as specific screening techniques, and examples thereof include immunoprecipitation. The screening method using the immunoprecipitation is described below.

At first, cells expressing p73 and IKK-α are prepared. Cells expressing both of them, cells expressing both of them as a result of transfecting cells expressing either of them with the other, and cells obtained by cotransfecting cells expressing neither of them with both of them can be used as the cells expressing p73 and IKK-α. Alternatively, cells allowed to express p73 by drug treatment such as cisplatin treatment may be used. The cells are cultured under respective conditions of in the presence of and in the absence of a test compound. A culture time may be any time that can bring about the interaction between p73 and IKK-α, and though differing depending on types of cells used, is approximately 12 to 48 hours, for example, for cells cotransfected with p73 and IKK-α.

Next, the interactions between p73 and IKK-α in the respective cultured cells are assayed. To assay the interaction, the cultured cells are first pulverized to prepare cell lysates. Although cell lysates from the whole cells may be used, it is preferred that cell lysates from nuclear fractions should be used because p73 and IKK-α interact with each other in the nucleus. An antibody against either p73 or IKK-α molecule is added to the prepared cell lysates to perform immunoprecipitation. Then, the obtained precipitate (which contains a complex of p73 and IKK-α) is subjected to an immunological approach (e.g., immunoblot) using an antibody against the other molecule, by which the interaction between p73 and IKK-α can be assayed by detecting and quantifying the complex of p73 and IKK-α.

As a result of the assay, the test compound is determined as being positive, provided that the interaction between p73 and IKK-α in the cell cultured in the presence of the test compound is stronger (the amount of the protein complex formed is larger) than that in the cell cultured in the absence of the test compound. Namely, the compound can be determined as a pro-apoptotic compound.

(Screening Methods for an Anti-Apoptotic Compound)

The method for screening an anti-apoptotic compound of the present invention comprises a determination step of determining a compound inhibiting interaction between p73 and IKK-α as an anti-apoptotic compound. This screening method is based on the novel molecular mechanism of direct interaction between p73 and IKK-α and gives an anti-apoptotic compound with a new and totally different mechanism of action.

Assay systems for protein-protein interaction generally known by those skilled in the art are available as specific screening techniques, and examples thereof include yeast two-hybrid assay and PCA (protein-fragment complementation assay). The general outlines of the yeast two-hybrid assay and PCA are the same as above.

This screening method utilizing the yeast two-hybrid assay is performed as follows: yeasts are allowed to express either p73 or IKK-α as a bait and the other as a prey and cultured under respective conditions of being in the presence of and in the absence of a test compound. The respective transcriptional activities (which represent the intensity of interaction between p73 and IKK-α) of reporter genes in the cultured yeasts are assayed. The test compound can be determined as an anti-apoptotic compound, provided that the transcriptional activity in the presence of the test compound is lower than the transcriptional activity in the absence of the test compound.

This screening method utilizing the PCA assay is performed as follows: cells are allowed to express fusion proteins of two functional protein fragments A1 and A2 fused with either p73 or IKK-α and cultured under respective conditions of being in the presence of and in the absence of a test compound. The respective functional protein activities in the cultured cells are assayed. The test compound can be determined as an anti-apoptotic compound, provided that the functional protein activity in the cell cultured in the presence of the test compound is lower than the functional protein activity in the cell cultured in the absence of the test compound.

The method for screening an anti-apoptotic compound of the present invention comprises: a culture step of culturing cells expressing p73 and IKK-α under respective conditions of being in the presence of and in the absence of a test compound; an assay step of assaying the interactions between p73 and IKK-α in the respective cultured cells; and a determination step of determining the test compound as an anti-apoptotic compound, where the interaction between p73 and IKK-α in the cell cultured in the presence of the test compound is weaker than the interaction between p73 and IKK-α in the cell cultured in the absence of the test compound. This screening method is based on the novel molecular mechanism of direct interaction between p73 and IKK-α and gives an anti-apoptotic compound with a new and totally different mechanism of action.

Assay systems for protein-protein interaction generally known by those skilled in the art are available as specific screening techniques, and examples thereof include immunoprecipitation. The screening method using the immunoprecipitation is performed in the same way as described above except for the step of determining the compound. Namely, the test compound is determined as being positive, provided that the interaction between p73 and IKK-α. in the cell cultured in the presence of the test compound is weaker (the amount of the protein complex formed is smaller) than that in the cell cultured in the absence of the test compound as a result of assay of the interaction between p73 and IKK-α. Namely, the compound can be determined as an anti-apoptotic compound.

(Apoptosis Enhancers)

An apoptosis enhancer of the present invention comprises a protein comprising the amino acid sequence set forth in SEQ ID NO: 24. The protein comprising the amino acid sequence set forth in SEQ ID NO: 24 represents an IKK-α protein. According to the molecular mechanism found by the present inventors, IKK-α stabilizes p73 through its direct interaction with p73 and promotes apoptosis induced by p73. Thus, this apoptosis enhancer is contacted with or administered to cells, tissues, or individuals, thereby allowing for the promotion of apoptosis for the cells, tissues, or individuals. This apoptosis enhancer is contacted with or administered to cancer cells, cancer tissues, or individuals suffering from cancer, thereby allowing for the suppression or treatment of cancer. Namely, the apoptosis enhancer may be used as an anticancer agent. For the contact or administration of the apoptosis enhancer, it is preferred to contact or administer it together with p73. This is because apoptosis is further promoted.

Moreover, an apoptosis enhancer of the present invention comprises a nucleic acid encoding a protein comprising the amino acid sequence set forth in SEQ ID NO: 24. Preferably, the apoptosis enhancer of the present invention is a nucleic acid comprising the nucleotide sequence set forth in SEQ ID NO: 23. According to the molecular mechanism found by the present inventors, IKK-α stabilizes p73 through its direct interaction with p73 and promotes apoptosis induced by p73. Thus, this apoptosis enhancer is incorporated into an appropriate vector, which is in turn contacted with or administered to cells, tissues, or individuals, thereby allowing for the promotion of apoptosis for the cells, tissues, or individuals. The vector is contacted with or administered to cancer cells, cancer tissues, or individuals suffering from cancer, thereby allowing for the suppression or treatment of cancer. Namely, the apoptosis enhancer may be used as an anticancer agent. For the contact or administration of the apoptosis enhancer, it is preferred to contact or administer it together with p73. This is because apoptosis is further promoted.

(Apoptosis Inhibitors)

An apoptosis inhibitor of the present invention comprises a protein comprising the amino acid sequence set forth in SEQ ID NO: 25. The protein comprising the amino acid sequence set forth in SEQ ID NO: 25 represents an IKK-α (K44A) protein derived from IKK-α with the 44th lysine residue substituted by an alanine residue. The present inventors have revealed that IKK-α (K44A) binds to, but does not stabilize, p73 and inhibits apoptosis induced by p73. Thus, this apoptosis inhibitor is contacted with or administered to cells, tissues, or individuals, thereby allowing for the inhibition of apoptosis for the cells, tissues, or individuals. This apoptosis inhibitor is contacted with or administered to cells or tissues undergoing apoptosis or individuals suffering from neurodegenerative disease, thereby allowing for the treatment of neurodegenerative disease. Namely, the apoptosis inhibitor may be used as a therapeutic agent for neurodegenerative disease. For the contact or administration of the apoptosis inhibitor, it is preferred to confirm p73 expression in cells, tissues, or individuals to be contacted or administered with the apoptosis inhibitor. This is because apoptosis can be inhibited with higher reliability.

Moreover, an apoptosis inhibitor of the present invention comprises a nucleic acid encoding a protein comprising the amino acid sequence set forth in SEQ ID NO: 25. The present inventors have revealed that IKK-α (K44A) binds to, but does not stabilize, p73 and inhibits apoptosis induced by p73. Thus, this apoptosis inhibitor is incorporated into an appropriate vector, which is in turn contacted with or administered to cells, tissues, or individuals, thereby allowing for the inhibition of apoptosis for the cells, tissues, or individuals. The vector is contacted with or administered to cells or cancer tissues undergoing apoptosis or individuals suffering from neurodegenerative disease, thereby allowing for the treatment of neurodegenerative disease. Namely, the apoptosis inhibitor may be used as a therapeutic agent for neurodegenerative disease. For the contact or administration of the apoptosis inhibitor, it is preferred to confirm p73 expression in cells, tissues, or individuals to be contacted or administered with the apoptosis inhibitor. This is because apoptosis can be inhibited with higher reliability.

An apoptosis inhibitor of the present invention comprises a protein comprising the amino acid sequence set forth in SEQ ID NO: 26. The protein comprising the amino acid sequence set forth in SEQ ID NO: 26 represents a UFD2a protein. The present inventors have revealed that UFD2a degrades p73, but not p53, and selectively inhibits apoptosis mediated by p73. Thus, this apoptosis inhibitor is contacted with or administered to cells, tissues, or individuals, thereby allowing for the inhibition of apoptosis for the cells, tissues, or individuals. This apoptosis inhibitor is contacted with or administered to cells or tissues undergoing apoptosis or individuals suffering from neurodegenerative disease, thereby allowing for the treatment of neurodegenerative disease. Namely, the apoptosis inhibitor may be used as a therapeutic agent for neurodegenerative disease. For the contact or administration of the apoptosis inhibitor, it is preferred to confirm p73 expression in cells, tissues, or individuals to be contacted or administered with the apoptosis inhibitor. This is because apoptosis can be inhibited with higher reliability.

Moreover, an apoptosis inhibitor of the present invention comprises a nucleic acid encoding a protein comprising the amino acid sequence set forth in SEQ ID NO: 26. The present inventors have revealed that UFD2a degrades p73, but not p53, and selectively inhibits apoptosis mediated by p73. Thus, this apoptosis inhibitor is incorporated into an appropriate vector, which is in turn contacted with or administered to cells, tissues, or individuals, thereby allowing for the inhibition of apoptosis for the cells, tissues, or individuals. The vector is contacted with or administered to cells or cancer tissues undergoing apoptosis or individuals suffering from neurodegenerative disease, thereby allowing for the treatment of neurodegenerative disease. Namely, the apoptosis inhibitor may be used as a therapeutic agent for neurodegenerative disease. For the contact or administration of the apoptosis inhibitor, it is preferred to confirm p73 expression in cells, tissues, or individuals to be contacted or administered with the apoptosis inhibitor. This is because apoptosis can be inhibited with higher reliability.

EXAMPLES

Hereinafter, the present invention will be described more fully with reference to Examples. However, the present invention is not intended to be limited to these Examples.

(Cell Culture and Transfection)

African green monkey liver COS7 cells and human osteosarcoma U2OS cells were cultured in Dulbecco's modified Eagle's medium (DMEM) containing 10% (v/v) heat-inactivated fetal bovine serum (FBS; Invitrogen) and penicillin (100 IU/mL)/streptomycin (100 μg/mL). Human lung carcinoma H1299 cells and mouse fibroblast L929 cells were cultured in RPMI1640 medium containing 10% heat-inactivated FBS and an antibiotic mixture. The resulting cultures were maintained at 37° C. under a water-saturated atmosphere of 5% $CO_2$.

To perform transient transfection, COS7 cells were cultured until 50% confluency and transfected with the given combinations of expression plasmids by use of FuGENE6 transfection reagent (Roche Molecular Biochemicals) according to the manufacturer's instruction. H1299 cells and U2OS cells were transfected with LipofectAMINE transfection reagent (Invitrogen) according to the manufacturer's instruction. pcDNA3 empty plasmid (Invitrogen) was used as a blank plasmid to balance the amount of DNA introduced by transient transfection.

(Cell Survival Assay)

U2OS cells were seeded at a density of $5\times10^3$ cells/well to a 96-well tissue culture dish supplemented with 100 μL of complete medium, and then allowed to adhere thereto overnight. A cisplatin stock solution was filtered and sterilized with a filter of 0.45 μm in pore size and diluted with phosphate-buffered saline (PBS). Cisplatin was added at the final concentration of 20 μM to the cultures, followed by cell viability assay. The viability was assayed by a modified 3-(4, 5-dimethylthiazol-2-yl)-2,5-diphenyl-tetrazolium bromide (MTT) assay at given time points after the cisplatin addition. The MTT assay was performed by adding 10 μL of MTT solution to each well and incubating the cultures at 37° C. for 1 hour. A microplate reader (Model 450; Bio-Rad) was used to measure the absorbance of each well at 570 nm.

(RNA Extraction and RT-PCR)

Total RNA was extracted from U2OS cells exposed to cisplatin (final concentration: 20 μM) by use of RNeasy Mini Kit (Qiagen) according to the manufacturer's protocol. Reverse transcription reaction was performed by mixing the total RNA (5 μg) with SuperScript II reverse transcriptase (Invitrogen) and random primers and incubating the mixture at 42° C. for 1 hour. After the completion of the reaction, cDNA was diluted with water and amplified with 15 μL of reaction solution (which contained 100 μM of each deoxynucleoside triphosphate, 1×PCR buffer, 1 μM of each primer, and 0.2 units of rTaq DNA polymerase (Takara Bio)).

The following oligonucleotide primers were used:

```
for IKK-α:
(forward, SEQ ID NO: 1)    5'-CCGACTTCAGCAGAACATGA-3'
(reverse, SEQ ID NO: 2)    5'-tggggacagtgaacaagtga-3' for IKK-β:
(forward, SEQ ID NO: 3)    5'-aaccagcatccagattgacc-3'
(reverse, SEQ ID NO: 4)    5'-ctctaggtcgtccagcgttc-3' for IKK-γ:
(forward, SEQ ID NO: 5)    5'-cctcactccctgtgaagctc-3'
(reverse, SEQ ID NO: 6)    5'-gagactcttcgcccagtacg-3'
```

-continued

```
for IκB-α:
(forward, SEQ ID NO: 7)   5'-gcaaaatcctgacctggtgt-3'
(reverse, SEQ ID NO: 8)   5'-gctcgtcctctgtgaactcc-3' for p53:
(forward, SEQ ID NO: 9)   5'-ATTTGATGCTGTCCCCGGACGAT
                             ATTGAAC-3'
(reverse, SEQ ID NO: 10)  5'-ACCCTTTTTGGACTTCAGGTGGC
                             TGGAGTG-3' for p73α
(forward, SEQ ID NO: 11)  5'-CCGGGAGAACTTTGAGATCC-3'
(reverse, SEQ ID NO: 12)  5'-ATCTTCAGGGCCCCCAGGTC-3' for p21^{WAF1}:
(forward, SEQ ID NO: 13)  5'-CCGGGAGAACTTTGAGATCC-3'
(reverse, SEQ ID NO: 14)  5'-ATCTTCAGGGCCCCCAGGTC-3' for Bax:
(forward, SEQ ID NO: 15)  5'-tttgcttcagggtttcatcc-3'
(reverse, SEQ ID NO: 16)  5'-cagttgaagttgccgtcaga-3' for GAPDH:
(forward, SEQ ID NO: 17)  5'-ACCTGACCTGCCGTCTAGAA-3'
(reverse, SEQ ID NO: 18)  5'-TCCACCACCCTGTTGCTGT
                             A-3'.
```

GAPDH expression was assayed and used as an internal standard. The PCR amplification products were separated by electrophoresis with 1.5% agarose gel in TAE buffer (40 mM Tris-Cl, 1 mM EDTA) and visualized with ethidium bromide (post-staining).

(FLAG Epitope for Tagging IKK-α)

IKK-α was epitope-tagged at the N terminus with a FLAG epitope and subcloned into a pcDNA3 expression plasmid. To obtain an expression plasmid for FLAG-tagged IKK-α, the coding region of IKK-α was amplified by PCR. The following oligonucleotide primers were used in the PCR:

```
(forward, SEQ ID NO: 19)  5'-ccggaattcgagcggccccggg
                             gctgcggc-3'
(reverse, SEQ ID NO: 20)  5'-ccgctcgagcggtcattctgcta
                             accaactccaatcaagactcat-3'.
```

The underlined nucleotides of the forward primer represent an EcoRI cleavage site, and the underlined nucleotides of the reverse primer represent an XhoI cleavage site. The PCR products were completely digested with EcoRI and XhoI and introduced into the identical cleavage sites of the pcDNA3-FLAG expression plasmid in-frame to the downstream of the FLAG tag. The resulting expression plasmid encodes the full-length IKK-α tagged with the FLAG epitope (pcDNA-FLAG-IKK-α). The construct was confirmed by restriction enzyme digestion and DNA sequencing.

(Preparation of IKK-α Mutant Lacking Kinase Activity)

K44A mutation was introduced into wild-type IKK-α by use of PfuUltra™ High-Fidelity DNA polymerase (Stratagene) according to the manufacturer's instruction. The following oligonucleotide primers were used: 5'-GCGTCTTGTCGTTTAGAGCTAAGTTCCAAAAACAGA GAGCG ATGGTGCCAT-3' (forward, SEQ ID NO: 21; the underlined portion encodes the 44th amino acid Ala)

```
(reverse, SEQ ID NO: 22)  5'-AATTGCTATTTTGAGATCAAGTT
                             CCCGGTGCTGGTACAGACTGACGTTC
                             CC-3'.
```

The PCR products were self-ligated in the presence of T4 DNA ligase (Takara Bio), and their nucleotide sequences were determined to confirm the presence of the intended mutation and the absence of random mutation.

(Immunoblot)

Cells were transiently transfected with a total of 2 μg of expression plasmids. After 48 hours of the transfection, the cells were washed with ice-cold PBS and suspended in lysis buffer (pH 8.0; which contained 25 mM Tris-Cl, 137 mM sodium chloride, 1% Triton X-100, 1 mM phenylmethylsulfonyl fluoride (PMSF), and protease inhibitor mix (Roche Molecular Biochemicals)), followed by brief sonication. After centrifugation at 15000 rpm for 10 minutes, the supernatant was collected and assayed for protein concentrations by the Bradford assay (Bio-Rad). Equal amounts of lysates (protein amount: 50 μg) from the whole cells were denatured by boiling in Laemmli SDS-sample buffer, then separated on 10% SDS-polyacrylamide gel (SDS-PAGE), and transferred at room temperature for 1 hour to polyvinylidene difluoride (PVDF) membranes (Immobilon-P; Millipore) in Tris-glycine buffer containing 10% methanol. The membranes were blocked at room temperature for 1 hour with Tris-buffered saline (TBS-T) containing 5% skim milk and 0.1% Tween 20.

Then, the membranes were reacted with an anti-FLAG monoclonal (M2; Sigma), anti-HA monoclonal (12CA5; Roche Molecular Biochemicals), anti-p73 monoclonal (Ab-4; NeoMarkers), anti-p53 monoclonal (DO-1; Oncogene Research Products), anti-Bax monoclonal (6A7; eBioscience), anti-IKK-α polyclonal (M-280; Santa Cruz Biotechnology), anti-IKK-β polyclonal (H-470; Santa Cruz Biotechnology), anti-IKK-γ polyclonal (FL-417; Santa Cruz Biotechnology), anti-p65 polyclonal (C-20; Santa Cruz Biotechnology), anti-IκB-α polyclonal (C-21; Santa Cruz Biotechnology), anti-actin polyclonal (20-33, Sigma), or anti p21$^{WAF1}$ polyclonal (H-164; Santa Cruz Biotechnology) antibody used as a primary antibody. After the reaction with the primary antibody, the membranes were reacted at room temperature for 1 hour with a horseradish peroxidase (HRP)-labeled goat anti-mouse or anti-rabbit secondary antibody (Cell Signaling Technologies) diluted 2000-fold in TBS-T. Immunoreactive proteins were finally visualized by use of an enhanced chemiluminescence system (ECL; Amersham Pharmacia Biotech) according to the manufacturer's instruction.

(Subcellular Fraction)

To prepare nuclear and cytoplasmic extracts, cells were washed with ice-cold PBS and suspended in lysis buffer (pH 7.5; which contained 10 mM Tris-Cl, 1 mM EDTA, 0.5% Nonidet P-40 (NP-40), 1 mM PMSF, and protease inhibitor mix (Sigma)). The suspended cells were incubated at 4° C. for 30 minutes and centrifuged at 5000 rpm for 10 minutes to collect soluble fractions (which were used as cytoplasmic extracts). Insoluble fractions were washed with lysis buffer and dissolved in 1×Laemmli SDS-sample buffer (pH 6.8; which contained 62.5 mM Tris-Cl, 2% SDS, 2% β-mercaptoethanol, and 0.01% bromophenol blue) to collect nuclear extracts. The nuclear and cytoplasmic fractions were subjected to immunoblot analysis using an anti-lamin B monoclonal (Ab-1; Oncogene Research Products) or anti-α-tubulin monoclonal (DM1A; Cell Signaling Technology) antibody.

(Proteolytic Rate Analysis)

COS7 cells were transiently transfected with a HA-p73α expression plasmid together with or without an IKK-α expression plasmid. The cells were collected at given time points after pretreatment with cycloheximide (final concentration: 100 μg/μL). Lysates from the whole cells were prepared and subjected to immunoblot analysis using an anti-p73 monoclonal or anti-actin polyclonal antibody. Densitometry was used to quantify the amount of HA-p73α normalized to actin.

(Ubiquitination Assay)

COS7 cells were transiently transfected with a constant amount of expression plasmids encoding HA-p73α and HA-Ub in the presence or absence of varying amounts of IKK-α expression plasmids. After 4 hours from the transfection, the cells were exposed for 6 hours to a proteasome inhibitor MG-132 (final concentration: 20 μM), and lysates from the whole cells were first subjected to immunoprecipitation with an anti-p73 monoclonal antibody and then to immunoblot using an anti-HA monoclonal antibody (12CA5; Roche Molecular Biochemicals) to analyze ubiquitination levels.

(Immunoprecipitation Analysis)

Whole cell lysates were centrifuged at 15000 rpm for 15 minutes to remove cell debris. The obtained supernatant was pretreated at 4° C. for 30 minutes with protein G-Sepharose (50% slurry, 30 μL; Amersham Pharmacia Biotech). After centrifugation, the supernatant was incubated at 4° C. for 2 hours with an anti-HA polyclonal (Medical and Biological Laboratories) or anti-FLAG monoclonal antibody. The immunocomplexes were precipitated at 4° C. for 30 minutes with protein G-Sepharose beads. After collection by brief centrifugation, the immunoprecipitates were washed three times with lysis buffer, then suspended in 30 μL of 2×Laemmli SDS sample buffer, and treated at 100° C. for 5 minutes. The supernatant was loaded onto 10% SDS-PAGE and analyzed by immunoblot as described above.

(GST Pull-Down Assay)

Whole cell lysates prepared from COS7 cells expressing FLAG-IKK-α were mixed with glutathione S-transferase (GST) or GST fusion protein and incubated with slow shaking at 4° C. for 2 hours in the presence of glutathione-Sepharose beads (Amersham Pharmacia Biotech). Then, the Sepharose beads were precipitated by brief centrifugation and vigorously washed with NETN buffer (pH 7.5; 50 mM Tris-Cl, 150 mM sodium chloride, 0.1% NP-40, and 1 mM EDTA) containing 1 mM PMSF. The proteins bound with the beads were eluted therefrom by the addition of 30 μL of 2×Laemmli SDS sample buffer, then boiled for 5 minutes, and separated with 10% SDS-PAGE. The proteins were transferred to PVDF membranes and immunoblotted with FLAG-IKK-α as described above.

(Immunofluorescence Analysis)

U2OS cells were cultured on coverslips and transfected with given expression plasmids. After 48 hours from the transfection, the cells were washed with ice-cold PBS and fixed at −20° C. for 20 minutes in 100% methanol. The cells were washed twice with PBS and blocked at room temperature for 1 hour with a PBS solution (which contained 0.1% glycine and 0.1% sodium azide) containing 3% bovine serum albumin (BSA). Then, the cells were washed with PBS and incubated at room temperature for 1 hour by simultaneously using 50-fold diluted anti-lamin B monoclonal and 200-fold diluted anti-FLAG polyclonal (Sigma) antibodies. To detect bound immunoglobulin, the cells were incubated at room temperature for 1 hour with a rhodamine- or fluorescein isothiocyanate (FITC)-labeled secondary antibody (Invitrogen) diluted 200-fold. After the incubation with the secondary antibody, the coverslips were washed with PBS, then mounted onto glass slides by use of Fluoromount-G (Southern Biotech), and examined with a laser scanning confocal microscope (Olympus).

(Luciferase Reporter Assay)

H1299 cells deficient in p53 were seeded at a density of 5×10$^4$ cells/well onto a 12-well tissue culture dish and transiently transfected with 100 ng of luciferase reporter construct (which carried a p53/p73-responsive element derived from a p21$^{WAF1}$, Bax, or MDM2 promoter), 10 ng of pRL-TK Renilla luciferase cDNA, and 25 ng of given expression plasmid (p53, HA-p73α, or HA-p73β) together with or without varying amounts of IKK-α or FLAG-IKK-β expression plasmids. The total amount of DNA per transfection was kept constant (510 ng) with a pcDNA3 empty plasmid. After 48 hours from the transfection, the cells were washed twice with ice-cold PBS and suspended in passive lysis buffer (Promega). Both firefly and Renilla luciferase activities were assayed by use of dual-luciferase reporter assay system (Promega) according to the instruction. Fluorescence intensity was measured with TD-20 luminometer (Turner Design). The firefly luciferase signal was normalized based on the Renilla luciferase signal. Results obtained from at least 3 transfections were indicated by mean value±standard deviation.

(Apoptosis Assay)

To detect apoptosis via p73α and IKK overexpression, H1299 cells were seeded at a density of 1.5×10$^4$ cells/well onto a 6-well tissue culture dish. Next day, the cells were transiently transfected with 50 ng of β-galactosidase expression plasmid and 50 ng of HA-p73α expression plasmid in the presence or absence of varying amounts of IKK-α or IKK-β expression vectors (100, 200, or 400 ng). After 48 hours of the transfection, the cells were washed with ice-cold PBS and stained at room temperature for 10 minutes with 0.4% trypan blue (PBS solution). Then, the cells were washed twice with PBS, then fixed for 10 minutes in PBS containing 2.5% glutaraldehyde, 1 mM magnesium chloride, and 2 mM EGTA, and stained for 2 hours with Red-Gal (Research Organics) according to the method described in Bayon, Y. et al., Mol. Cell. Biol. 23: 1061-1074 (2003). Red-Gal was used as a marker for visualizing the transfected cells to evaluate the degree of apoptosis occurring in the transfectants. Apoptotic cells were scored by gathering the cells exhibiting dark pink-purple color due to the double staining with Red-Gal and trypan blue. Results were indicated by an average of three independent transfections (each performed three times or more).

Example 1

Induction of IKK-α During Cisplatin-Mediated Apoptosis in U2OS Cells

Figure 2:
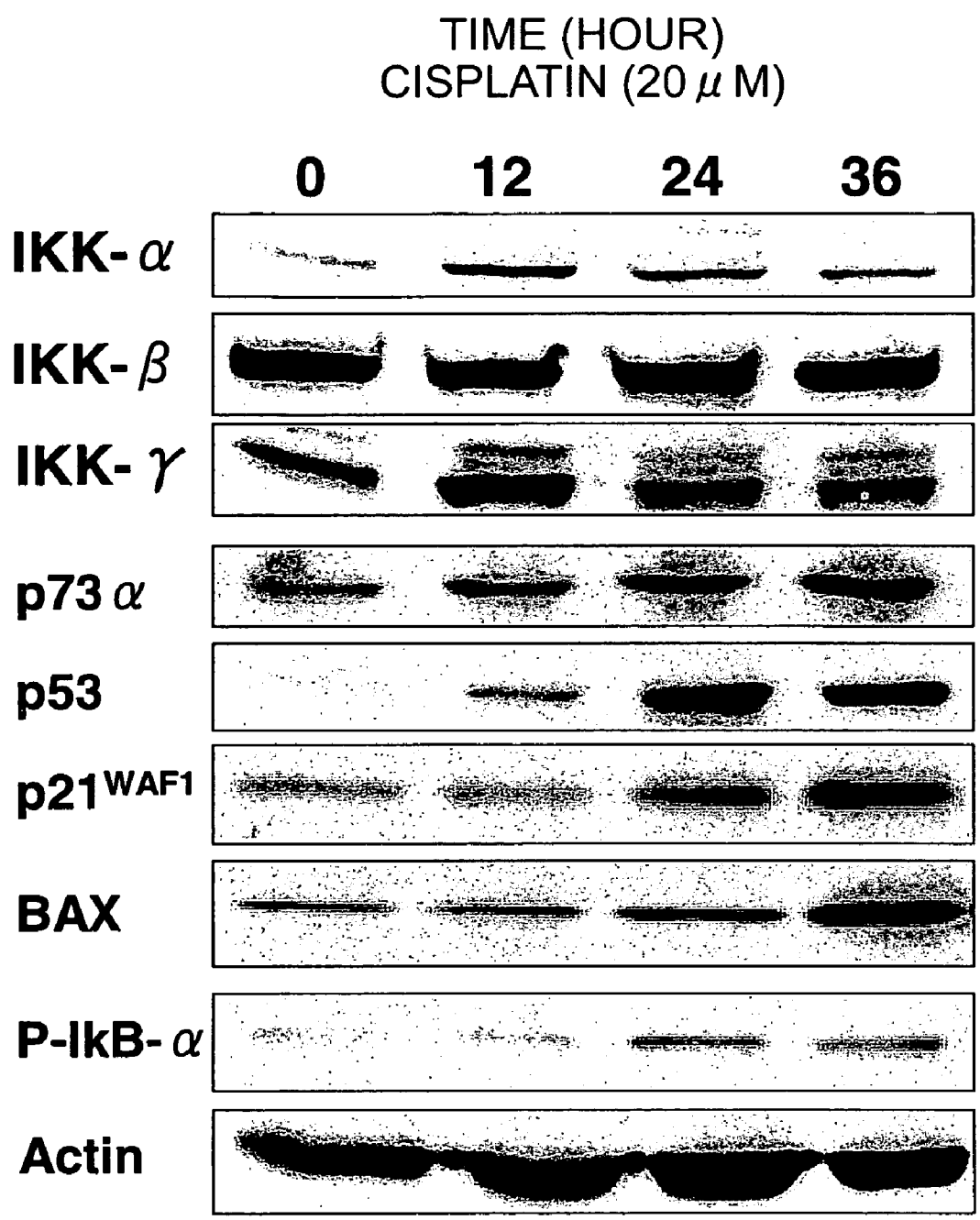
FIG. 2 is a diagram showing a result of immunoblot of cell lysates of U2OS cells treated with cisplatin.
Figure 3:
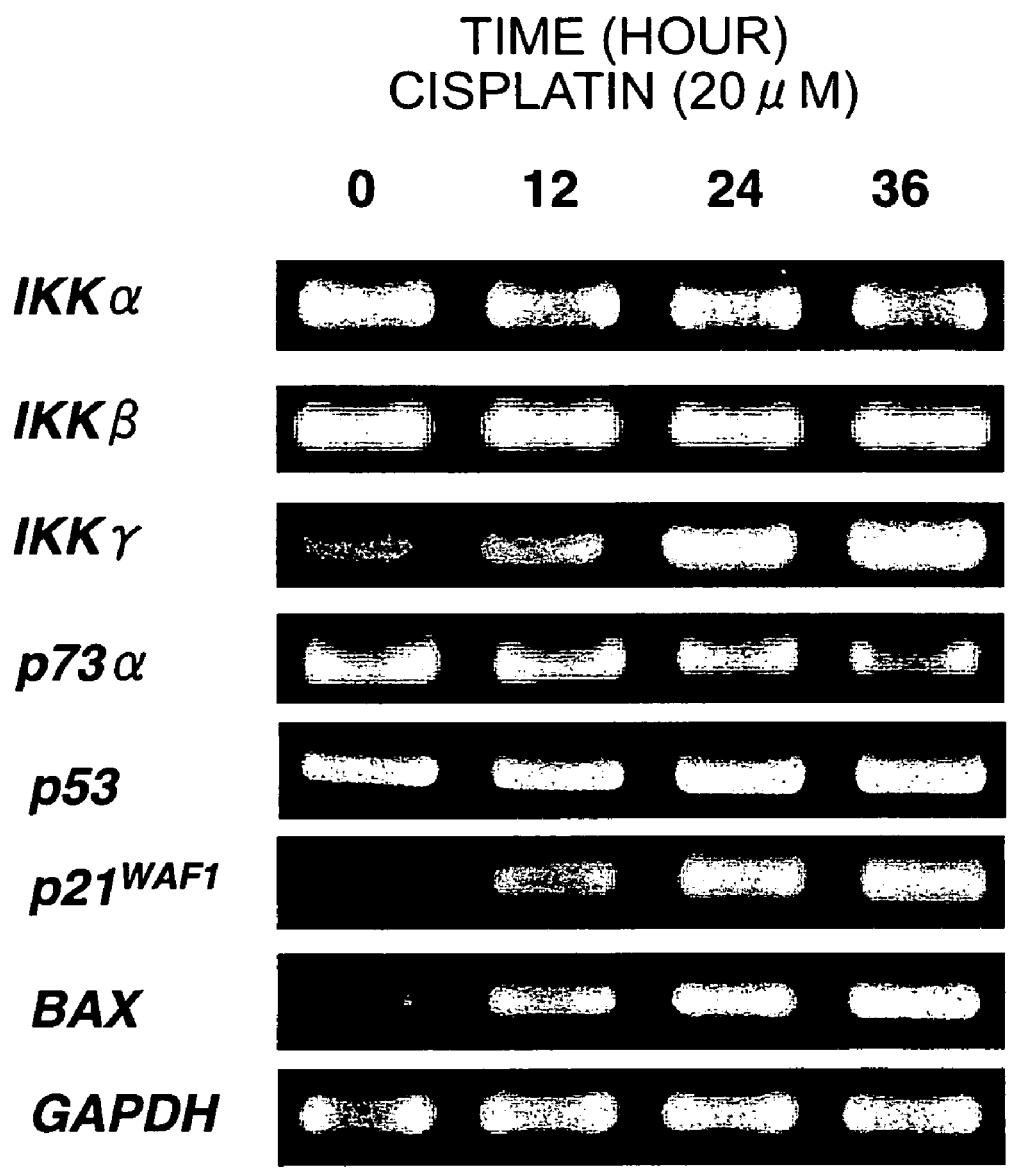
FIG. 3 is a diagram showing a result of RT-PCR analysis of RNA from U2OS cells treated with cisplatin.

To define potential function(s) of IκB kinases (IKKs) in signaling induced by DNA damage, their protein and mRNA expression levels were examined by exposing U2OS cells to a DNA-damaging chemotherapeutic agent cisplatin. The U2OS cells, when examined by cell survival assay, underwent apoptosis in a time-dependent manner (FIG. 1). In immunoblot analysis, p53 and its homologue p73α (both are main mediators in DNA damage response (Melino, G. et al., Nat. Rev. Cancer 2: 605-615 (2002); and Vousden, K. H. et al., Nat. Rev. Cancer 2: 594-604 (2002)) were remarkably induced at protein levels in response to cisplatin (FIG. 2). On the other hand, the expression of p53 and p73α mRNAs was not induced (FIG. 3). Their accumulation was associated with downstream effectors such as p21$^{WAF1}$ and Bax. Particularly, cisplatin treatment remarkably accumulated IKK-α, and its induction was observed during the period from 12 to 36 hours after the cisplatin exposure (FIG. 2). After 12 hours of cisplatin treatment, an IKK-γ (NEMO) protein level was transiently increased, while the IKK-γ level was decreased by the extension of cisplatin treatment time to 24 to 36 hours and was almost indistinguishable from that of untreated cells. By contrast, cisplatin treatment hardly changed the amount of IKK-β. As a result of RT-PCR analysis, the expression of IKK-α and IKK-β mRNAs was not changed by cisplatin treatment, whereas remarkable increase in the expression level of IKK-γ mRNA was observed in a time-dependent manner in response to cisplatin treatment (FIG. 3). Interestingly, the result of immunoblot analysis shows that cisplatin treatment remarkably increased the phosphorylated form of IκB-α (well characterized substrate for IKK complexes).

Taken together, these results suggested that the accumulation of p53 and p73 induced by DNA damage is associated with the up-regulation of IKK-α, and that there might exist the functional interaction between them during apoptotic pathways mediated by DNA damage.

Example 2

Nuclear Accumulation of IKK-α in Response to Cisplatin

It has recently been shown that IKK-α shuttles between the nucleus and the cytoplasm in a CRM-1-dependent manner (Birbach, A. et al., J. Biol. Chem. 277: 10842-10851 (2002)). Moreover, nuclear IKK-α possesses the ability to transactivate NF-κB-responsive genes that control survival pathways after cytokine exposure (Yamamoto, Y. et al., Nature 423: 655-659 (2003); and Anest, V. et al., Nature 423: 659-663 (2003)). Based on these findings, whether the subcellular localization of endogenous IKKs was changed in response to cisplatin was investigated.

Figure 4:
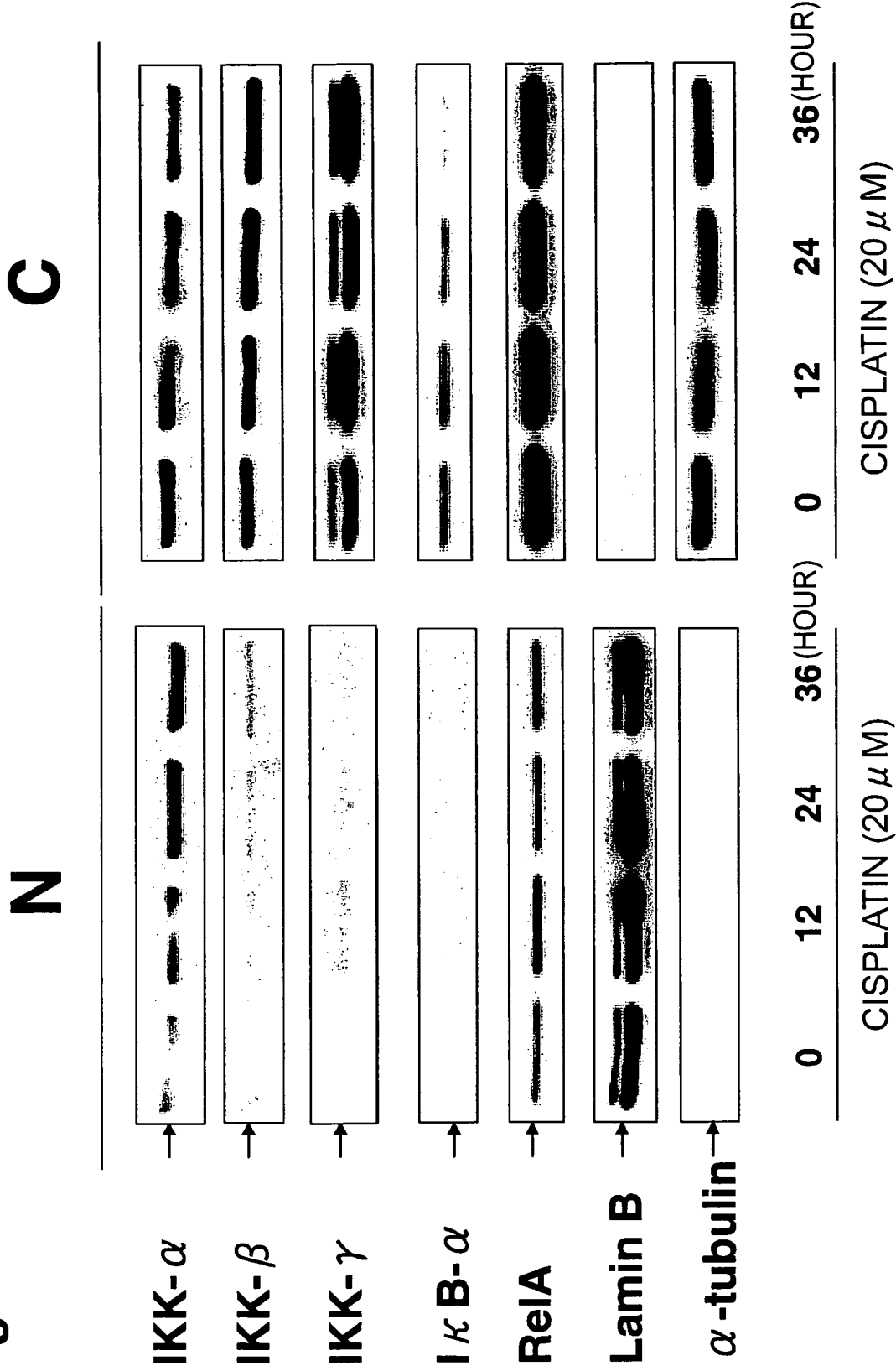
FIG. 4 is a diagram showing a result of immunoblot of nuclear (N) and cytoplasmic (C) fractions of U2OS cells treated with cisplatin.

Nuclear and cytoplasmic extracts were prepared from cisplatin-exposed or untreated U2OS cells and subjected to immunoblot with a given antibody. The purity of the nuclear and cytoplasmic fractions was confirmed by immunoblot using anti-lamin B and anti-α-tubulin antibodies, respectively. In agreement with the previously reported results, IKK-α was localized in both the nucleus and the cytoplasm, whereas IKK-β was largely expressed in the cytoplasm (FIG. 4). The amounts of IKK-α, IKK-β, and IKK-γ in the cytoplasm were not changed regardless of cisplatin treatment. Cisplatin treatment remarkably accumulated IKK-α in the nucleus in a time-dependent manner, but did not accumulate IKK-β so much in the nucleus. The transient accumulation of IKK-γ was observed in the nucleus after 12 hours of cisplatin treatment. In agreement with the enhanced phosphorylation of IκB-α in response to cisplatin, cytoplasmic IκB-α was decreased in a time-dependent manner. However, cisplatin treatment had almost no effect on the nuclear accumulation of p65-NF-κB subunit (RelA). This indicates that the presence of cisplatin might inhibit p65 nuclear translocation. This idea suggests that of IKKs, IKK-α, which was remarkably accumulated in the nucleus by cisplatin treatment, might have a certain function in the nucleus during apoptosis mediated by cisplatin.

Figure 5:
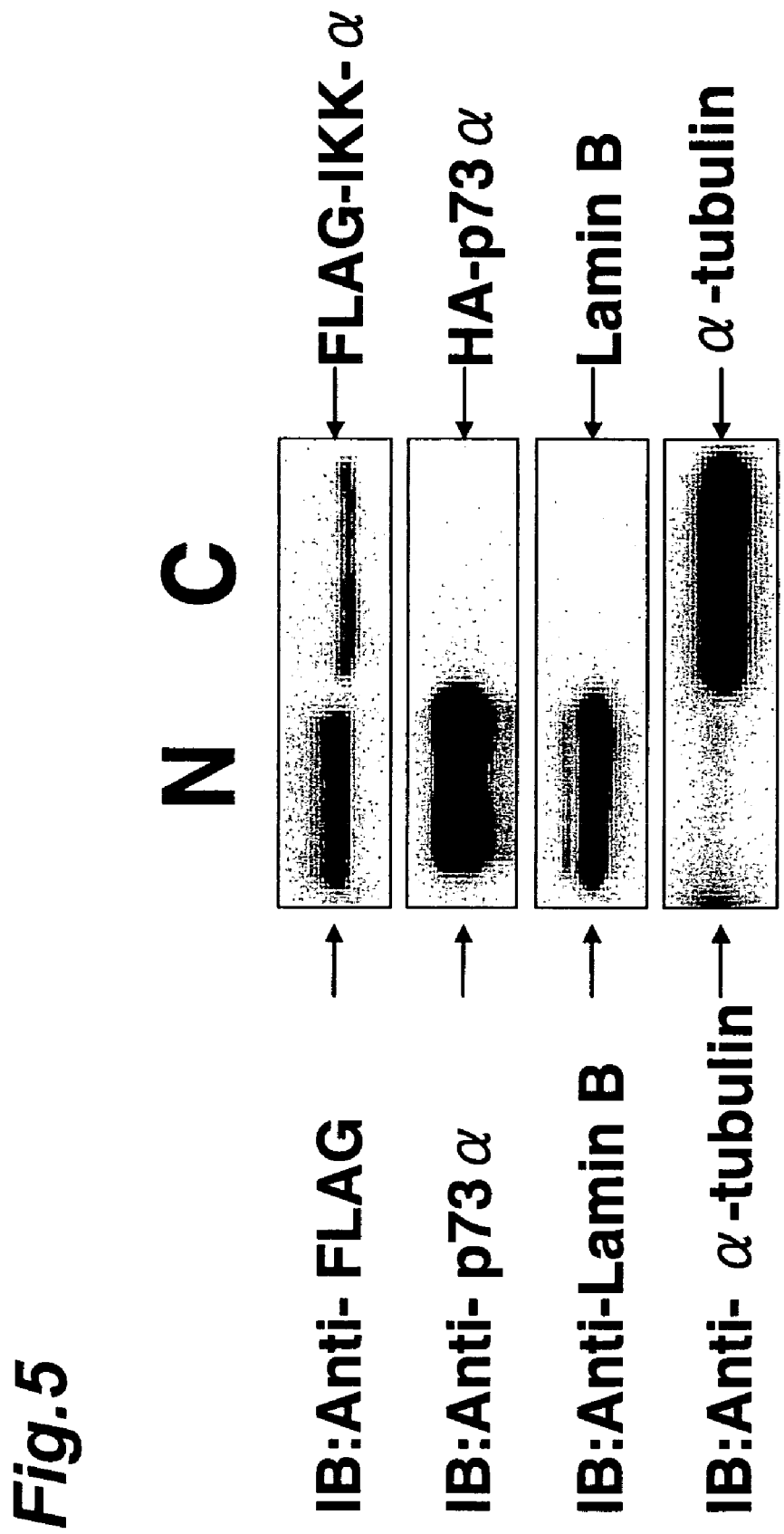
FIG. 5 is a diagram showing a result of immunoblot of nuclear (N) and cytoplasmic (C) fractions of U2OS cells transfected with a FLAG-IKK-α or HA-p73α expression plasmid.
Figure 6:
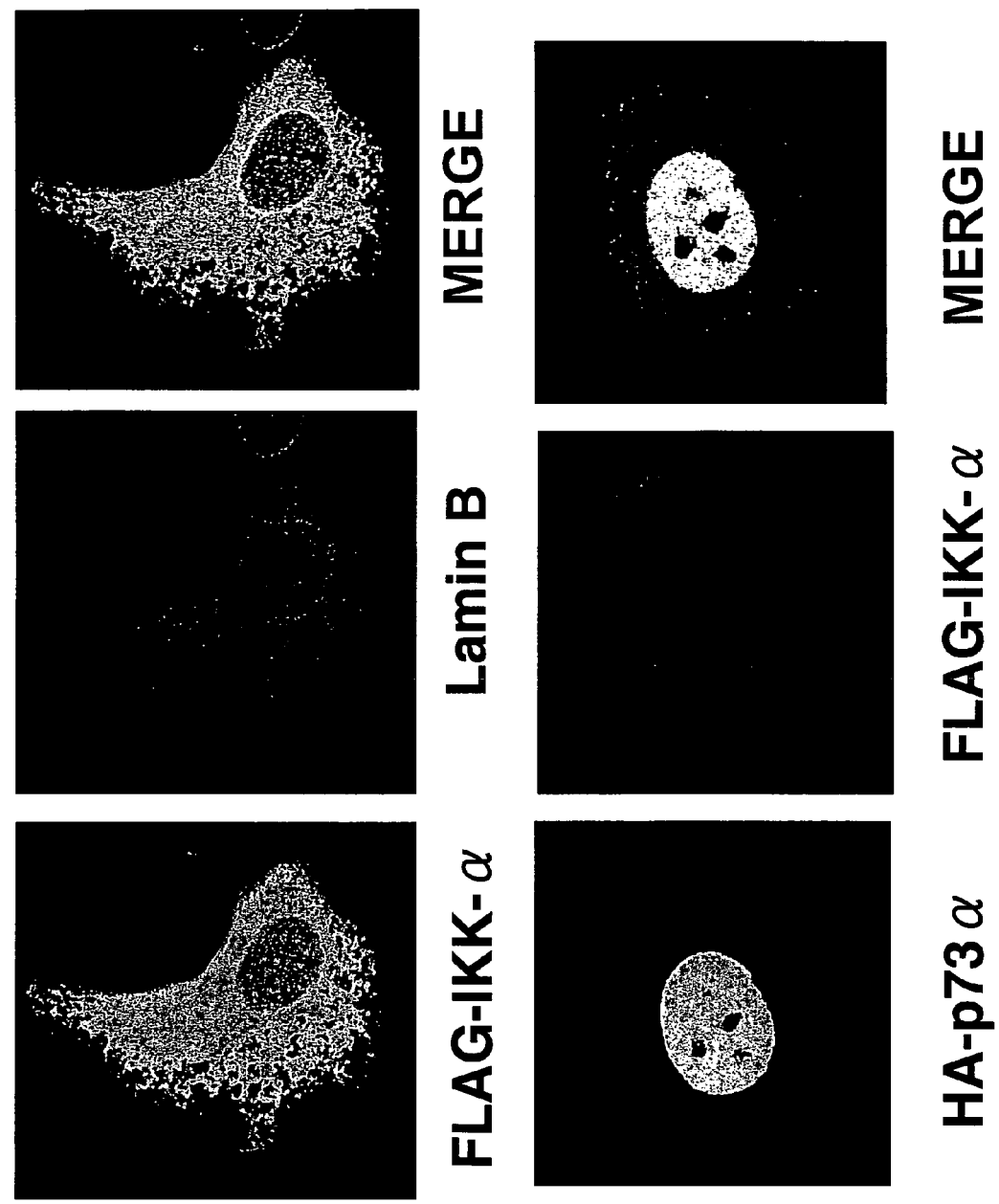
FIG. 6 is a photograph showing a result of double staining by indirect immunofluorescence of U2OS cells transiently transfected with a FLAG-IKK-α expression plasmid alone (upper three photographs) or together with HA-p73α (lower three photographs). The merge indicates a photograph overlaying FLAG-IKK-α on lamin B or HA-p73α on FLAG-IKK-α.

To investigate whether exogenous. IKK-α expression influenced the behavior of endogenous IKK-α, the intracellular distribution of exogenous IKK-α was examined by immunoblot and immunofluorescence staining. Nuclear and cytoplasmic fractions were prepared from U2OS cells transfected with an expression plasmid encoding FLAG-IKK-α or HA-p73α and subjected to immunoblot using an anti-FLAG or anti-p73 antibody, respectively. As shown in FIG. 5 (which shows the result of immunoblot of the cells after 48 hours of transfection), HA-p73α was largely localized in the nucleus, whereas FLAG-IKK-α was present in both the nucleus and the cytoplasm. Surprisingly, the result of immunofluorescence staining with anti-FLAG and anti-lamin antibodies clearly showed that exogenous IKK-α was localized in the cytoplasm and the nuclear matrix, as also indicated by extensive coexistence with lamin B serving as a nuclear matrix marker (FIG. 6). Interestingly, HA-p73α coexisted with FLAG-IKK-α in the nuclear matrix. This suggests that nuclear IKK-α might interact with pro-apoptotic p73 and regulate its function.

Example 3

Change in NF-κB Activation in U2OS Cells by Cisplatin Exposure

Figure 7:
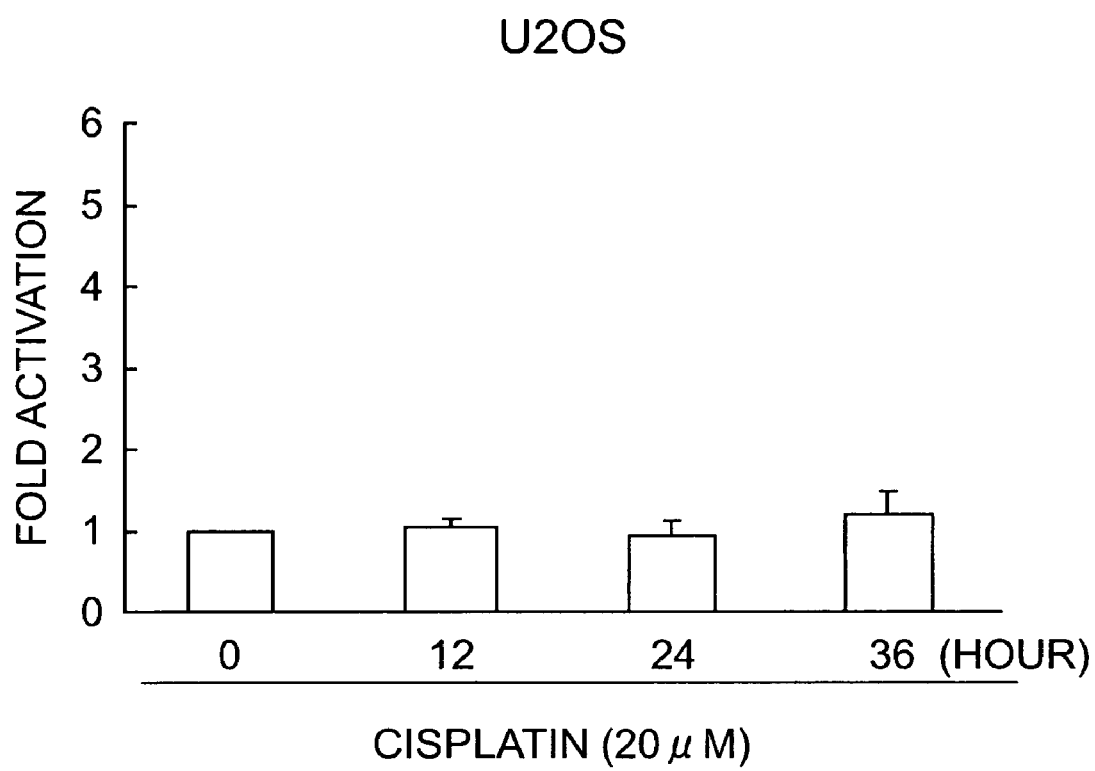
FIG. 7 is a graph showing the fold activation of NF-κB in U2OS cells treated with cisplatin.
Figure 8:
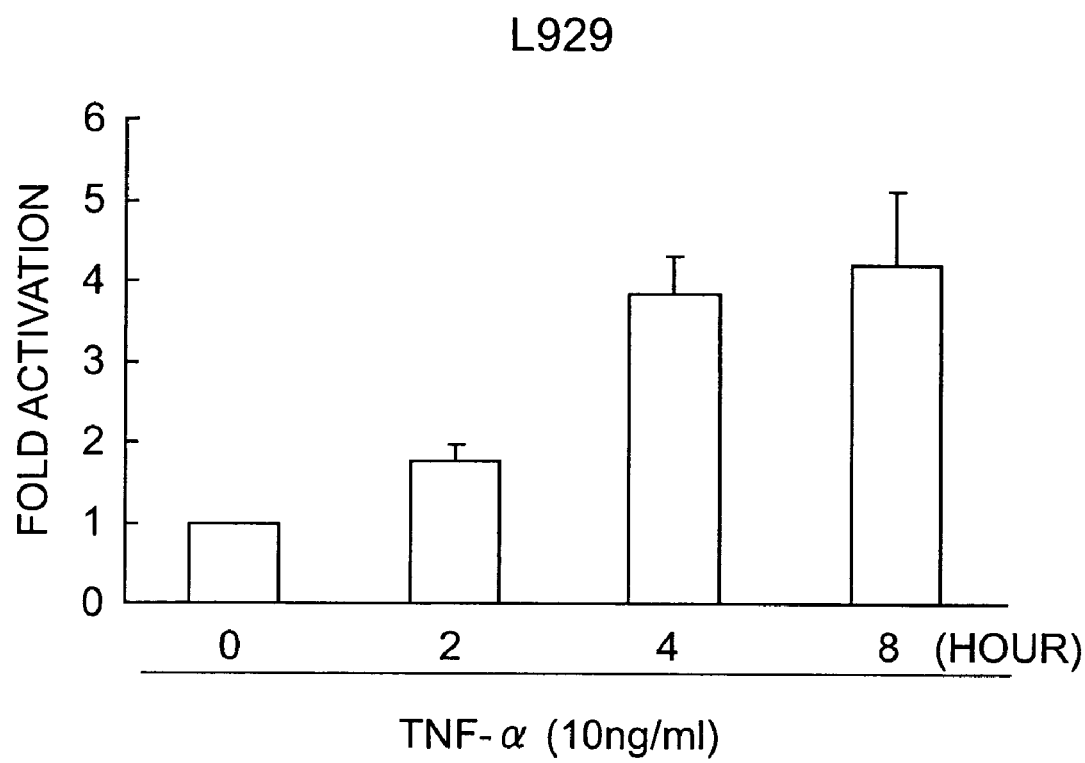
FIG. 8 is a graph showing the fold activation of NF-κB in L929 cells treated with TNF-α.
Figure 9:
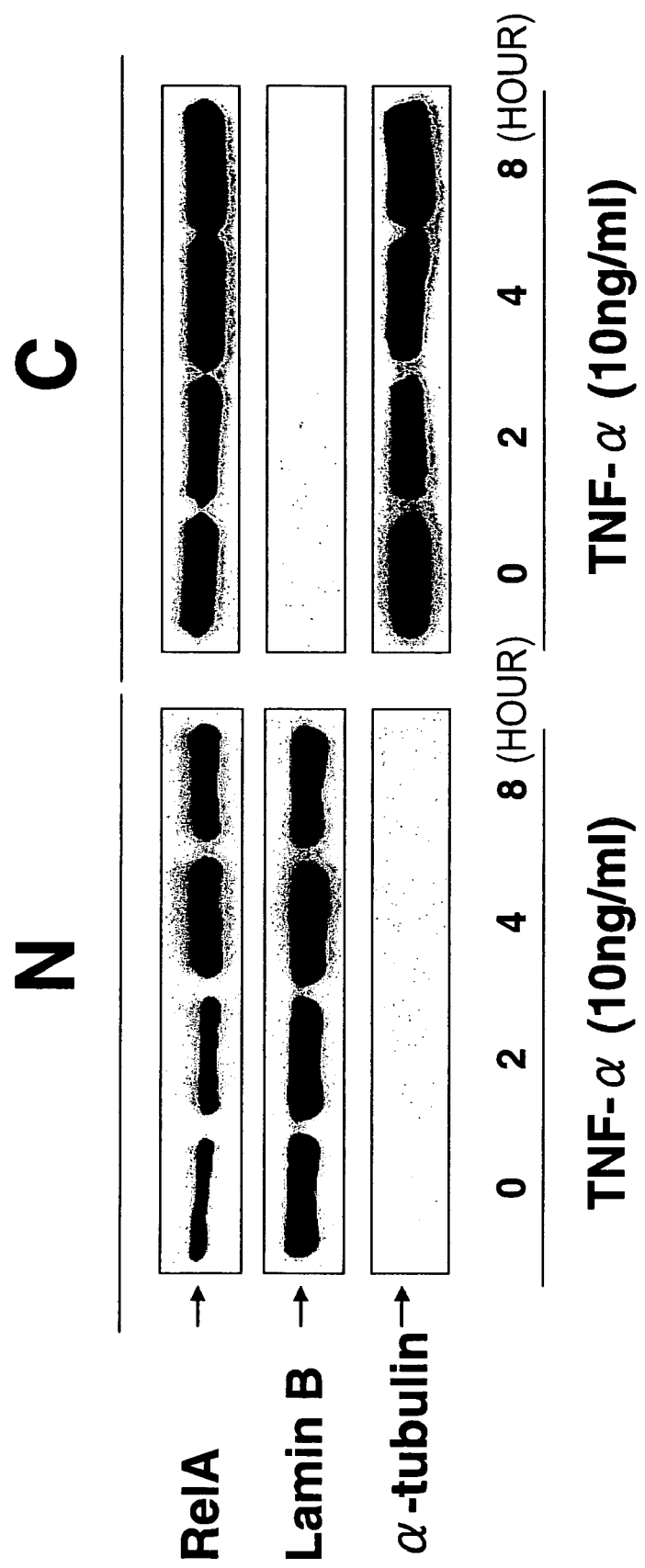
FIG. 9 is a diagram showing a result of immunoblot of nuclear (N) and cytoplasmic (C) fractions of L929 cells exposed to TNF-α. Interaction between IKK-α and p73.

As described above, the amount of nuclear transactivating p65 subunit was not changed in U2OS cells treated with cisplatin. In light of these results, whether NF-κB was activated in response to cisplatin was investigated. U2OS cells transfected with a NF-κB reporter plasmid were treated with cisplatin and assayed for their luciferase activities. The cisplatin treatment did not enhance NF-κB-dependent transcriptional activation (FIG. 7). When mouse fibroblast L929 cells were exposed to TNF-α, NF-κB-dependent transcriptional activation was observed after 2 hours (FIG. 8). L929 cells have been used widely for examining the TNF-α-dependent activation of NF-κB. The treatment of the L929 cells with TNF-α remarkably accumulated p65 in the nucleus (FIG. 9). From these results, unlike TNF-α, no remarkable effect of cisplatin on NF-κB-dependent transcriptional activation seems to be due to the absence of regulation of the nuclear accumulation of p65.

Example 4

Interaction Between IKK-α and p73

Figure 10:
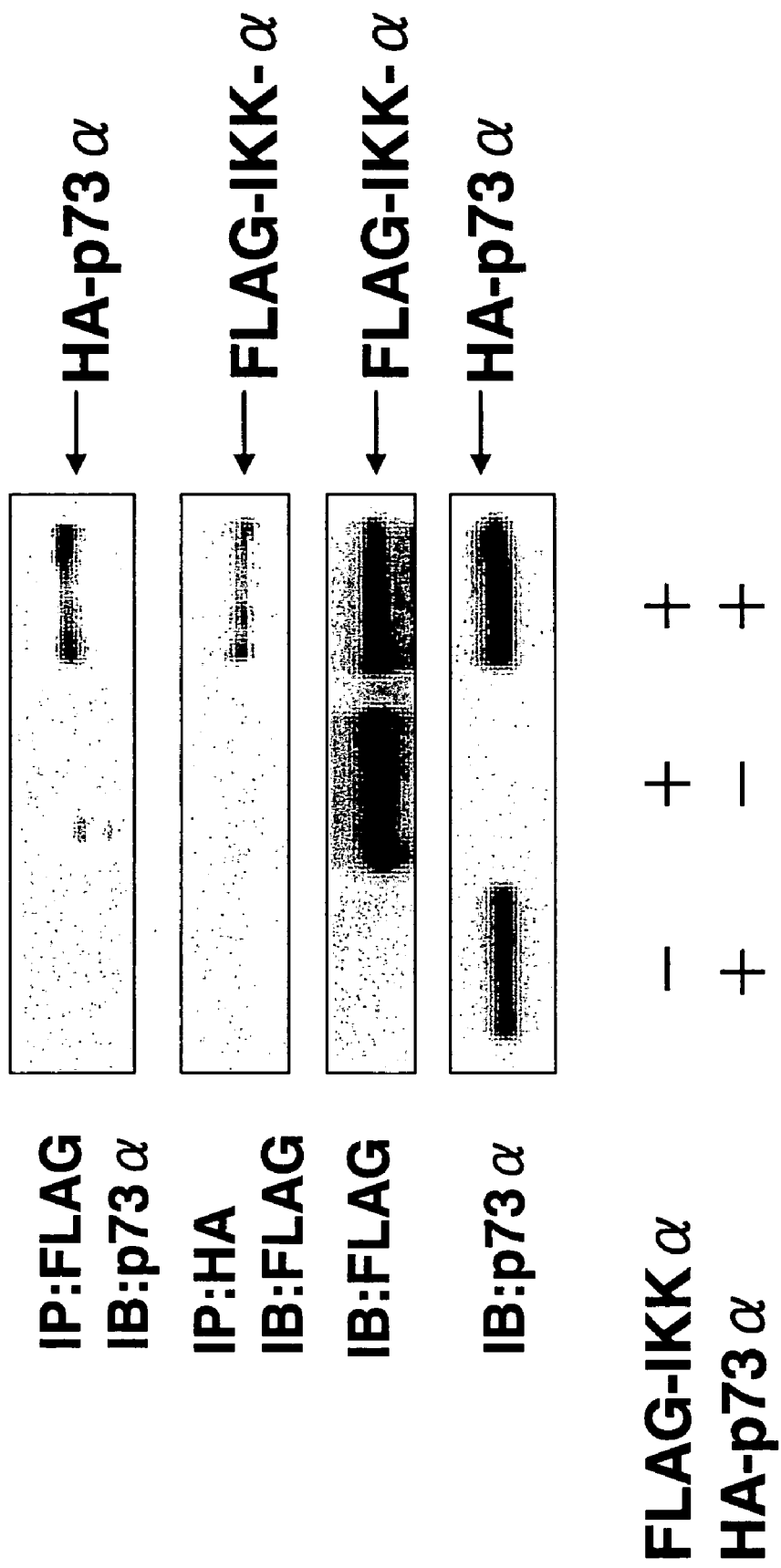
FIG. 10 is a diagram showing a result of immunoprecipitation and immunoblot of COS7 cells transiently transfected with the given combinations of expression plasmids. IP and IB denote antibodies used in immunoprecipitation and immunoblot, respectively.
Figure 11:
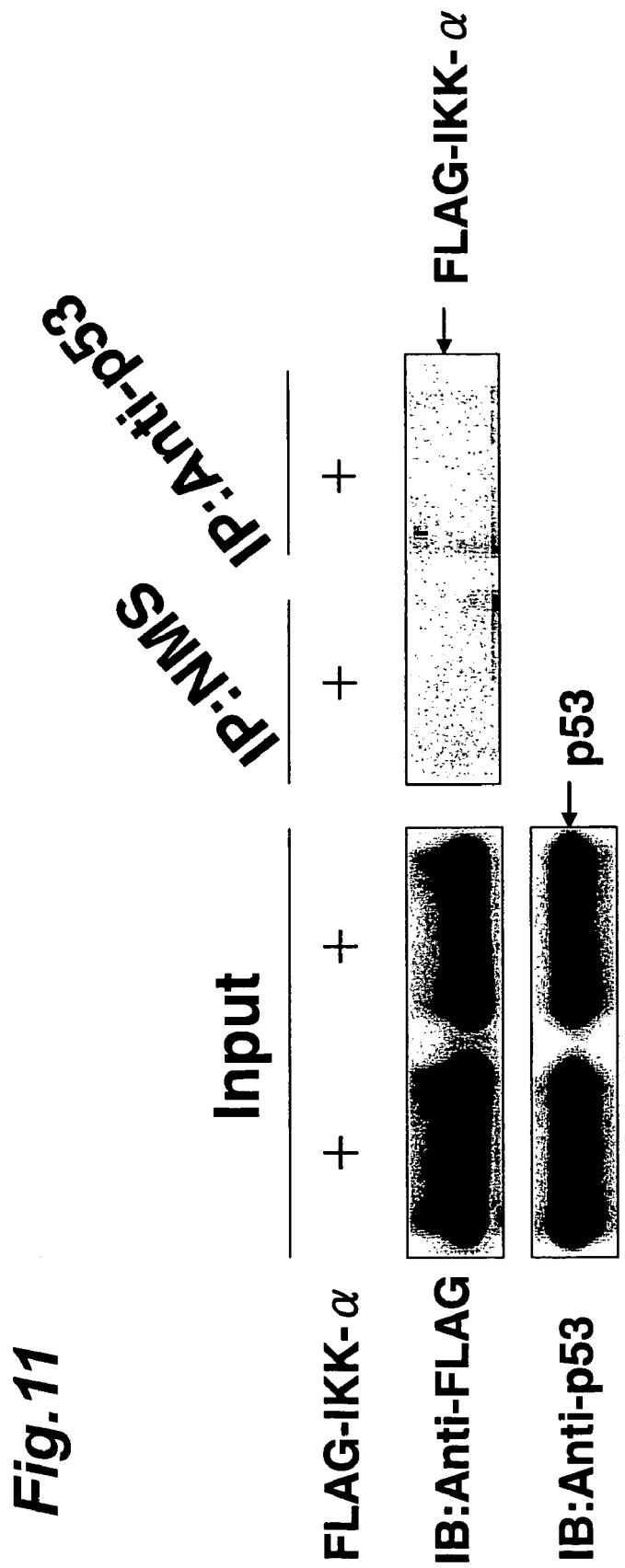
FIG. 11 is a diagram showing a result of immunoprecipitation with normal mouse serum (NMS) or an anti-p53 antibody and immunoblot with an anti-FLAG antibody conducted on COS7 cells transiently transfected with a FLAG-IKK-α expression plasmid.
Figure 12:
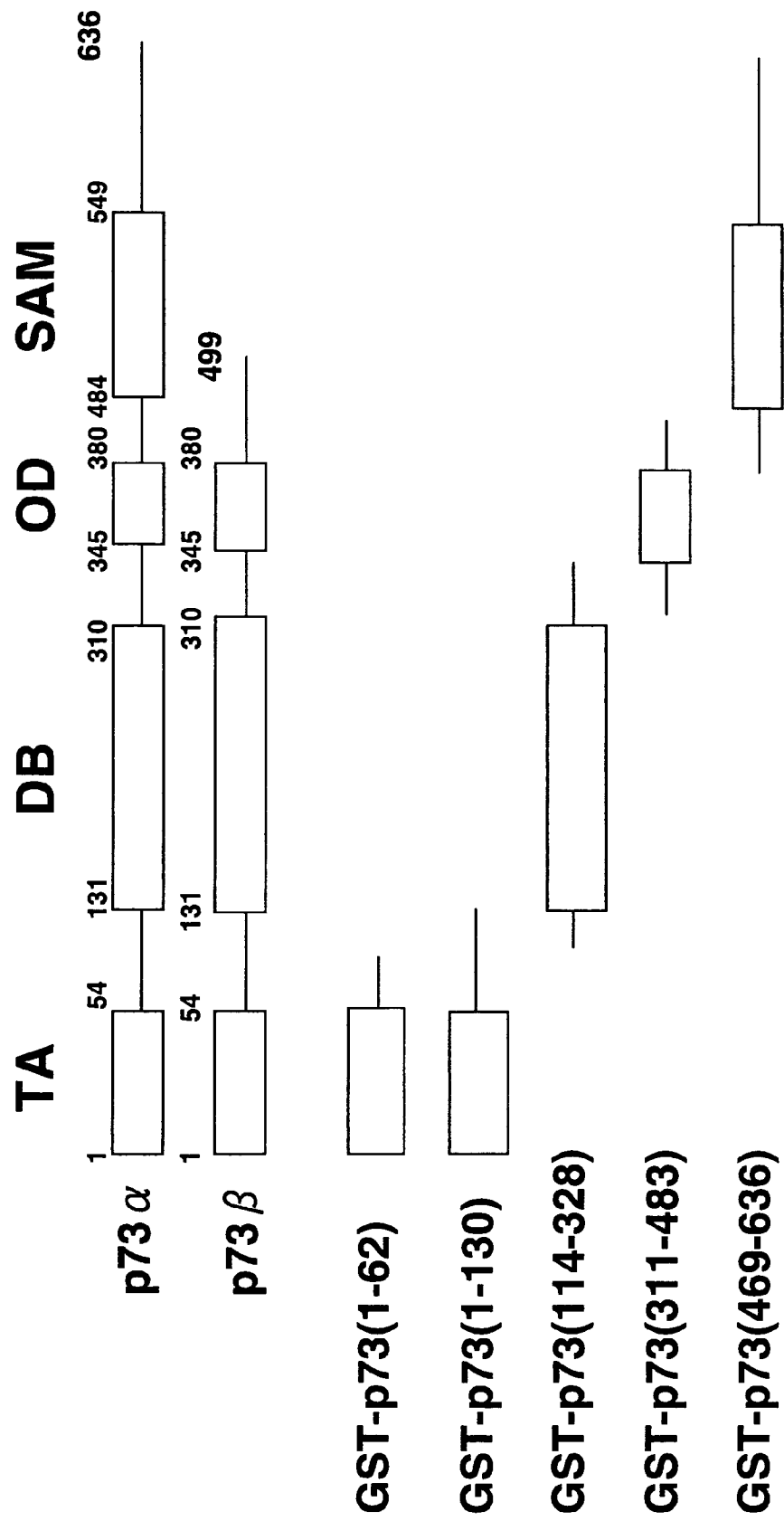
FIG. 12 is a schematic diagram of GST-p73 fusion proteins. TA denotes a transactivation domain, DB denotes a DNA-binding domain, OD denotes an oligomerization domain, and SAM denotes a sterile α motif domain.
Figure 13:
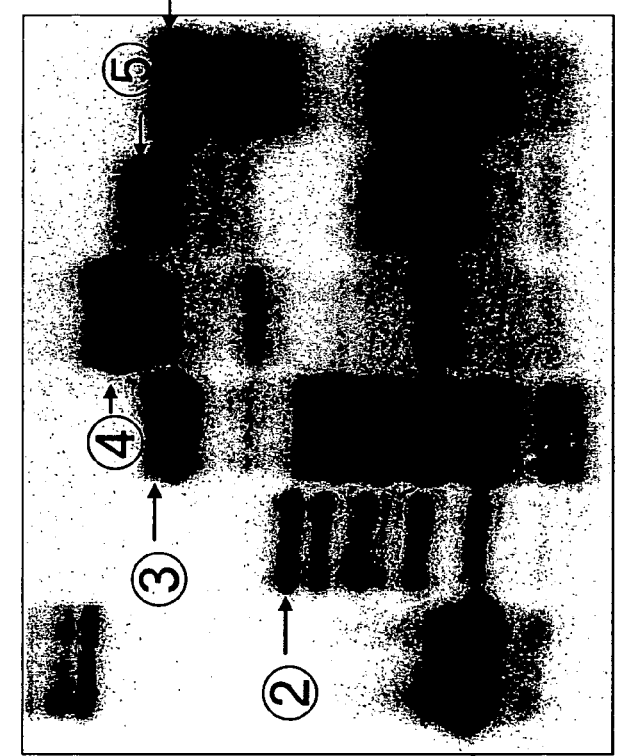
FIG. 13 is a diagram showing a result of immunoblot with an anti-FLAG antibody in in vitro pull-down assay (upper panel) and a diagram showing a result of immunoblot with an anti-GST antibody in in vitro pull-down assay (lower panel).

To investigate whether IKK-α interacted with p73 in cultured mammal cells, whole cell lysates were prepared from transfected COS7 cells, then immunoprecipitated with an anti-FLAG or anti-HA antibody, and analyzed by immunoblot using an anti-p73 or anti-FLAG antibody, respectively. As shown in FIG. 10, exogenously expressed FLAG-IKK-α and HA-p73α formed stable complexes in the COS7 cells. Likewise, HA-p73β was co-immunoprecipitated with FLAG-IKK-α (data not shown). By contrast, when endogenous p53 was immunoprecipitated and immunoblotted with an anti-FLAG antibody, co-immunoprecipitated FLAG-IKK-α was not detected (FIG. 11). This shows that IKK-α interacts with p73, but not with p53, in cells. To identify determinants of p73 participating in the interaction with IKK-α, several deletion mutants of p73 fused to GST were prepared and examined for their abilities to bind to FLAG-IKK-α by in-vitro pull-down assay. These mutants were designed on the basis of the functional domains of p73 including transactivation, DNA-binding, oligomerization, and SAM domains (FIG. 12). FLAG-IKK-α bonded to GST-p73 (114-328) but not to other GST-fused proteins (FIG. 13). These results suggested that IKK-α directly interacts with p73 via the DNA-binding domain of p73.

Experiment 5

Stabilization of p73 by IKK-α

Figure 14:
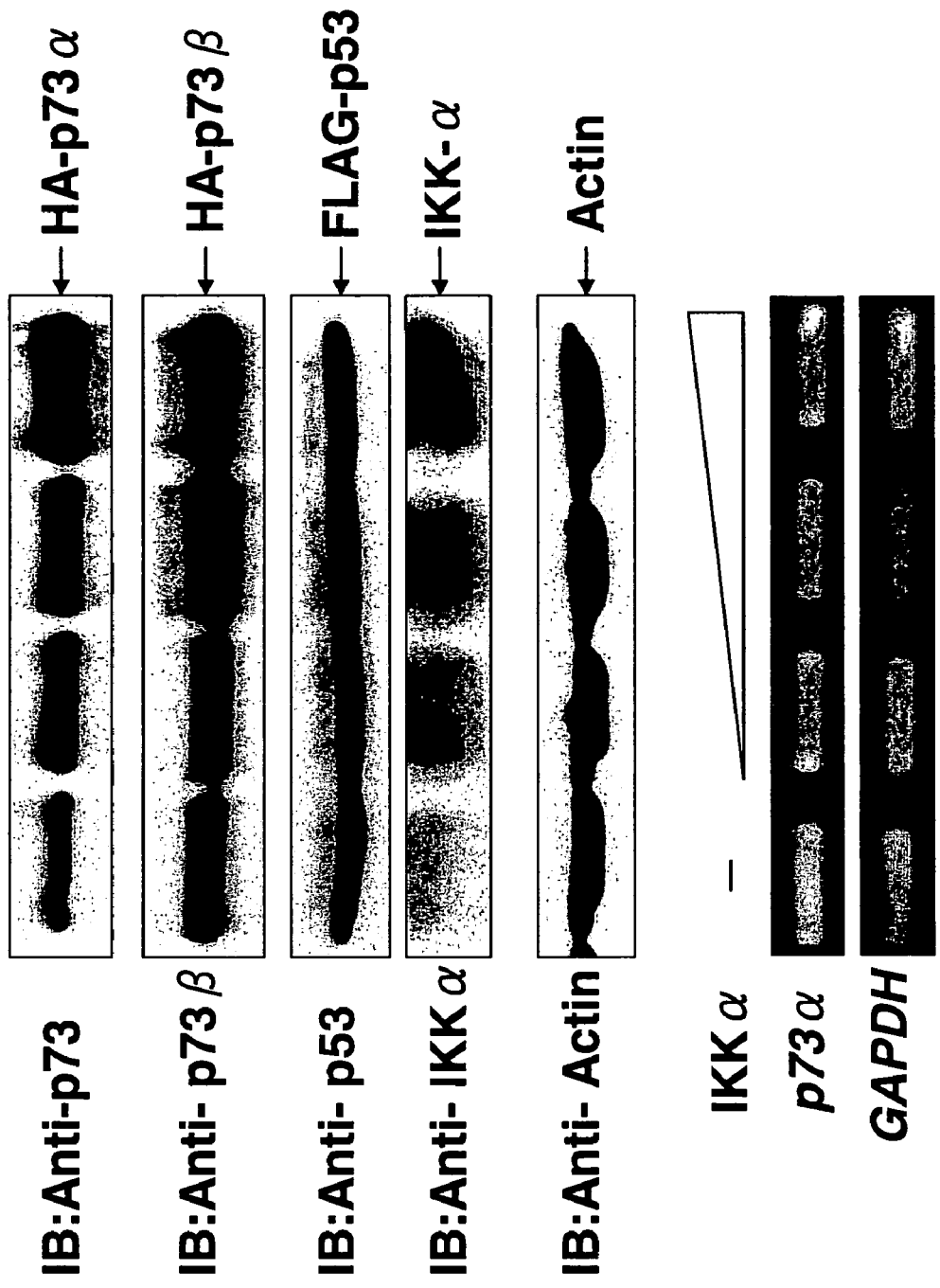
FIG. 14 is a diagram showing a result of immunoblot (upper panels) and RT-PCR (lower panels) of COS7 cells transiently cotransfected with the given combinations of expression plasmids.
Figure 15:
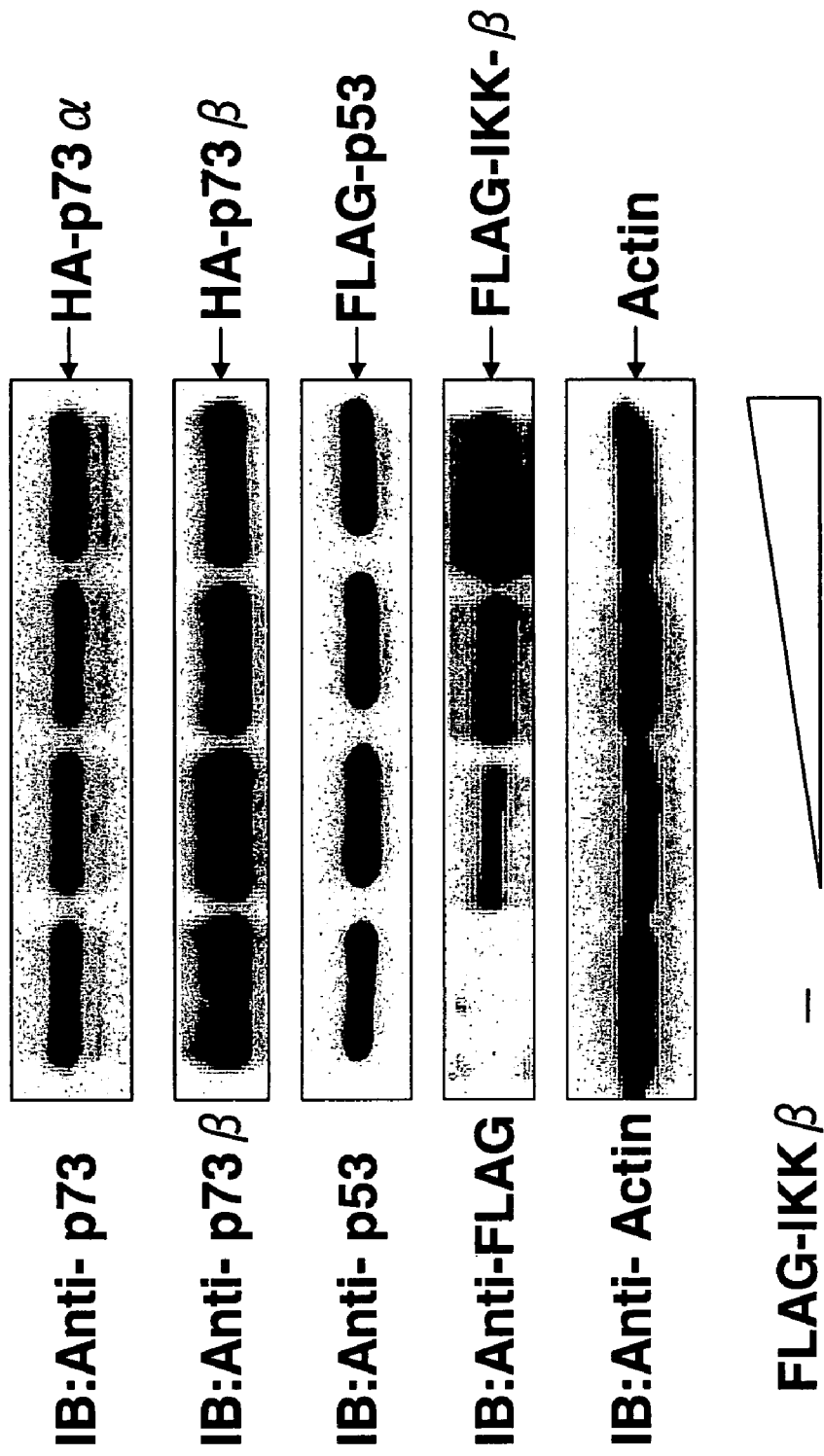
FIG. 15 is a diagram showing a result of immunoblot of COS7 cells transiently cotransfected with the given combinations of expression plasmids.

As previously reported, some protein kinases (e.g., c-Abl and PKCδ) that interact with p73 can stabilize p73. To confirm whether IKK-α influenced the stabilization of p73, COS7 cells were transfected with a constant amount of HA-p73α expression plasmid together with or without varying amounts of IKK-α expression plasmids and examined for HA-p73α protein levels. As shown in FIG. 14, the presence of exogenous IKK-α remarkably increased the amount of HA-p73α, whereas IKK-α had no detectable effect on the stabilization of FLAG-p53. HA-p73β was also stabilized by IKK-α at a degree lower than that of HA-p73α. Under the experimental conditions that increased IKK-α, no remarkable change was seen in the expression level of p73α mRNA (FIG. 14). This suggests that IKK-α controls p73 at protein levels. Next, whether IKK-β influenced the stabilization of p73 and p53 was investigated by transient transfection. As shown in FIG. 15, FLAG-IKK-β had no detectable effect on the stabilization of both p73 and p53.

Figure 16:
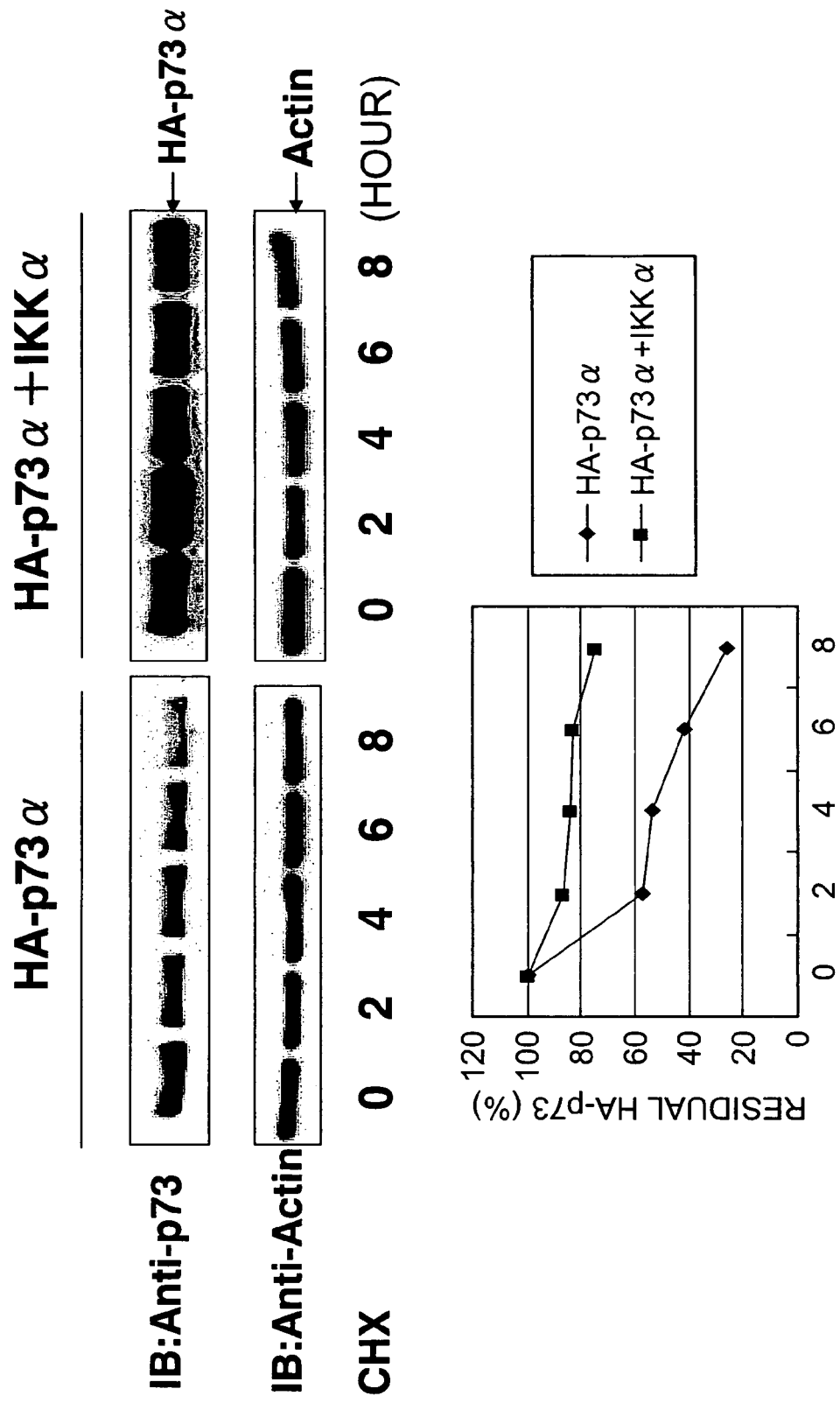
FIG. 16 is a diagram showing a result of immunoblot of COS7 cells transiently transfected with a HA-p73α expression plasmid alone or together with an IKK-α expression plasmid and then treated with cycloheximide (CHX) (upper panel), and a graph showing residual HA-p73α (lower panel).
Figure 17:
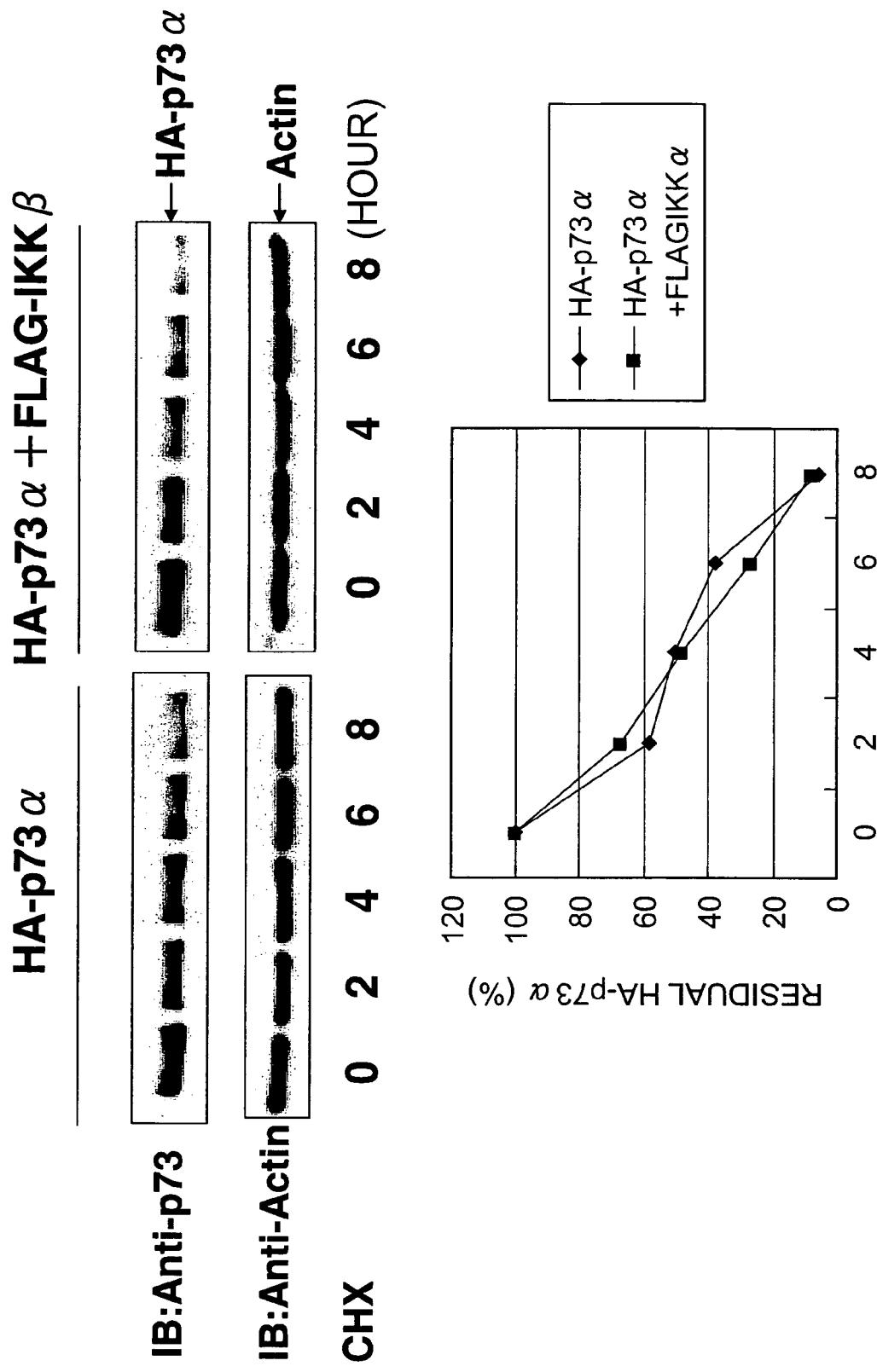
FIG. 17 is a diagram showing a result of immunoblot of COS7 cells transiently transfected with a HA-p73α expression plasmid alone or together with an IKK-β expression plasmid and then treated with cycloheximide (CHX) (upper panel), and a graph showing residual HA-p73α (lower panel).

To confirm whether IKK-α regulated p73 turnover, the degradation rate of p73 in transfected COS7 cells was examined. After 24 hours of transfection, the cells were treated with cycloheximide. At the indicated time points, lysates from the whole cells were prepared and subjected to immunoblot using an anti-p73 antibody. As shown in FIG. 16, the degradation rate of HA-p73α in cells expressing both HA-p73α and IKK-α was lower than that in cells expressing HA-p73α alone. By contrast, the half-life of HA-p73 a was not prolonged even in the presence of FLAG-IKK-β (FIG. 17). Thus, the stabilization of p73 mediated by IKK-α is attributed to increase in the half-life of p73.

Figure 18:
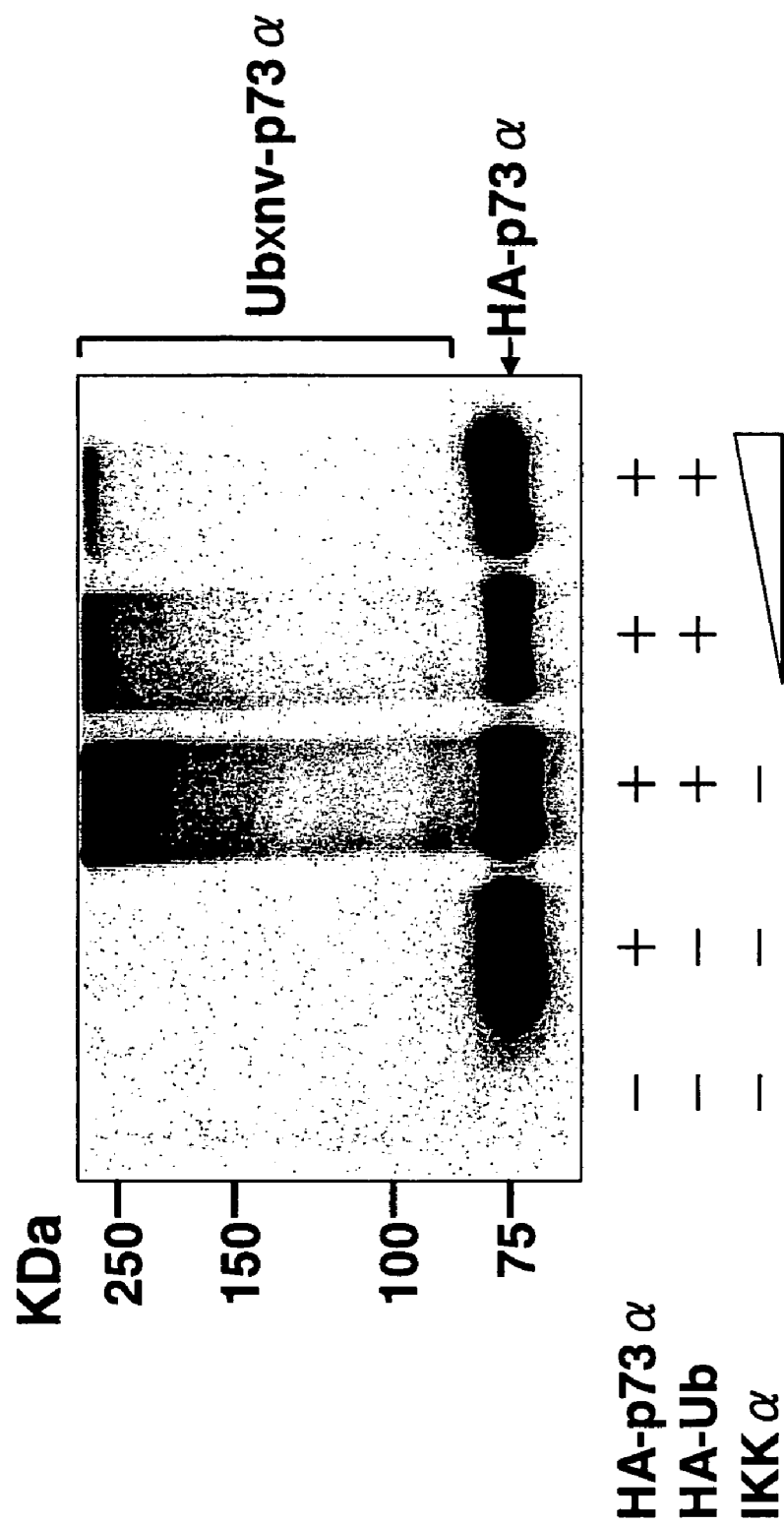
FIG. 18 is a diagram showing a result of immunoprecipitation with an anti-p73 antibody and immunoblot with an anti-HA antibody conducted on COS7 cells transiently cotransfected with expression plasmids for HA-p73α and HA-Ub together with or without varying amounts of IKK-α expression plasmids and then treated with MG-132. Ubxn-p73α denotes slowly migrating ubiquitinated forms of HA-p73α.
Figure 19:
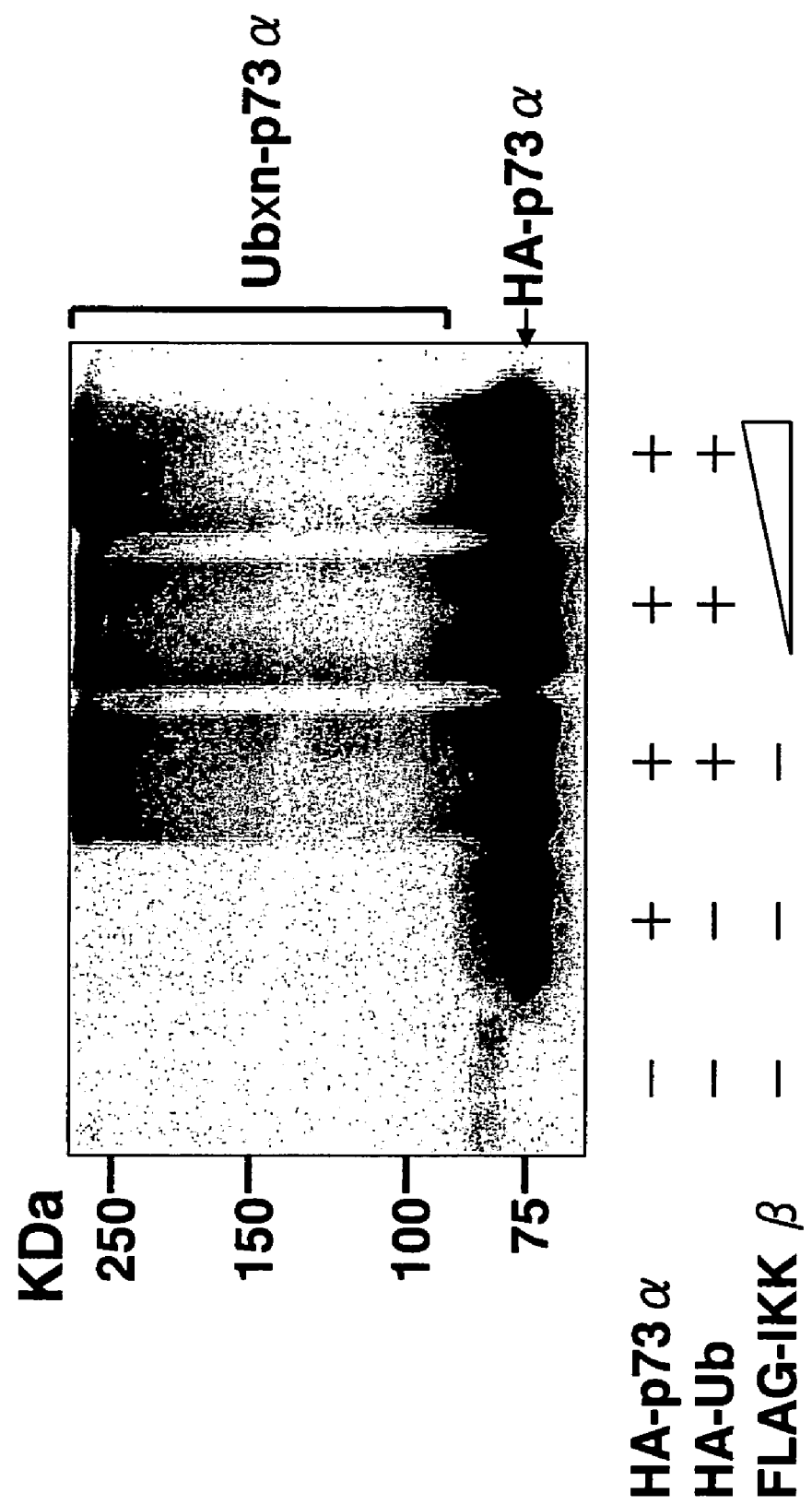
FIG. 19 is a diagram showing a result of immunoprecipitation with an anti-p73 antibody and immunoblot with an anti-HA antibody conducted on COS7 cells transiently cotransfected with expression plasmids for HA-p73α and HA-Ub together with or without varying amounts of IKK-β expression plasmids and then treated with MG-132. Ubxn-p73α denotes slowly migrating ubiquitinated forms of HA-p73α.

As described by Lee, C.-W. et al., Oncogene 18: 4171-4181 (1999), the steady-state level of p73 was regulated at least partially by the proteolytic process through the ubiquitin-proteasome pathway. Whether IKK-α inhibited the ubiquitination of p73 was investigated. COS7 cells were transfected with expression plasmids for HA-p73α and HA-ubiquitin together with or without varying amounts of IKK-α or FLAG-IKK-β expression plasmids. After 48 hours of the transfection, lysates from the whole cells were analyzed by immunoprecipitation and immunoblot and examined for the presence of p73α containing HA-ubiquitin. The amount of ubiquitinated p73α was decreased by the presence of IKK-α (FIG. 18), whereas FLAG-IKK-β inhibited the ubiquitination of p73α to a somewhat lesser degree (FIG. 19).

Taken together, these results strongly suggested that IKK-α inhibits the ubiquitination of p73 and thereby enhances the stabilization of p73.

Example 6

Enhancement of p73-mediated Transactivation Function in p53-Deficient H1299 Cells by IKK-α

Figure 21:
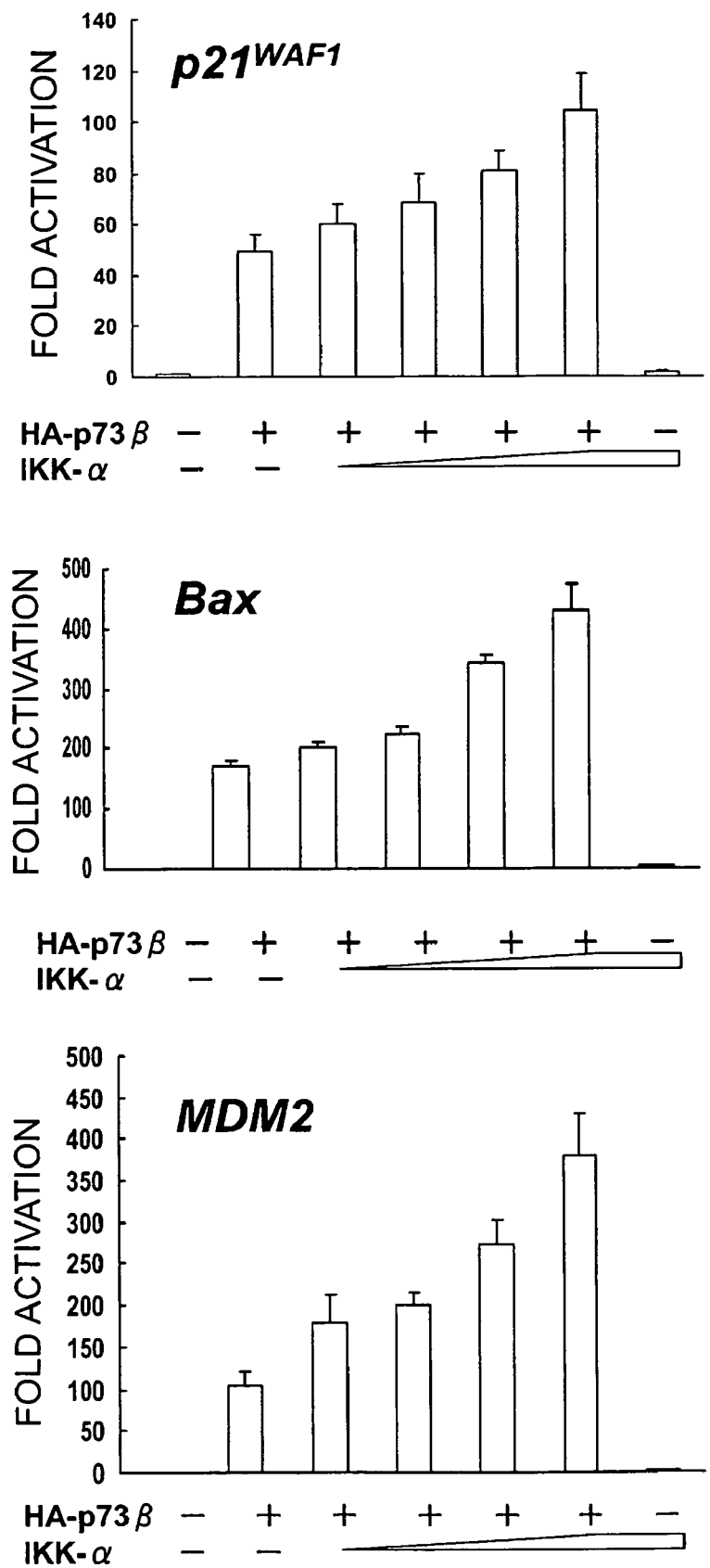
FIG. 21 is a graph showing the fold transcriptional activation of p53/p73-responsive promoters in p53-deficient H1299 cells transiently cotransfected with an expression plasmid encoding HA-p73β together with a luciferase reporter carrying a p53-responsive element derived from a p21$^{WAF1}$, Bax, or MDM2 promoter and with a Renilla luciferase plasmid (pRL-TK) in the presence or absence of varying amounts of pcDNA3-IKK-α.
Figure 23:
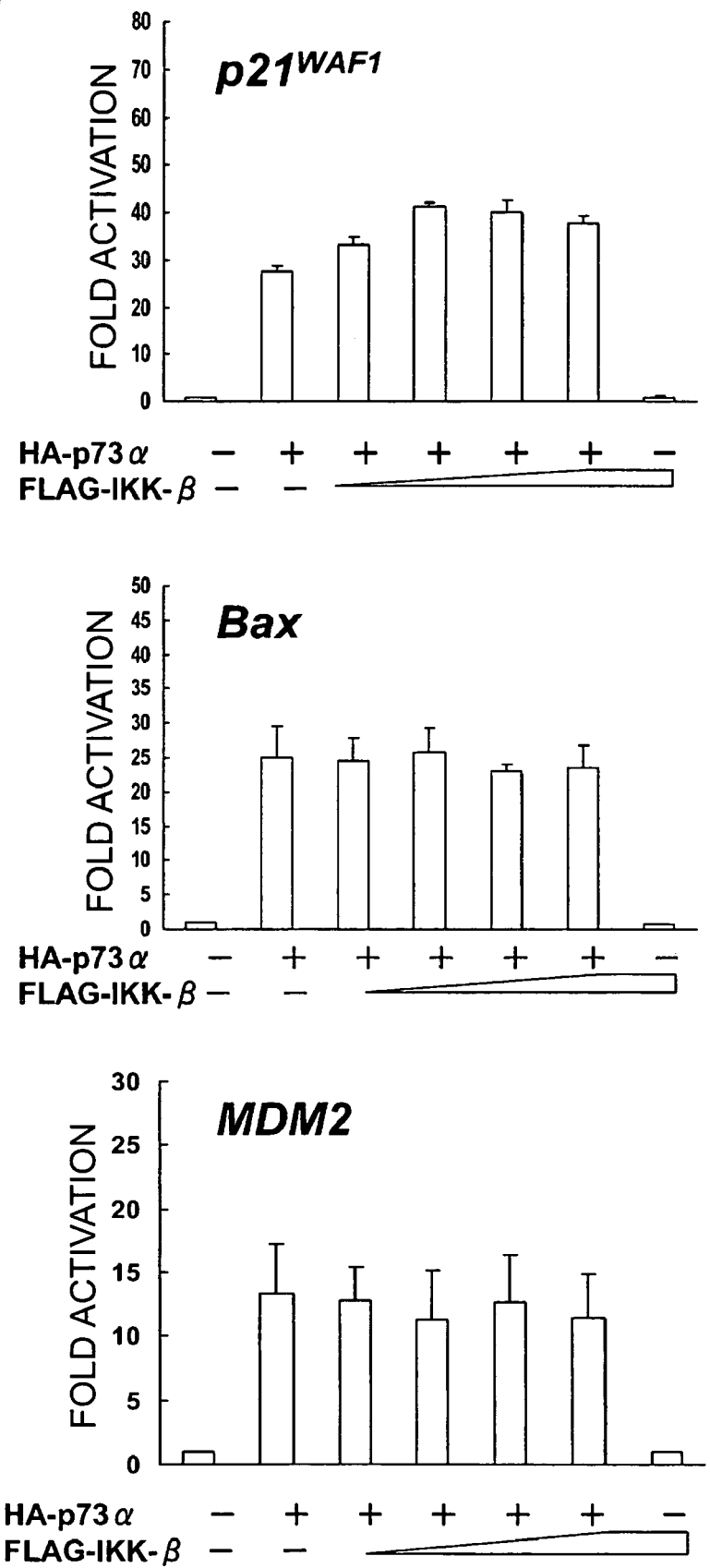
FIG. 23 is a graph showing the fold transcriptional activation of p53/p73-responsive promoters in H1299 cells transiently transfected with a HA-p73α expression plasmid together with a given luciferase reporter construct in the presence or absence of varying amounts of IKK-β expression plasmids.
Figure 24:
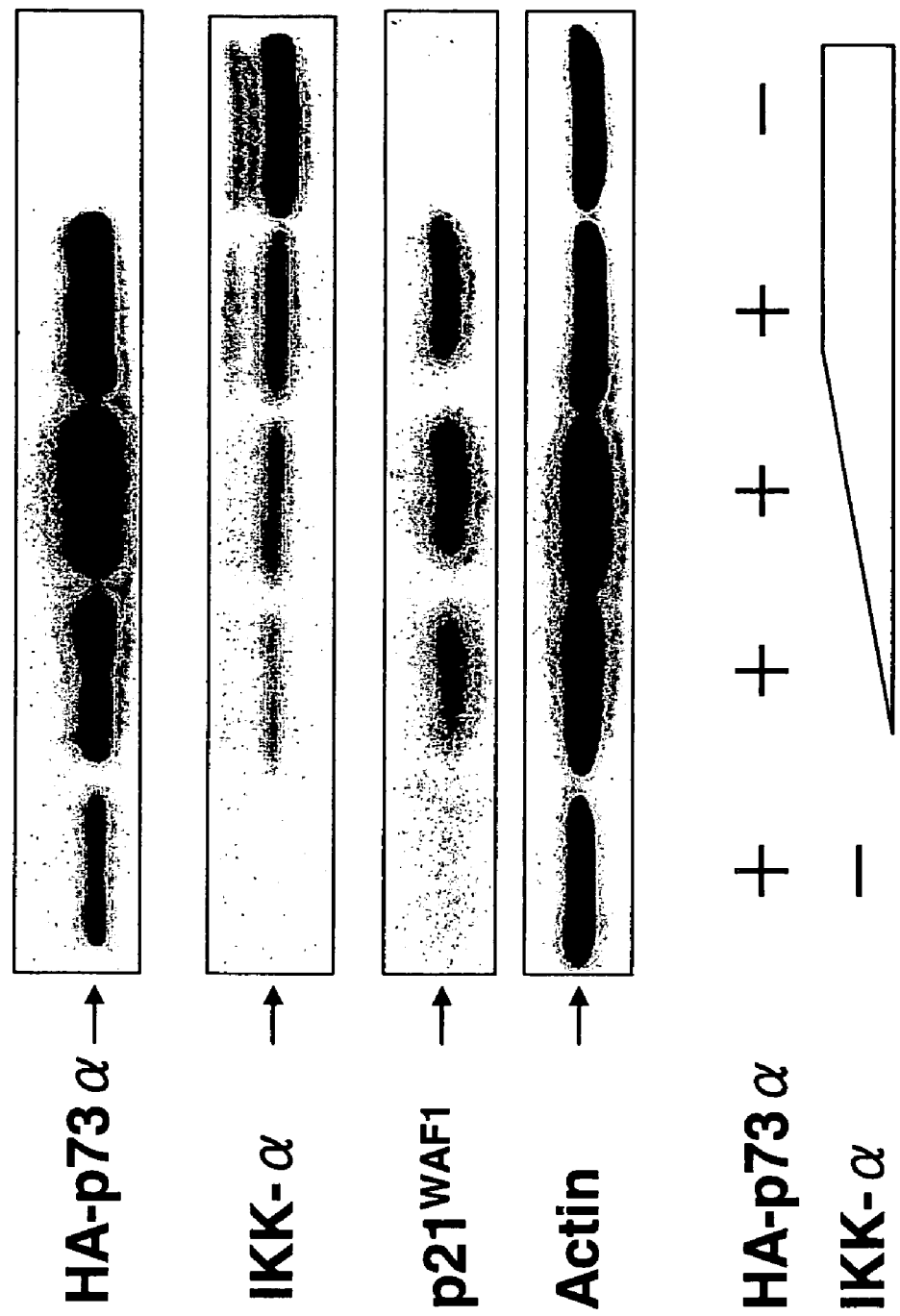
FIG. 24 is a diagram showing a result of immunoblot of H1299 cells transiently cotransfected with a constant amount of HA-p73α expression plasmid together with or without varying amounts of IKK-α expression plasmids.

To explore the functional implication of interaction between IKK-α and p73, the effect of IKK-α on p73-mediated transcriptional activation was first examined. H1299 cells deficient in p53 were transfected with a HA-p73α or HA-p73β expression plasmid and a luciferase reporter construct under the control of a p21$^{WAF1}$, Bax, or MDM2 promoter together with or without varying amounts of IKK-α expression plasmids. As shown in FIGS. 20 and 21, ectopically expressed p73 activated the transcription of the p53/p73-responsive reporters, as compared with empty plasmids as controls. Moreover, IKK-α alone had almost no effect on luciferase activity. Remarkable increase in p73-dependent transcriptional activation was dose-dependently observed in the coexpression of HA-p73α or HA-p73β with IKK-α. By contrast, increase in p53-responsive reporter gene activity was not induced by IKK-α (FIG. 22). To examine the specificity of p73-dependent transcriptional activation mediated by IKK-α, whether IKK-β enhanced p73 transcriptional activity to p53/p73-responsive promoters was confirmed. As shown in FIG. 23, no remarkable change in p73-dependent transcriptional activation was observed with FLAG-IKK-β. When exogenous IKK-α was expressed in H1299 cells, the induction of endogenous p21$^{WAF1}$ mediated by p73α was remarkably up-regulated (FIG. 24).

Taken together, these results suggested that IKK-α specifically enhances the transcriptional activity of p73.

Example 7

Contribution of IKK-α to Apoptosis Mediated by p73

Figure 25:
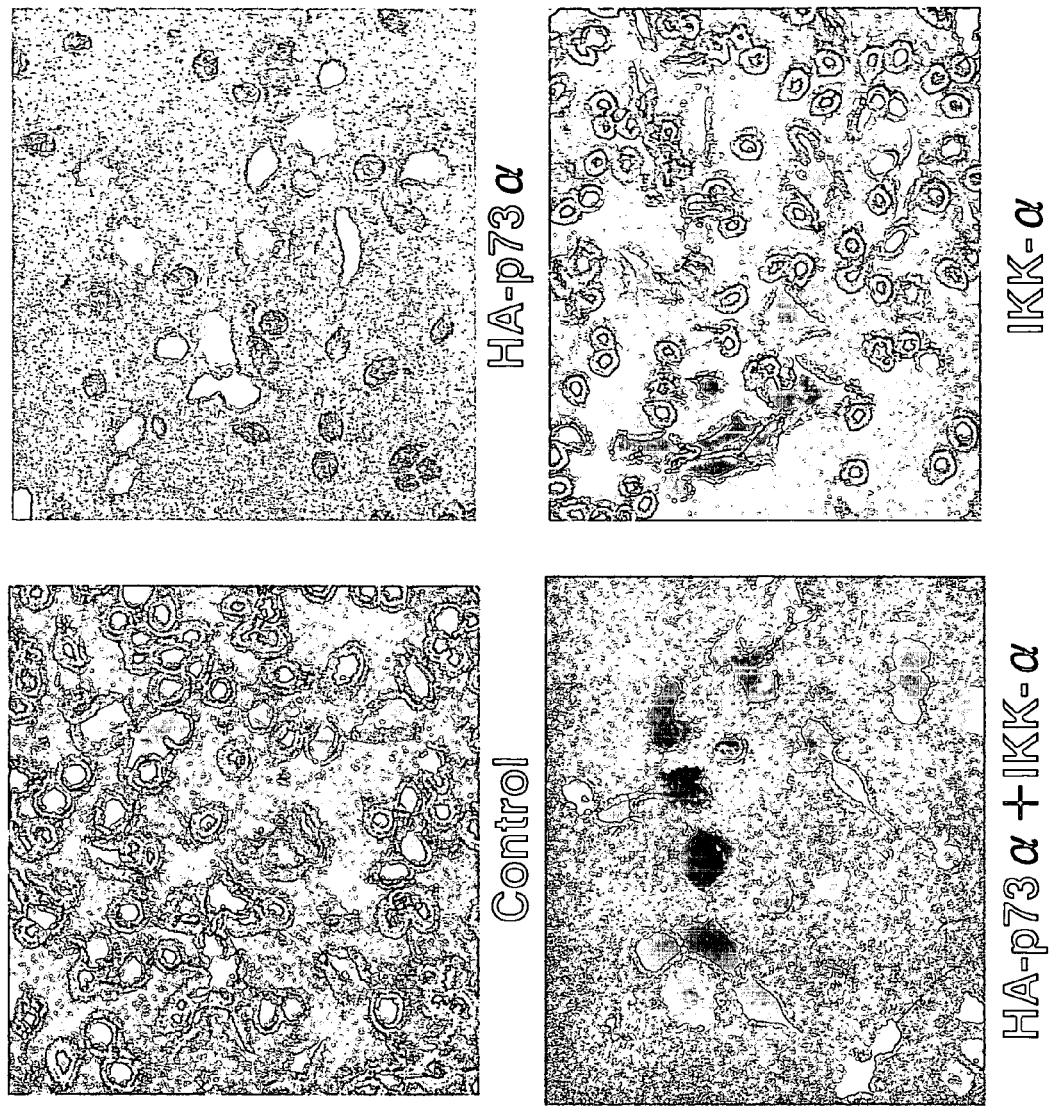
FIG. 25 is a photograph showing H1299 cells transiently transfected with a given expression plasmid and then double-stained.
Figure 26:
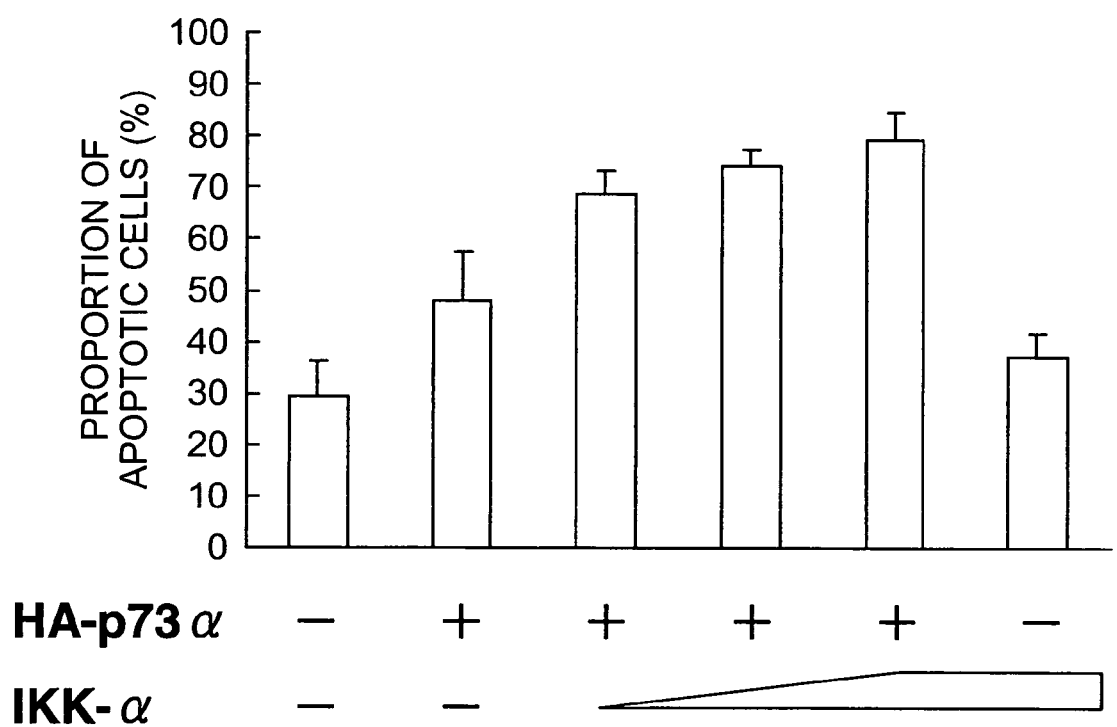
FIG. 26 is a graph showing the proportion of apoptotic cells to H1299 cells transiently transfected with a given expression plasmid.
Figure 27:
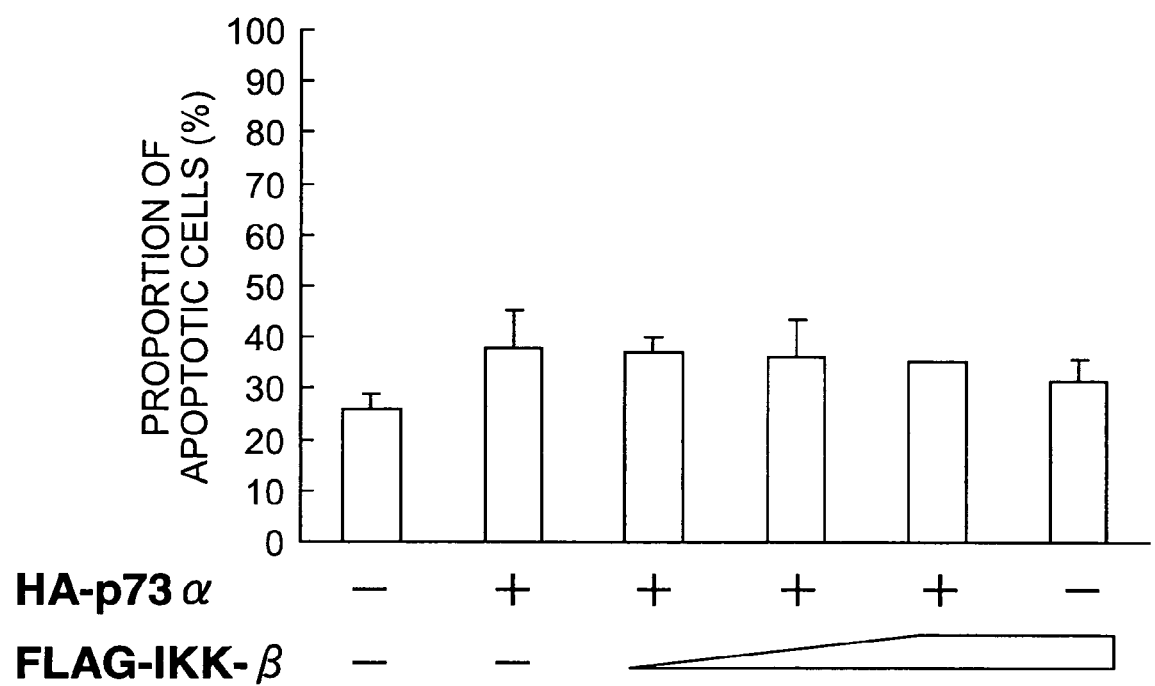
FIG. 27 is a graph showing the proportion of apoptotic cells to H1299 cells transiently transfected with a given expression plasmid.

Potential effect(s) of IKK-α on p73-dependent biological functions such as the regulation of apoptosis was examined. H1299 cells were transiently transfected with a constant amount of expression plasmids for HA-p73α and β-galactosidase together with or without varying amounts of IKK-α or FLAG-IKK-β expression plasmids. The β-galactosidase expression plasmid was used for identifying the transfected cells. After 48 hours of the transfection, the cells were subjected to double staining with trypan blue (nonviable cells) and Red-Gal (transfected cells), and the number of purple cells was scored. As shown in FIGS. 25 and 26, the coexpression of IKK-α with HA-p73α increased the number of cells undergoing apoptosis, as compared with transfection with HA-p73α alone. By contrast, the coexpression of FLAG-IKK-β had no remarkable effect on p73α-dependent apoptosis (FIG. 27).

These data are consistent with the positive effect of IKK-α on p73-dependent transcriptional activation.

Example 8

Influence of Mutant IKK-α Lacking Kinase Activity on the Stabilization of p73

Figure 28:
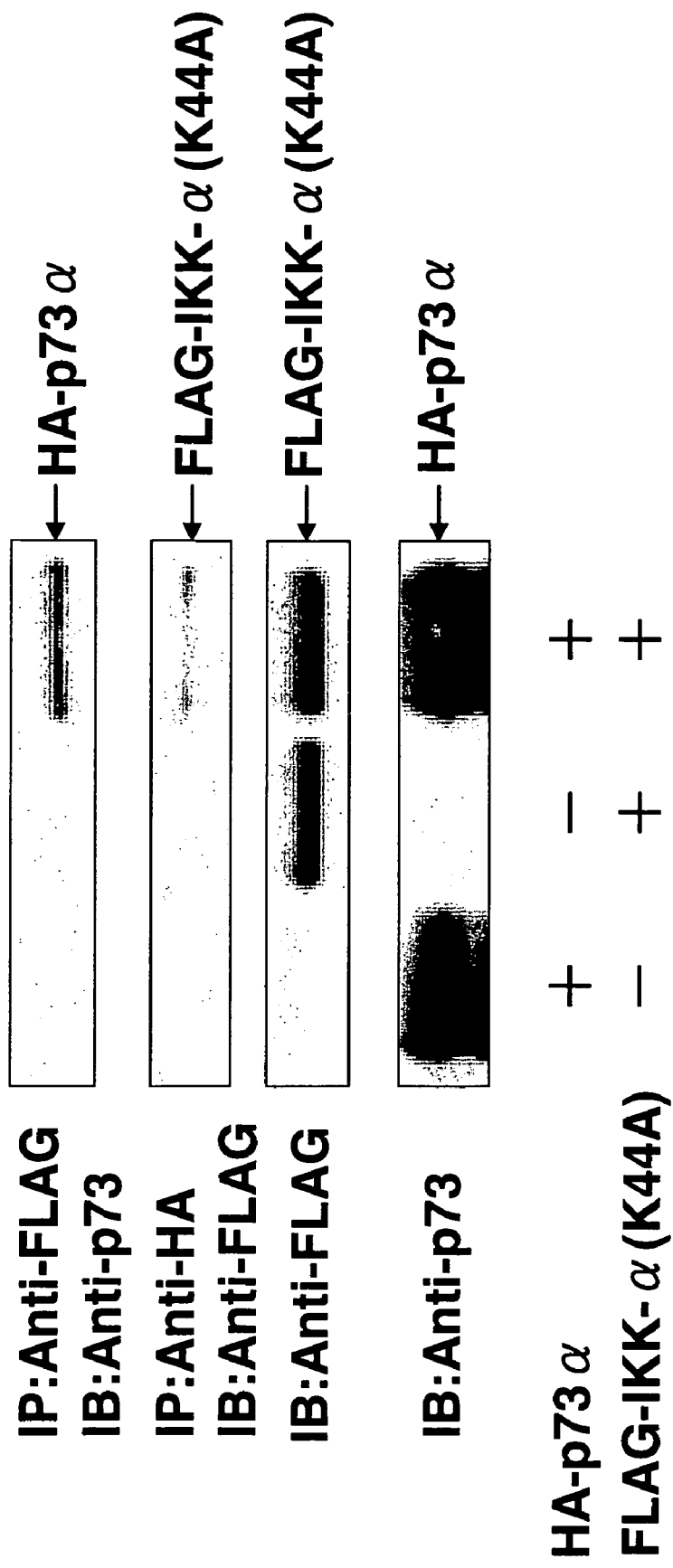
FIG. 28 is a diagram showing a result of immunoprecipitation and immunoblot of COS7 cells transiently cotransfected with given expression plasmids.
Figure 29:
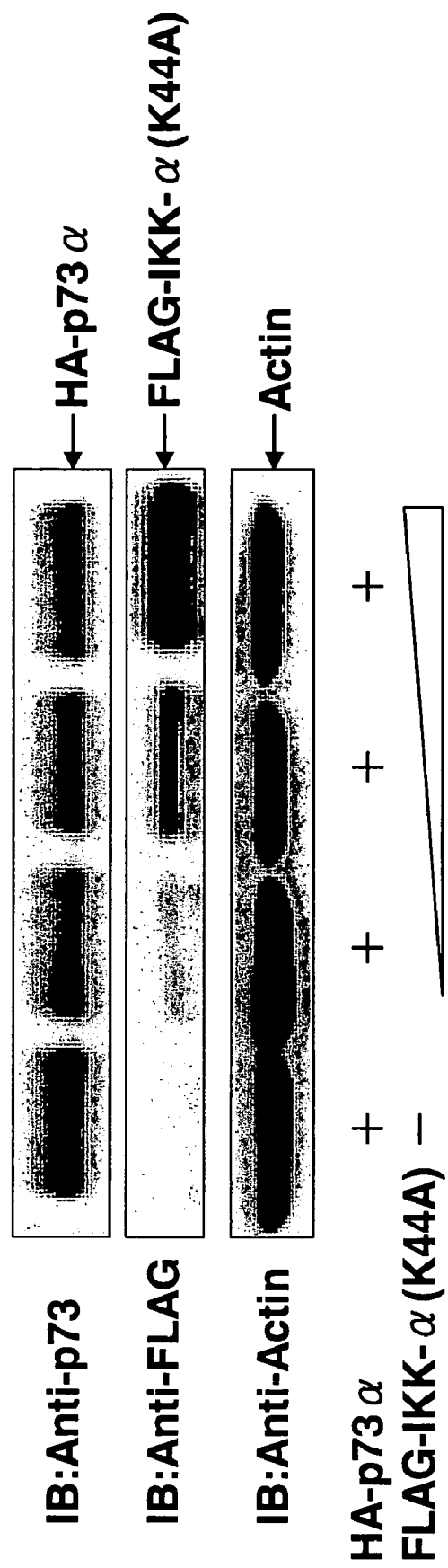
FIG. 29 is a diagram showing a result of immunoprecipitation and immunoblot of COS7 cells transiently cotransfected with given expression plasmids.
Figure 30:
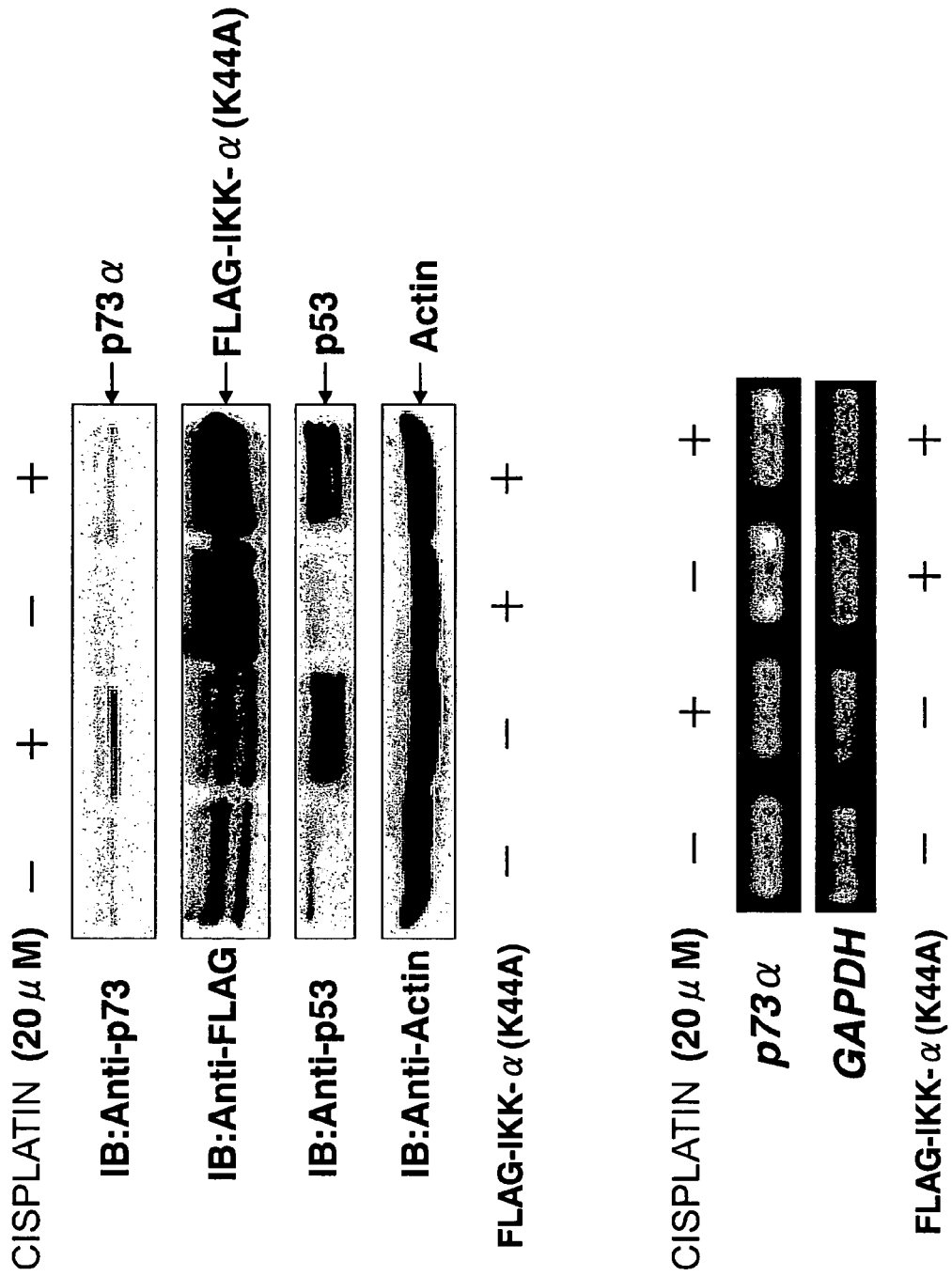
FIG. 30 is a diagram showing a result of immunoblot (upper panels) and RT-PCR analysis (lower panels) of U2OS cells transfected or untransfected with FLAG-IKK-α (K44A) and then treated or untreated with cisplatin.
Figure 31:
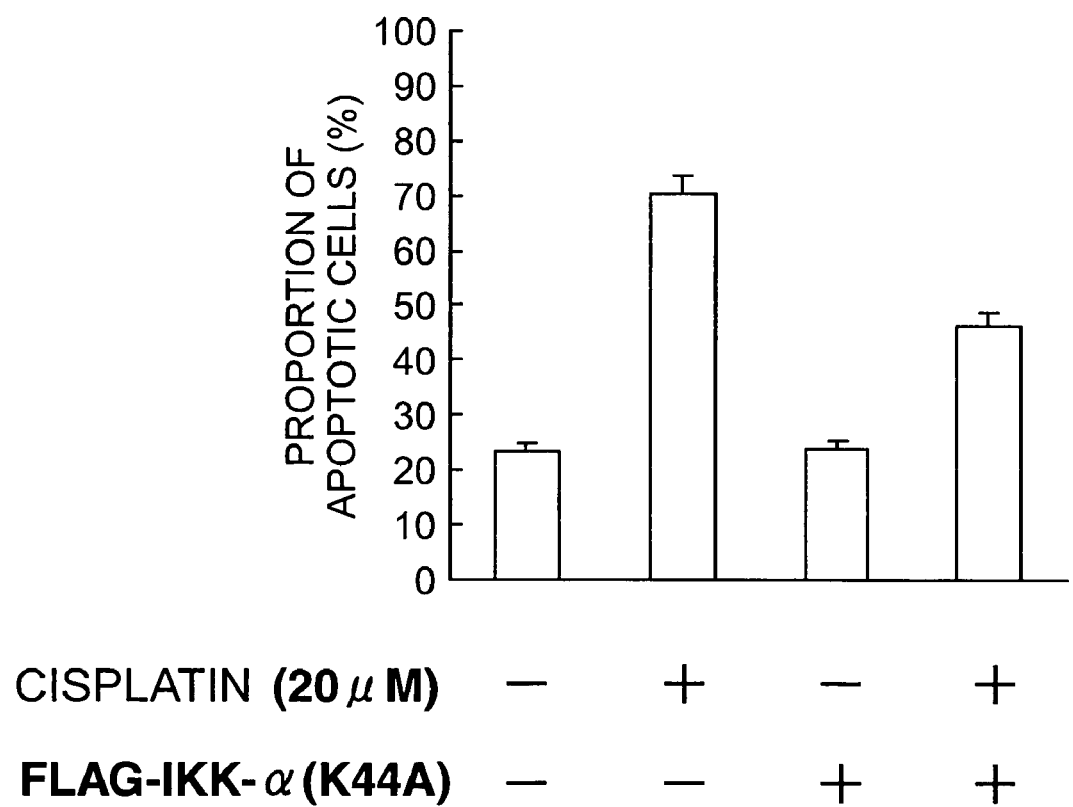
FIG. 31 is a graph showing the proportion of apoptotic cells to U2OS cells transfected with a β-galactosidase expression plasmid together with or without a FLAG-IKK-α (K44A) expression plasmid.
Figure 32:
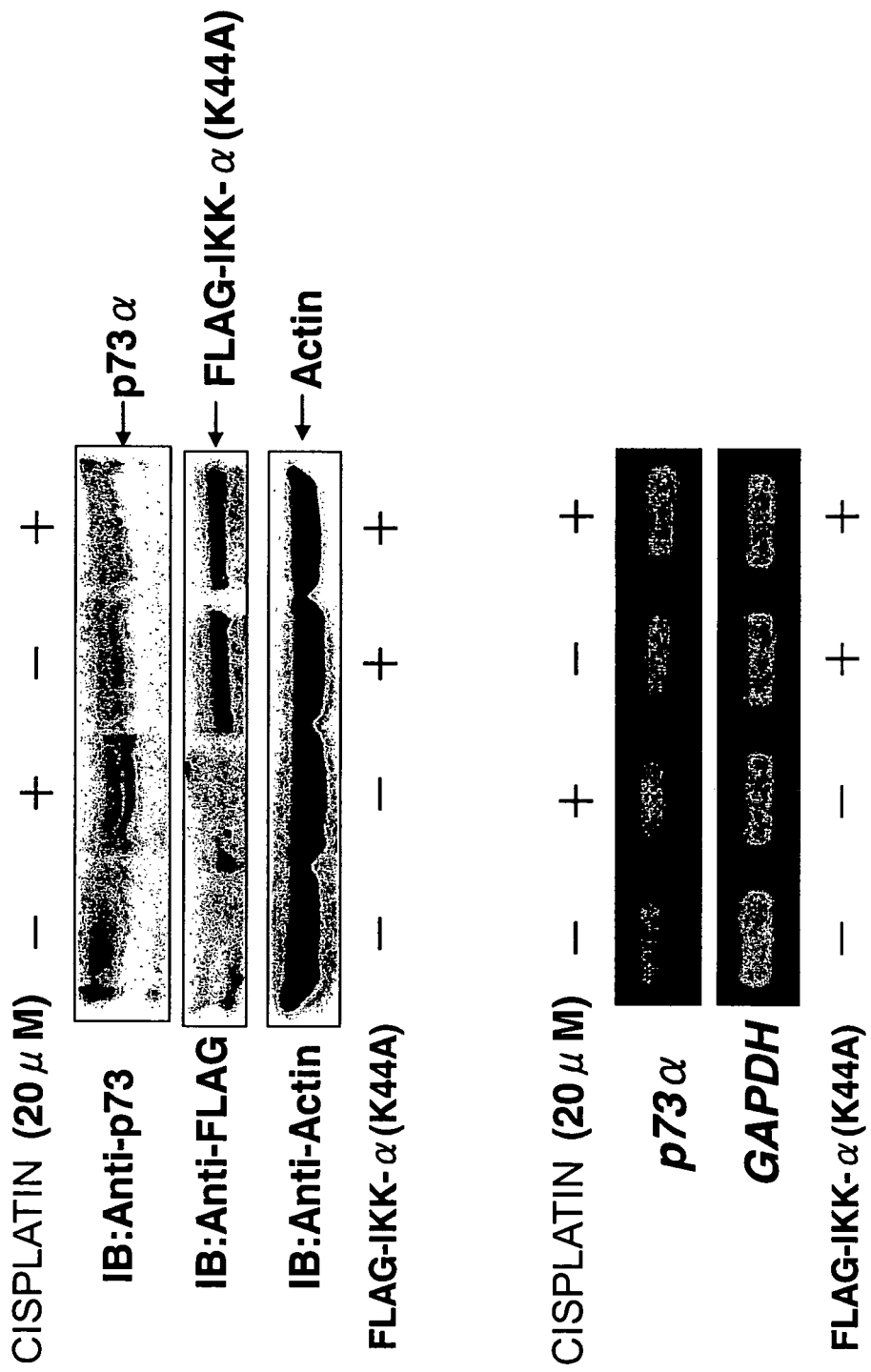
FIG. 32 is a diagram showing a result of immunoblot (upper panels) and RT-PCR analysis (lower panels) of H1299 cells transfected or untransfected with FLAG-IKK-α (K44A) and then treated or untreated with cisplatin.
Figure 33:
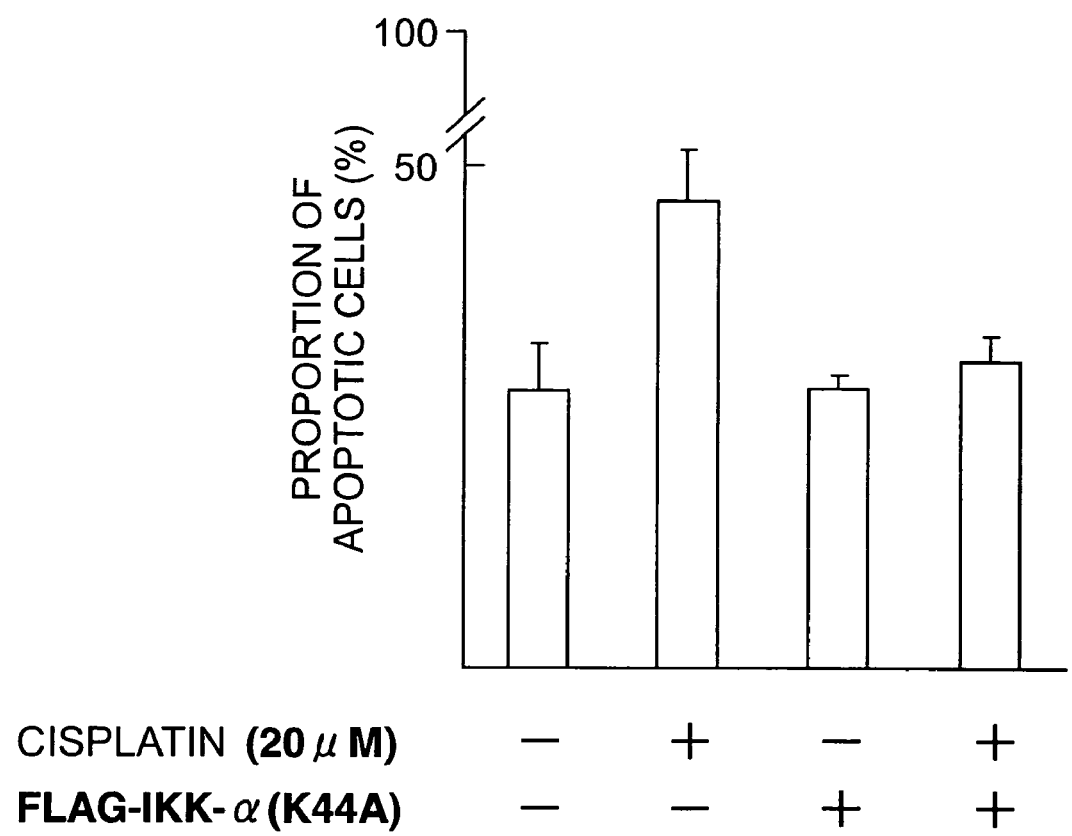
FIG. 33 is a graph showing the proportion of apoptotic cells to H1299 cells transfected with a β-galactosidase expression plasmid together with or without a FLAG-IKK-α (K44A) expression plasmid.
Figure 34:
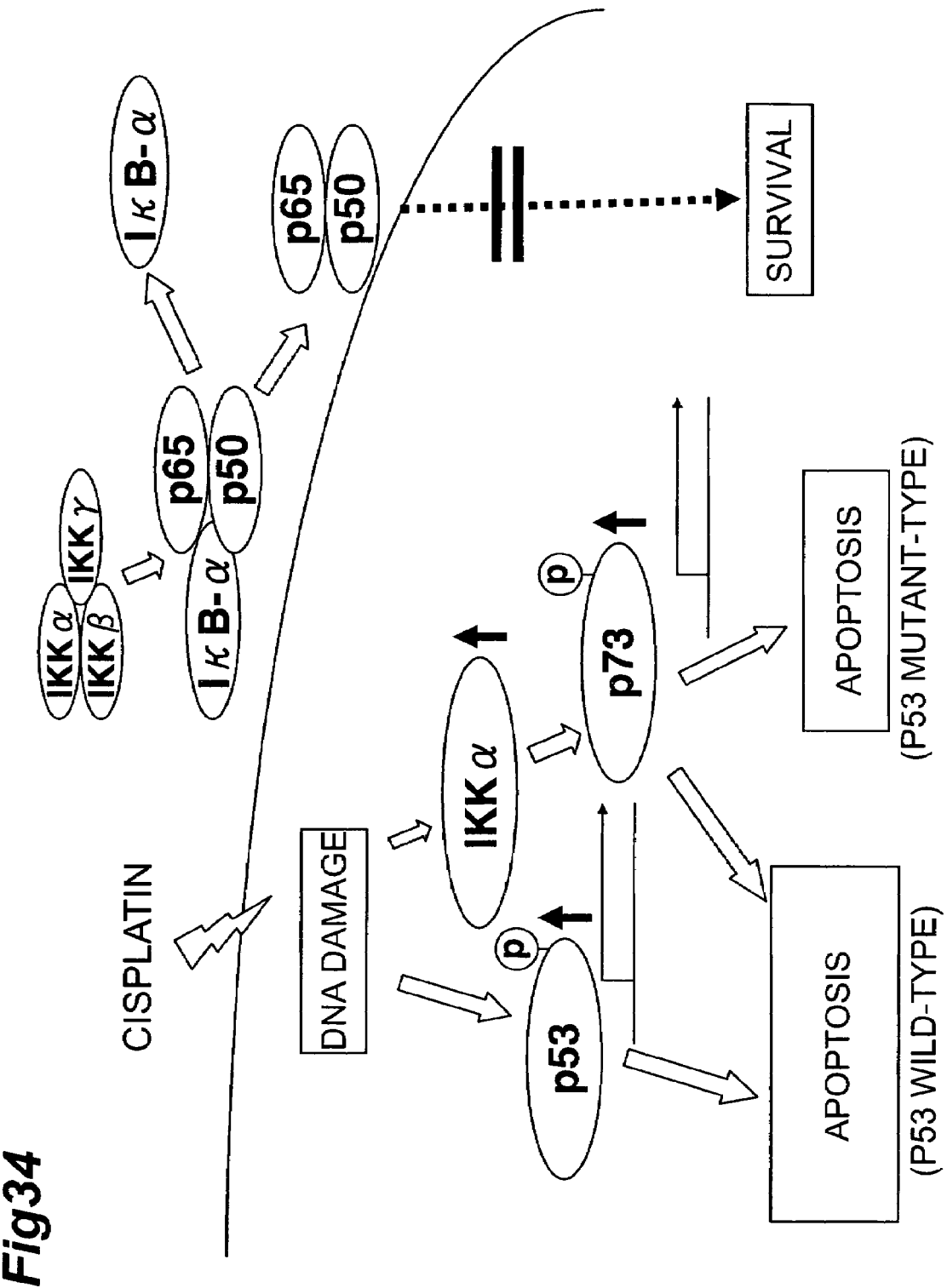
FIG. 34 shows a schematic diagram of IKK, p73, and NF-κB in apoptosis induced by DNA damage.

To investigate whether the endogenous kinase activity of IKK-α was required for the stabilization of p73, IKK-α (K44A) was prepared as mutant IKK-α. This mutant had alanine substituted for lysine-44 in the ATP-binding motif. As described by Ling, L. et al., Proc. Natl. Acad. Sci. USA 95: 3792-3797 (1998), the mutation of this site impairs the kinase activity of IKK-α. As seen from immunoprecipitation analysis, IKK-α (K44A) maintained the ability to form complexes with p73α in cultured mammal cells (FIG. 28). In sharp contrast to wild-type IKK-α, the coexpression of FLAG-IKK-α (K44A) had almost no effect on the intracellular level of exogenously expressed HA-p73α (FIG. 29). To examine the effect of IKK-α lacking kinase activity on endogenous p73, U2OS or H1299 cells were transiently transfected with an empty plasmid or FLAG-IKK-α (K44A) expression plasmid and then exposed to cisplatin for 24 hours or left untreated. Whole cell lysates and total RNA were prepared and subjected to immunoblot and RT-PCR, respectively. As shown in FIG. 30, the stabilization of endogenous p73α mediated by cisplatin was inhibited in the U2OS cells transfected with the FLAG-IKK-α (K44A) expression plasmid. On the other hand, FLAG-IKK-α (K44A) had no remarkable effect on the amount of endogenous p53. Similar results were also obtained in p53-deficient H1299 cells (FIG. 32). In good agreement with the results described above, apoptosis induced by cisplatin was remarkably inhibited in the presence of FLAG-IKK-α (K44A) (FIGS. 31 and 33).

Thus, it is concluded that the stabilization of p73 in response to DNA damage induced by cisplatin requires the kinase activity of IKK-α.

Example 9

Influence of UFD2a on Endogenous p73

Figure 35:
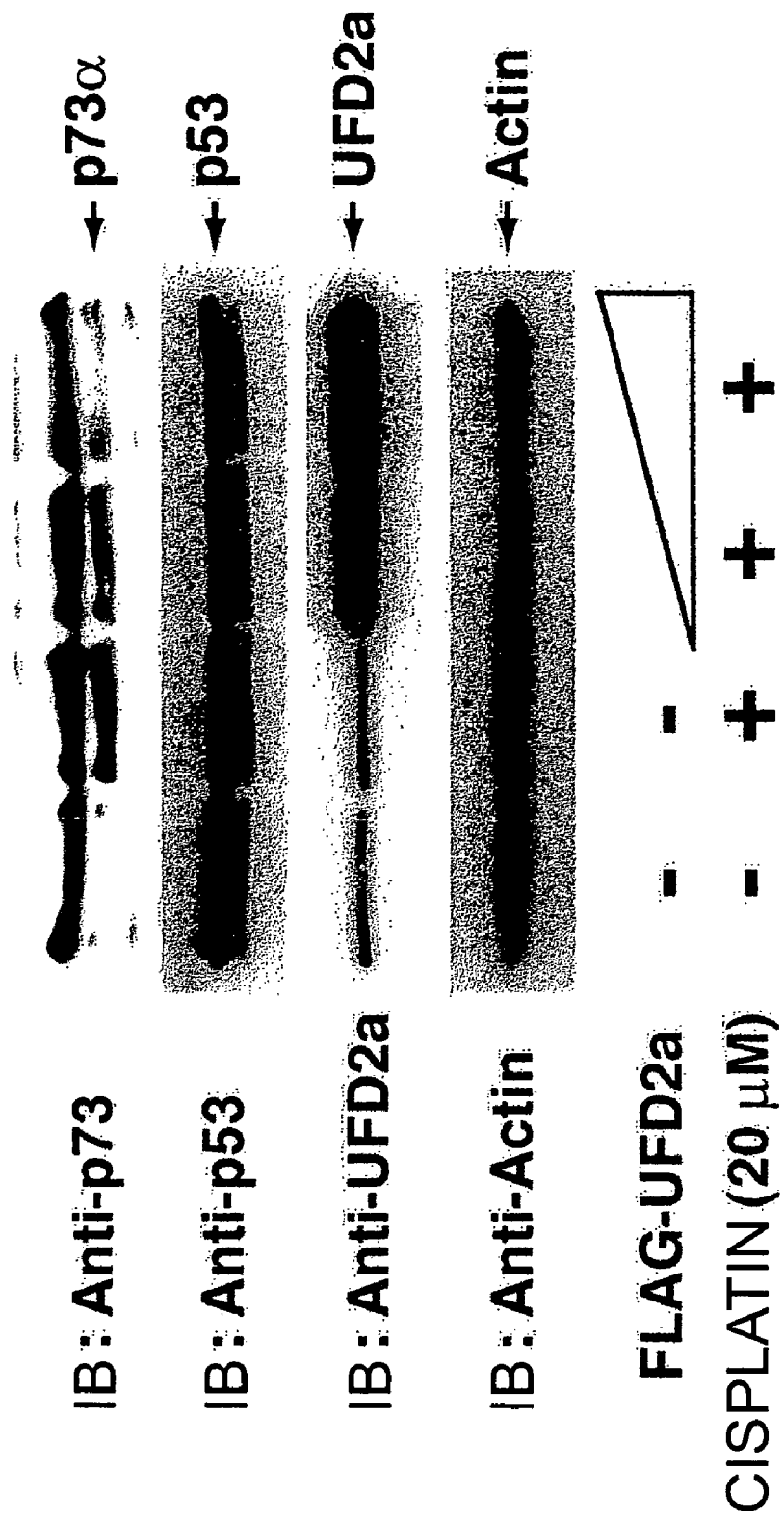
FIG. 35 is a diagram showing a result of immunoblot of COS7 cells transfected or untransfected with FLAG-UFD2a and then treated or untreated with cisplatin.

To examine the influence of UFD2a on endogenous p73, the following experiment was performed. COS7 cells were transfected or untransfected with a FLAG-UFD2a expression plasmid. After 24 hours of the transfection, the cells were exposed to cisplatin (final concentration: 20 μg/mL) for 24 hours or left untreated. Whole cell lysates were prepared from the transfected cells and analyzed for p73α, p53, and UFD2a expression by immunoblot. Actin was utilized as a control for addition. As shown in FIG. 35, the induction of p73α by cisplatin was inhibited in the cells transfected with the FLAG-UFD2a expression plasmid. On the other hand, UFD2a had no influence on the amount of endogenous p53. This result suggests that p73α is degraded by UFD2a.

Example 10

Influence of UFD2a on p73-Dependent Apoptosis

To examine the influence of UFD2a on p73-dependent apoptosis, the following experiment was performed. p53-deficient H1299 cells were transiently cotransfected with the given combinations (HA-p73α, p53, and FLAG-UFD2a) of expression plasmids. After 48 hours of the transfection, the cells were fixed at room temperature for 30 minutes in 3.7% formaldehyde, then permeabilized at room temperature for 5 minutes with 0.2% Triton X-100, and blocked for 1 hour with 3% BSA. The cells were washed three times with 1×PBS and stained at room temperature for 20 minutes with DAPI (4',6-diamidino-2-phenylindole; 1 μg/mL). Of the cells transfected with GFP, cells having abnormal nuclei were counted under a microscope. As shown in FIG. 36, the cotransfection of HA-p73α and FLAG-UFD2a decreased the number of apoptotic cells, as compared with the transfection of HA-p73α alone. By contrast, the cotransfection of p53 and FLAG-UFD2a could not suppress p53-dependent apoptosis.

The results of Examples 9 and 10 revealed that UFD2a degrades p73α and reduces the apoptotic activity of p73α.

INDUSTRIAL APPLICABILITY

According to the screening method of the present invention, pro- and anti-apoptotic compounds with a new and totally different mechanism of action can be obtained. The discovery of such compounds allows for the development of drugs effective for the treatment and prevention of cancer or neurodegenerative disease.

The invention claimed is:

1. A method for screening a pro-apoptotic compound comprising:
   a culture step of culturing cells expressing p73 and IKK-α under respective conditions of being in the presence of and in the absence of a test compound;
   an assay step of assaying the interactions between p73 and IKK-α in the respective cultured cells; and
   a determination step of determining the test compound as a pro-apoptotic compound, where the interaction between p73 and IKK-α in the cell cultured in the presence of the test compound is stronger than the interaction between p73 and IKK-α in the cell cultured in the absence of the test compound.

\* \* \* \* \*